US006720159B1

(12) United States Patent
Serrero

(10) Patent No.: US 6,720,159 B1
(45) Date of Patent: Apr. 13, 2004

(54) 88KDA TUMORIGENIC GROWTH FACTOR AND ANTAGONISTS

(75) Inventor: Ginette Serrero, Ellicott City, MD (US)

(73) Assignee: A&G Pharmaceutical, Inc., Columbia, MD (US)

( * ) Notice: Subject to any disclaimer, the term of this patent is extended or adjusted under 35 U.S.C. 154(b) by 0 days.

(21) Appl. No.: 09/456,886

(22) Filed: Dec. 8, 1999

Related U.S. Application Data

(62) Division of application No. 08/991,862, filed on Dec. 16, 1997, now Pat. No. 6,309,826.

(51) Int. Cl.⁷ .................. G01N 33/574; G01N 33/53; G01N 33/543; G01N 33/563
(52) U.S. Cl. .................. 435/7.23; 435/7.1; 435/7.92; 436/501; 436/64; 436/518
(58) Field of Search .................. 435/7.1, 7.23, 435/7.92; 436/64, 501, 518

(56) References Cited

U.S. PATENT DOCUMENTS

| | | | |
|---|---|---|---|
| 5,416,192 A | * | 5/1995 | Shoyab et al. |
| 5,543,291 A | * | 8/1996 | Keyomarsi et al. |
| 6,309,826 B1 | | 10/2001 | Serrero |
| 6,511,986 B2 | | 1/2003 | Zhang et al. |

FOREIGN PATENT DOCUMENTS

| | | | |
|---|---|---|---|
| WO | WO 91/15510 | * | 10/1991 |
| WO | WO 91 15510 A | | 10/1991 |
| WO | WO 93/15195 | * | 8/1993 |

OTHER PUBLICATIONS

Narita, Takeo, Autocrine Growth Factor and Spontaneous Transformation of Rat Liver Epithelial Cells, In Vitro Cell. Dev. Biol. (1990), 26 (4), 330–4.*
*Effect of Testosterone on the Growth Properties and on Epidermal Growth Factor Receptor Expression in the Teratoma–derived Tumorigenic Cell Line 1246 –3A*, Serrero, G. et al., Cancer Research 52, 1992, pp. 4242–4247.
*Molecular Biology of the Cell*, Alberts, B., et al., Garland Publishing, Inc., 1983.
*Growth Factors in Development, Transformation, and Tumorigenesis*, Cross, M. et al., Cell, vol. 64, 1991, pp. 271–280.
*Autocrine Secretion and Malignant Transformation of Cells*, Sporn, M.B. et al., The New England Journal of Medicine, vol. 303, 1980, pp. 878–880.
*Purification of an Autocrine Growth Factor Homologous with Mouse Epithelin Precursor from a Highly Tumorigenic Cell Line*, Zhou, J. et al., The Journal of Biological Chemistry, vol. 268, No. 15, 1993, pp. 10863–10869.
*The Epithelin Precursor Encodes Two Proteins with Opposing Activities on Epithelial Cell Growth*, Plowman, G. et al., The Journal of Biological Chemistry, vol. 267, No. 18, 1992, pp. 13073–13078.

*Granulins, a Novel Class of Peptide from Leukocytes*, Bateman, A. et al., Biochemical and Biophysical Research Communications, vol. 173, No. 3, 1990, pp. 1161–1168.
*A Synthetic Fragment of Rat Transforming Growth Factor with Receptor Binding and Antigenic Properties*, Nestor, J. et al., Biochemical and Biophysical Research Communications, vol. 129, No. 1, 1985, pp. 226–232.
*In Vitro Deletional Mutagenesis for Bacterial Production of the 20,000–Dalton Form of Human Pituitary Growth Hormone*, Adelman, J. et al., DNA, vol. 2, No. 3, 1983, pps. 183–193.
*An In Vitro Model to Study Adipose Differentiation in Serum–Free Medium*, Serrero, G. et al., Analytical Biochemistry 120, 1982, pp. 351–359.
*Study of a Teratoma–Derived Adipogenic Cell Line 1246 and Isolation of an Insulin–Independent Variant in Serum–Free Medium*, Serrero–Dave, G., Cancer Center, University of California, pp. 366–376.
*Tumorigenicity Associated with Loss of Differentiation and of Response to Insulin in the Adipogenic Cell Line 1246*, Serrero, G., In Vitro Cellular & Developmental Biology, vol. 21, No. 9, 1985, pp. 537–540.
*Decreased Transforming Growth Factor–β Response and Binding in Insulin–independent Teratoma–Derived Cell Lines with Increased Tumorigenic Properties*, Serrero, G. et al., Journal of Cellular Physiology, 149, 1991, pp 503–511.
*Growth Inhibition of Human Breast Cancer Cells in Vitro with an Antibody against the Type I Somatomedin Receptor*, Arteaga, C. et al., Cancer Research 49, 1989, pp. 6237–6241.
*The Biological Effects of a High Molecular Weight Form of IGF II in a Pluripotential Human Teratocarcinoma Cell Line*, Schofield, P. et al., Anticancer Research 14, 1994, pp. 533–538.
*Gene therapy of murine teratocarcinoma: Separate functions for insulin–like growth factors I and II in immunogenicity and differentiation*, Trojan, J. et al., Proc. Natl. Acad. Sci. USA, vol. 91, 1994, pp. 6088–6092.
*Treatment and Prevention of Rat Glioblastoma by Immunogenic C6 Cells Expressing Antisense Insulin–Like Growth Factor I RNA*, Trojan, J. et al., Science, vol. 259, 1993, pp. 94–96.

(List continued on next page.)

Primary Examiner—Mary E. Mosher
Assistant Examiner—Misook Yu
(74) Attorney, Agent, or Firm—Dickstein Shapiro Morin & Oshinsky LLP

(57) ABSTRACT

This invention relates to products and methods for treating cancer and for diagnosing tumorigenicity and other diseases associated with alteration in GP88 expression or action. Antagonists to an 88 KDa autocrine growth and tumorigenicity stimulator are provided which inhibit its expression or biological activity. The antagonists include antisense oligonucleotides and antibodies.

35 Claims, 19 Drawing Sheets

OTHER PUBLICATIONS

*Continuous cultures of fused cells secreting antibody of predefined specificity*, Kohler, G. et al., Nature, vol. 256, 1975, pp. 495–497.

*Production of Monoclonal Antibodies: Strategy and Tactics*, de St. Groth, S.F. et al., Journal of Immunology Methods, 35, 1980, pp. 1–21.

*Hybridoma Techniques*, Schreier, M. et al., Cold Spring Harbor Laboratory, 1980.

*Generation of antibody activity from immunoglobulin polypeptide chains produced in Escherichia coli*, Cabilly, S. et al., Proc. Natl. Acad. Sci. USA, vol. 81, 1984, pp. 3273–3277.

*Chimeric human antibody molecules: Mouse antigen–binding domains with human constant region domains*, Morrison, S. et al., Proc. Natl. Acad. Sci. USA, vol. 81, 1984, pp. 6851–6855.

*Chimeric mouse–human IgG1 antibody that can mediate lysis of cancer cells*, Liu, A. et al., Proc. Natl. Acad. Sci. USA, vol. 84, 1987, pp. 3439–3443.

*Escherichia coli Secretion of an Active Chimeric Antibody Fragment*, Better, M. et al., Science, vol. 240, 1988, pp. 1041–1043.

*Reshaping human antibodies for therapy*, Riechmann, L. et al., Nature, vol. 332, 1988, pp. 323–327.

*Antibody Humanization Using Monovalent Phage Display*, Baca, M. et al., J. Biol. Chem., vol. 272, No. 16, 1997, pp. 10678–10684.

*A Combination Library Strategy for the Rapid Humanization of Anticarcinoma BR96 Fab*, Rosok, M.J. et al., J. Biol. Chem., vol. 271, No. 37, 1996, pp. 22611–22618.

*Improved Radioimaging and Tumor Localization with Monoclonal F(ab')*, Wahl, R.L. et al., The Journal of Nuclear Medicine, vol. 24, No. 4, 1983, pp. 316–325.

*Clinical Use of a Monoclonal Antibody to Bombesin–lik Peptide in Patients with Lung Cancer*, Mulshine, J.L., Annals New York Academy of Sciences, pp. 360–372.

*Antisense RNA inhibits splicing of pre–mRNA in vitro*, Munroe, S.H., The EMBO Journal, vol. 7, No. 8, 1988, pp. 2523–2532.

*Specific Synthesis of DNA in Vitro via a Polymerase–Catalyzed Chain Reaction*, Mulis, K.B. et al., Methods in Enzymology, vol. 155, 1987, pp. 335–350.

*Antisense approaches to cancer gene therapy*, Mercola, D. et al., Cancer Gene Therapy, vol. 2, No. 1, 1995, pp. 47–59.

*Gene inhibition using antisense oligodeoxynucleotides*, Wagner, R. W., Nature, vol. 372, 1994, pp. 333–335.

*Molecular Cloning: A Laboratory Manual*, Maniatis, T. et al., Cold Spring Harbor Laboratory, 1982.

*Design and Application of Antisense Oligonucleotides in Cell Culture, in Vivo, and as Therapeutic Agents*, Brysch, W. et al., Cellular and Molecular Neurobiology, vol. 14, No. 5, 1994, pp. 557–568.

*Rational Design of Sequence–specific Oncogene Inhibitors Based on Antisense and Antigene Oligonucleotides*, Helene, C., Eur. J. Cancer, vol. 27, No. 11, 1991, pp. 1466–1471.

*Optimization of Antisense Oligodeoxynucleotide Structure for Targeting ber–abl mRNA*, Giles, R.V. et al., Blood, vol. 86, No. 2, 1995, pp. 744–754.

*Extending the chemistry that supports genetic information transfer in vivo: Phosphorothioate DNA, phosphorothioate RNA, 2'–O–methyl RNA, and methylphosphonate DNA*, Thaler, D.S. et al., Proc. Natl. Acad. Sci. USA, vol. 93, 1996, pp. 1352–1356.

*Oligonucleotide N3'–P5' phosphoramidates as antisense agents*, Gryaznov, S. et al., Nucleic Acids Research, vol. 24, No. 8, 1996, pp. 1508–1514.

*Cationic liposomes improve stability and intracellular delivery of antisense oligonucleotides into CaSki cells*, Lappalainen, K. et al., Biochimica et Biophysica Acta 1196, 1994, pp. 201–208.

*Block of AIDS–Kaposi's Sarcoma (KS) Cell Growth, Angiogenesis, and Lesion Formation in Nude Mice by Antisense Oligonucleotide Targeting Basic Fibroblast Growth Factor*, Ensoli, B. et al., The Journal of Clinical Investigation, Inc., vol. 94, 1994, pp. 1736–1746.

*Growth Inhibition of Malignant CD5+B (B–1) Cells by Antisense IL–10 Oligonucleotide*, Peng, B. et al., Leukemia Research, vol. 19, No. 3, 1995, pp. 159–167.

*Review: Optimizing inducer and culture conditions for expression of foreign proteins under the control of the lac promoter*, Donovan, R.S. et al., Journal of Industrial Microbiology, 16, 1996, pp. 145–154.

*Prokaryotic gene expression in vitro: Transcription–translation coupled systems*, Cenatiempo, Y., Biochimie, 68, 1986, pp. 505–515.

*Bacterial Regulation: Global Regulatory Networks*, Gottesman, S., Ann. Rev. Genet., 18, 1984, pp. 415–441.

*Regulation In Vitro of a Cloned Mammalian Gene: Cadmium Induces the Transcription of a Mouse Metallothionein Gene in SV40 Vectors*, Hamer, D.H. et al., Journal of Molecular and Applied Genetics, vol. 1, No. 4, 1982, pp. 273–288.

*Functional Relationships between Transcriptional Control Signals of the Thymidine Kinase Gene of Herpes Simplex Virus*, McKnight, S.L., Cell, vol. 31, 1982, pp. 355–365.

*Isolation of the yeast regulatory gene GAL4 and analysis of its dosage effects on the galactose/melibiose regulon*, Johnston, S.A. et al., Proc. Natl. Acad. Sci. USA, 79, 1982, pp. 6971–6975.

*In vivo sequence requirements of the SV40 early promoter region*, Benoist, C. et al., Nature, vol. 290, 1981, pp. 304–310.

*Cloning, Structure, and Expression of the Mitochondrial Cytochrome P–450 Sterol 26–Hydroxylase, a Bile Acid Biosynthetic Enzyme*, Andersson, S. et al., The Journal of Biological Chemistry, vol. 264, No. 14, 1989, pp. 8222–8229.

*Insulin and Insulin–like Growth Factor Signaling Are Defective in the MDA MB–468 Human Breast Cancer Cell Line*, Sepp–Lorenzino, L. et al., Cell Growth & Differentiation, vol. 5, 1994, pp. 1077–1083.

*Biochemical Analysis of the Epithelin Receptor*, Culouscou, J.M. et al., The Journal of Biological Chemistry, vol. 268, No. 14, 1993, pp. 10458–10462.

*Targeted Toxins as Anticancer Agents*, Siegall, C.B., Cancer, vol. 74, No. 3, 1994, pp. 1006–1012.

Zhang Haidi, "Overexpression of PC cell derived growth factor (PCDGF) contributes to the highly tumorigenic properties of producer cell line PC," Diss. Abstr. Int., vol. 58, No. 11, 1998, p. 5814–B XP001025915, abstract.

Vijay Bandhari and Andrew Bateman, "Structure and Chromosmal Location of the human granulin gene," Biochemical and Biophysical Research Communications, vol. 188, No. 1, 1992, pp. 57–63, XP001018991, abstract, figure 2.

Bhandari et al., "The Complementary Deoxyribonucleic Acid Sequence, Tissue Distribution, and Cellular Localization of the Rat Granulin Precursor," Endocrinology, vol. 133, No. 6, 1993, pp. 2682–2689, XP001021601.

Haidi Zhang and Ginette Serrero, "Inhibition of Tumorigenicity of the teratoma PC cell line by transfection with antisense cDNA for PC cell–derived growth factor (PCDGF, epithelin/granulin precursor)," PNAS, vol. 95, Nov. 1998, pp. 14202–14207, XP002177206.

European Search Report dated Oct. 23, 2001.

Zhang, Haidi—"Overexpression of PC Cell Derived Growth Factor (PCDGF) Contributes To The Highly Tumorigenic Properties Of Producer Cell Line PC" a Dissertation submitted in partial fulfillment of the requirements for the degree of Doctor of Philosophy, Chemistry, Fall of 1997, 143 pages, Clarkson University.

Vijay Bhandari, et al.—"Isolation and sequence of the granulin precursor cDNA from human bone marrow reveals tandem cysteine–rich granulin domans," Proc. Natl. Acad. Sci. USA, vol. 89, Mar. 1992, pp. 1715–1719.

Runging Lue, et al.—"Inhibition of PC cell–derived growth factor (PCDGF, epithelin/granulin precursor) expression by antisense PCDGF cDNA transfection inhibits tumorigenicity of the human breast carcinoma cell line MDA–MB–468," PNAS, vol. 97, No. 8, Apr. 11, 2000, pp. 3993–3998.

Zhiheng He, et al.—"Progranulin Gene Expression Regulates Epithelial Cell Growth and Promotes Tumor Growth in Vivo[1]," Cancer Research 59, Jul. 1, 1999, pp. 3222–3229.

International Search Report dated May 13, 2003.

* cited by examiner

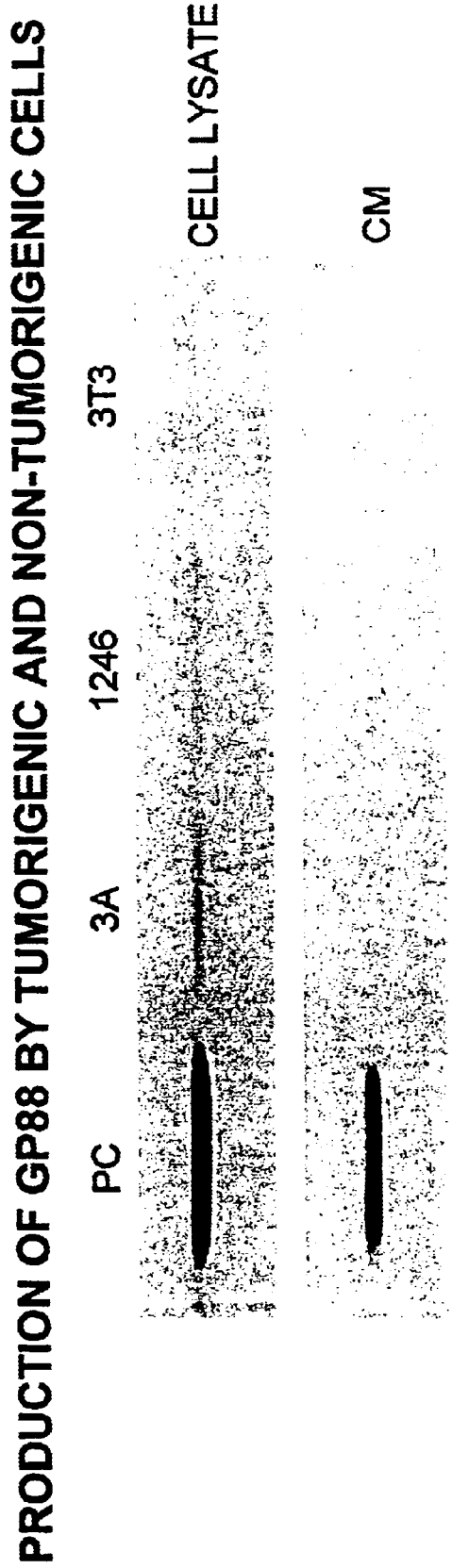

GP88 PROTEIN EXPRESSION IN TUMOR AND SURROUNDING TISSUES

Mouse GP88 cDNA

| | | | | | | | | | | | | | | | |
|---|---|---|---|---|---|---|---|---|---|---|---|---|---|---|---|
| C | GGA | CCC | CGA | CGC | AGA | CAG | ACC | ATG | TGG | GTC | CTG | ATG | AGC | TGG | CTG | 46 |
| | | | | | | | | M | W | V | L | M | S | W | L | 8 |
| GCC | TTC | GCG | GCA | GGG | CTG | GTA | GCC | GGA | ACA | CAG | TGT | CCA | GAT | GGG | CAG | 94 |
| A | F | A | A | G | L | V | A | G | T | Q | C | P | D | G | Q | 24 |
| TTC | TGC | CCT | GTT | GCC | TGC | TGC | CTT | GAC | CAG | GGA | GGA | GCC | AAC | TAC | AGC | 142 |
| F | C | P | V | A | C | C | L | D | Q | G | G | A | N | Y | S | 40 |
| TGC | TGT | AAC | CCT | CTT | CTG | GAC | ACA | TGG | CCT | AGA | ATA | ACG | AGC | CAT | CAT | 190 |
| C | C | N | P | L | L | D | T | W | P | R | I | T | S | H | H | 56 |
| CTA | GAT | GGC | TCC | TGC | CAG | ACC | CAT | GGC | CAC | TGT | CCT | GCT | GGC | TAT | TCT | 238 |
| L | D | G | S | C | Q | T | H | G | H | C | P | A | G | Y | S | 72 |
| TGT | CTT | CTC | ACT | GTG | TCT | GGG | ACT | TCC | AGC | TGC | TGC | CCG | TTC | TCT | AAG | 286 |
| C | L | L | T | V | S | G | T | S | S | C | C | P | F | S | K | 88 |
| GGT | GTG | TCT | TGT | GGT | GAT | GGC | TAC | CAC | TGC | TGC | CCC | CAG | GGC | TTC | CAC | 334 |
| G | V | S | C | G | D | G | Y | H | C | C | P | Q | G | F | H | 104 |
| TGT | AGT | GCA | GAT | GGG | AAA | TCC | TGC | TTC | CAG | ATG | TCA | GAT | AAC | CCC | TTG | 382 |
| C | S | A | D | G | K | S | C | F | Q | M | S | D | N | P | L | 120 |
| GGT | GCT | GTC | CAG | TGT | CCT | GGG | AGC | CAG | TTT | GAA | TGT | CCT | GAC | TCT | GCC | 430 |
| G | A | V | Q | C | P | G | S | Q | F | E | C | P | D | S | A | 136 |
| ACC | TGC | TGC | ATT | ATG | GTT | GAT | GGT | TCG | TGG | GGA | TGT | TGT | CCC | ATG | CCC | 478 |
| T | C | C | I | M | V | D | G | S | W | G | C | C | P | M | P | 152 |
| CAG | GCC | TCT | TGC | TGT | GAA | GAC | AGA | GTG | CAT | TGC | TGT | CCC | CAT | GGG | GCC | 526 |
| Q | A | S | C | C | E | D | R | V | H | C | C | P | H | G | A | 168 |
| TCC | TGT | GAC | CTG | GTT | CAC | ACA | CGA | TGC | GTT | TCA | CCC | ACG | GGC | ACC | CAC | 574 |
| S | C | D | L | V | H | T | R | C | V | S | P | T | G | T | H | 184 |
| ACC | CTA | CTA | AAG | AAG | TTC | CCT | GCA | CAA | AAG | ACC | AAC | AGG | GCA | GTG | TCT | 622 |
| T | L | L | K | K | F | P | A | Q | K | T | N | R | A | V | S | 200 |
| TTG | CCT | TTT | TCT | GTC | GTG | TGC | CCT | GAT | GCT | AAG | ACC | CAG | TGT | CCC | GAT | 670 |
| L | P | F | S | V | V | C | P | D | A | K | T | Q | C | P | D | 216 |

FIG.8A

Mouse GP88 cDNA (continued)

```
GAT TCT ACC TGC TGT GAG CTA CCC ACT GGG AAG TAT GGC TGC TGT CCA    718
 D   S   T   C   C   E   L   P   T   G   K   Y   G   C   C   P     232

ATG CCC AAT GCC ATC TGC TGT TCC GAC CAC CTG CAC TGC TGC CCC CAG    766
 M   P   N   A   I   C   C   S   D   H   L   H   C   C   P   Q     248

GAC ACT GTA TGT GAC CTG ATC CAG AGT AAG TGC CTA TCC AAG AAC TAC    814
 D   T   V   C   D   L   I   Q   S   K   C   L   S   K   N   Y     264

ACC ACG GAT CTC CTG ACC AAG CTG CCT GGA TAC CCA GTG AAG GAG GTG    862
 T   T   D   L   L   T   K   L   P   G   Y   P   V   K   E   V     280

AAG TGC GAC ATG GAG GTG AGC TGC CCT GAA GGA TAT ACC TGC TGC CGC    910
 K   C   D   M   E   V   S   C   P   E   G   Y   T   C   C   R     296

CTC AAC ACT GGG GCC TGG GGC TGC TGT CCA TTT GCC AAG GCC GTG TGT    958
 L   N   T   G   A   W   G   C   C   P   F   A   K   A   V   C     312

TGT GAG GAT CAC ATT CAT TGC TGC CCG GCA GGG TTT CAG TGT CAC ACA   1006
 C   E   D   H   I   H   C   C   P   A   G   F   Q   C   H   T     328

GAG AAA GGA ACC TGC GAA ATG GGT ATC CTC CAA GTA CCC TGG ATG AAG   1054
 E   K   G   T   C   E   X   G   I   L   Q   V   P   W   M   K     344

AAG GTC ATA GCC CCC CTC CGC CTG CCA GAC CCA CAG ATC TTG AAG AGT   1102
 K   V   I   A   P   L   R   L   P   D   P   Q   I   L   K   S     360

GAT ACA CCT TGT GAT GAC TTC ACT AGG TGT CCT ACA AAC AAT ACC TGC   1150
 D   T   P   C   D   D   F   T   R   C   P   T   N   N   T   C     376

TGC AAA CTC AAT TCT GGG GAC TGG GGC TGC TGT CCC ATC CCA GAG GCT   1198
 C   K   L   N   S   G   D   W   G   C   C   P   I   P   E   A     392

GTC TGC TGC TCA GAC AAC CAG CAT TGC TGC CCT CAG GGC TTC ACA TGT   1246
 V   C   C   S   D   N   Q   H   C   C   P   Q   G   F   T   C     408

CTG GCT CAG GGG TAC TGT CAG AAG GGA GAC ACA ATG GTG GCT GGC CTG   1294
 L   A   Q   G   Y   C   Q   K   G   D   T   M   V   A   G   L     424

GAG AAG ATA CCT GCC CGC CAG ACA ACC CCG CTC CAA ATT GGA GAT ATC   1342
 E   K   I   P   A   R   Q   T   T   P   L   Q   I   G   D   I     440
```

FIG.8B

Mouse GP88 cDNA (continued)

```
GGT TGT GAC CAG CAT ACC AGC TGC CCA GTA GGG CAA ACC TGC TGC CCA    1390
 G   C   D   Q   H   T   S   C   P   V   G   Q   T   C   C   P     456

AGC CTC AAG GGA AGT TGG GCC TGC TGC CAG CTG CCC CAT GCT GTG TGC    1438
 S   L   K   G   S   W   A   C   C   Q   L   P   H   A   V   C     472

TGT GAG GAC CGG CAG CAC TGT TGC CCG GCC GGG TAC ACC TGC AAC GTG    1486
 C   E   D   R   Q   H   C   C   P   A   G   Y   T   C   N   V     488

AAG GCG AGG ACC TGT GAG AAG GAT GTC GAT TTT ATC CAG CCT CCC GTG    1534
 K   A   R   T   C   E   K   D   V   D   F   I   Q   P   P   V     504

CTC CTG ACC CTC GGC CCT AAG GTT GGG AAT GTG GAG TGT GGA GAA GGG    1582
 L   L   T   L   G   P   K   V   G   N   V   E   C   G   E   G     520

CAT TTC TGC CAT GAT AAC CAG ACC TGT TGT AAA GAC AGT GCA GGA GTC    1630
 H   F   C   H   D   N   Q   T   C   C   K   D   S   A   G   V     536

TGG GCC TGC TGT CCC TAC CTA AAG GGT GTC TGC TGT AGA GAT GGA CGT    1678
 W   A   C   C   P   Y   L   K   G   V   C   C   R   D   G   R     552

CAC TGT TGC CCC GGT GGC TTC CAC TGT TCA GCC AGG GGA ACC AAG TGT    1726
 H   C   C   P   G   G   F   H   C   S   A   R   G   T   K   C     568

TTG CGA AAG AAG ATT CCT CGC TGG GAC ATG TTT TTG AGG GAT CCG GTC    1774
 L   R   K   K   I   P   R   W   D   M   F   L   R   D   P   V     584

CCA ACA CCG CTA CTG TAA GGA AGG GCT ACA GAC TTA AGG AAC TCC ACA    1822
 P   T   P   L   L   *                                              589

GTC CTG GGA ACC TGT TTC CGA GGG TAC CCA CTA CTC AGG CCT CCC TAG    1870
CGC CTC CTC CCC TAA CGT CTC CCC GGC CTA CTC ATC CTG AGT CAC CCT    1918
ATC ACC ATG GGA GGT GGA GCC TCA AAC TAA AAC CTT CTT TTA TGG AAA    1966
GAA GGC TGT GGC CAA AAG CCC CGT ATC AAA CTG CCA TTT CTT CCG GTT    2014
TCT GTG GAC CTT GTG GCC AGG TGC TCT TCC CGA GCC ACA GGT GTT CTG    2062
TGA GCT TGC TTG TGT GTG TGT GCG CGT GTG CGT GTG TTG CTC CAA TAA    2110
AGT TTG TAC GCT TTC TGA AAA AAA AAA                                2137
```

FIG.8C

Nucleotide sequence of human granulin/epithelin precursor (human GP88).
Human Granulin Genbank M75161$ cgcaggcaga ccatgtggac cttggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgccccttc ccagaggccg tggcatgcgg ggatggccat
cactgctgcc cacggggctt ccactgcagt gcagacggga gatcctgctt ccaaagatca
ggtaacaact ccgtgggtgc catccagtgc cctgatagtc agttcgaatg cccggacttc
tccacgtgct gtgttatggt cgatggctcc tgggggtgct gccccatgcc ccaggcttcc
tgctgtgaag acagggtgca ctgctgtccg cacggtgcct tctgcgacct ggttcacacc
cgctgcatca cacccacggg cacccacccc ctggcaaaga agctccctgc ccagaggact
aacagggcag tggccttgtc cagctcggtc atgtgtccgg acgcacggtc ccggtgccct
gatggttcta cctgctgtga gctgcccagt gggaagtatg gctgctgccc aatgcccaac
gccacctgct gctccgatca cctgcactgc tgcccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctatacctgc
tgccgtctac agtcgggggc ctggggctgc tgccctttta cccaggctgt gtgctgtgag
gaccacatac actgctgtcc cgcggggttt acgtgtgaca cgcagaaggg tacctgtgaa
caggggcccc accaggtgcc ctggatggag aaggcccag ctcacctcag cctgccagac
ccacaagcct tgaagagaga tgtcccctgt gataatgtca gcagctgtcc ctcctccgat
acctgctgcc aactcacgtc tggggagtgg ggctgctgtc caatcccaga ggctgtctgc
tgctcggacc accagcactg ctgccccag cgatacacgt gtgtagctga ggggcagtgt
cagcgaggaa gcgagatcgt ggctggactg gagaagatgc ctgcccgccg cggttcctta
tcccacccca gagacatcgg ctgtgaccag cacaccagct gcccggtggg cggaacctgc
tgcccgagcc agggtgggag ctgggcctgc tgccagttgc cccatgctgt gtgctgcgag
gatcgccagc actgctgccc ggctggctac acctgcaacg tgaaggctcg atcctgcgag
aaggaagtgg tctctgccca gcctgccacc ttcctggccc gtagccctca cgtgggtgtg
aaggacgtgg agtgtgggga aggacacttc tgccatgata accagacctg ctgccgagac
aaccgacagg gctgggcctg ctgtccctac gcccagggcg tctgttgtgc tgatcggcgc
cactgctgtc ctgctggctt ccgctgcgca cgcagggta ccaagtgttt gcgcagggag
gccccgcgct gggacgcccc tttgagggac ccagccttga gacagctgct gtgagggaca
gtactgaaga ctctgcagcc ctcgggaccc cactcggagg gtgccctctg ctcaggcctc
gtactgaaga ctctgcagcc ctcgggaccc cactcggagg gtgccctctg ctcaggcctc
cctagcacct cccctaacc aaattctccc tggaccccat tctgagctcc ccatcaccat
gggaggtggg gcctcaatct aaggcccttc cctgtcagaa gggggttgag gcaaaagccc
attcaagct gccatcccct ccccgtttca gtggaccctg tggccaggtg cttttcccta
tccacagggg tgtttgtgtg ttgggtgtgc tttcaataaa gtttgtcact ttctt*

FIG.9A

Amino-acid sequence of human granulin/epithelin precursor (human GP88).

MWTLVSWVALTAGLVAGTRCPDGQFCPVACCLDPGGASYSCCRP
LLDKWPTTLSRHLGGPCQVDAHCSAGHSCIFTVSGTSSCCPFPEAVACGDGHHCCPRG
FHCSADGRSCFQRSGNNSVGAIQCPDSQFECPDFSTCCVMVDGSWGCCPMPQASCCED
RVHCCPHGAFCDLVHTRCITPTGTHPLAKKLPAQRTNRAVALSSSVMCPDARSRCPDG
STCCELPSGKYGCCPMPNATCCSDHLHCCPQDTVCDLIQSKCLSKENATTDLLTYLPA
HTVGDVKCDMEVSCPDGYTCCRLQSGAWGCCPFTQAVCCEDHIHCCPAGFTCDTQKGT
CEQGPHQVPWMEKAPAHLSLPDPQALKRDVPCDNVSSCPSSDTCCQLTSGEWGCCPIP
EAVCCSDHQHCCPQRYTCVAEGQCQRGSEIVAGLEKMPARRGSLSHPRDIGCDQHTSC
PVGGTCCPSQGGSWACCQLPHAVCCEDRQHCCPAGYTCNVKARSCEKEVVSAQPATFL
ARSPHVGVKDVECGEGHFCHDNQTCCRDNRQGWACCPYAQGVCCADRRHCCPAGFRCA
RRGTKCLRREAPRWDAPLRDPALRQLL*

FIG.9B

Mouse GP88 protein sequence

MWVLMSWLAFAAGLVAG 17

TQCPDGQF-CPVA--CCLDQG-GANYSCCNPLLDTMPRITSHHL 57

DGSC-QTHGHCPAGY-SCLLTVSGTS-SCCPFSKGVSCGDGYHCCPQGFHCSADGKSCFQMSDNPL 120

GAVQCPGSQFECPDSATCCIMVD-G-SWGCCPMPQASCCEDRVHCCPHGASCDLVHTRCVSPTGTHTLLKKFPAQKTNAAVSLPFS 204   g

VVCPDAKTQCPDDSTCELP-TGK-YGCCPMPNAICCSDHLHCCPQDTVCDLIQSKCLSKNYTDLLTKLPGYPVK 278   f

EVKC-DMEVSCPEGYTCCALN-TGA-WGCCPFAKAVCCEEDHIHCCPAGFQCHTEKGICEMGILQVPWMKKVIAPRRLPDPQILKS 360   2.B

DIPCDDEFTR-CPTNNTCCKLN-SGD-WGCCPIPEAVCCSDNQHCCPQGFTCLAQGY-CQKGDTMVAGLEKIPARQTTPLQIG 438   1.A

DIGCDuHT-SCPVGQTCCPSLK-G-SWACCQLPHAVCCEDRQHCCPAGYTCNVKARTCEKDVDFIQPPVLLTLGPKVG 513   C

NVECGEGHF-CHDNQTCCKDSA-GV-WACCPYLKGVCCRDGRHCCPGGFHCSARGTKCLAKKIPRWDMFLADPVPRPLL 589   D e consensus sequence:

C......C......CC......G....CC......CC.D..HCCP....C.......C 1,2:mouse epithelin 1.2.
A,B,C,D,e,f,g: granulin A,B,C,D,E,F,G;N-terminus of granulin A,B,C,D have been sequenced.
Mouse epithelin precursor sequence is from Plowman et al.(1992).

FIG.10

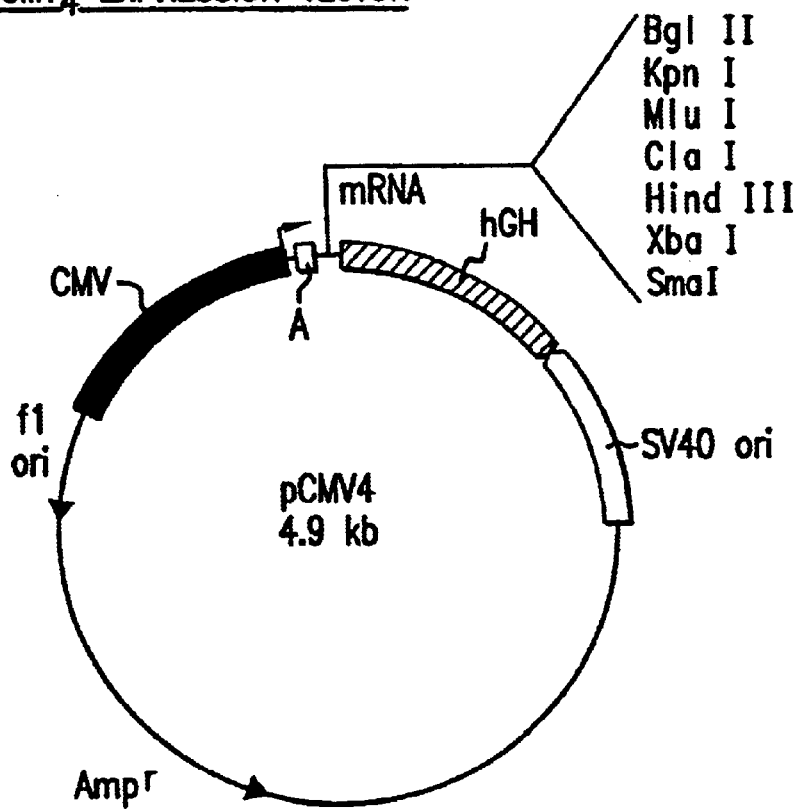
FIG. 11

GP88 EXPRESSION IN NON TUMORIGENIC (MCF 10A) AND MALIGNANT (MCF 7, MDA-468) HUMAN MAMMARY EPITHELIAL CELLS

GP88 EXPRESSION IS INHIBITED BY ANTISENSE GP88 cDNA TRANSFECTION IN HUMAN BREAST CARCINOMA MDA-468

SEQUENCE LISTING

<160> NUMBER OF SEQ ID NOS: 17

<210> SEQ ID NO 1
<211> LENGTH: 2137
<212> TYPE: DNA
<213> ORGANISM: Mouse epithelin/granulin
<220> FEATURE:
<221> NAME/KEY: CDS
<222> LOCATION: (23)..(1789)
<223> OTHER INFORMATION: The sequence is identical to that of the
      published mouse granulin except for one nucleotide (T
      instead of G) at position 1071 of GP88 cDNA
      (position 1056 of mouse granulin).

<400> SEQUENCE: 1

```
cggaccccga cgcagacaga cc atg tgg gtc ctg atg agc tgg ctg gcc ttc      52
                         Met Trp Val Leu Met Ser Trp Leu Ala Phe
                           1               5                  10 gcg gca ggg ctg gta gcc gga aca cag tgt cca gat ggg cag ttc tgc      100
Ala Ala Gly Leu Val Ala Gly Thr Gln Cys Pro Asp Gly Gln Phe Cys
                 15                  20                  25 cct gtt gcc tgc tgc ctt gac cag gga gga gcc aac tac agc tgt tgt      148
Pro Val Ala Cys Cys Leu Asp Gln Gly Gly Ala Asn Tyr Ser Cys Cys
             30                  35                  40 aac cct ctt ctg gac aca tgg cct aga ata acg agc cat cat cta gat      196
Asn Pro Leu Leu Asp Thr Trp Pro Arg Ile Thr Ser His His Leu Asp
         45                  50                  55 ggc tcc tgc cag acc cat ggc cac tgt cct gct ggc tat tct tgt ctt      244
Gly Ser Cys Gln Thr His Gly His Cys Pro Ala Gly Tyr Ser Cys Leu
     60                  65                  70 ctc act gtg tct ggg act tcc agc tgc tgc ccg ttc tct aag ggt gtg      292
Leu Thr Val Ser Gly Thr Ser Ser Cys Cys Pro Phe Ser Lys Gly Val
 75                  80                  85                  90 tct tgt ggt gat ggc tac cac tgc tgc ccc cag ggc ttc cac tgt agt      340
Ser Cys Gly Asp Gly Tyr His Cys Cys Pro Gln Gly Phe His Cys Ser
                 95                 100                 105 gca gat ggg aaa tcc tgc ttc cag atg tca gat aac ccc ttg ggt gct      388
Ala Asp Gly Lys Ser Cys Phe Gln Met Ser Asp Asn Pro Leu Gly Ala
            110                 115                 120 gtc cag tgt cct ggg agc cag ttt gaa tgt cct gac tct gcc acc tgc      436
Val Gln Cys Pro Gly Ser Gln Phe Glu Cys Pro Asp Ser Ala Thr Cys
        125                 130                 135 tgc att atg gtt gat ggt tcg tgg gga tgt tgt ccc atg ccc cag gcc      484
Cys Ile Met Val Asp Gly Ser Trp Gly Cys Cys Pro Met Pro Gln Ala
    140                 145                 150 tct tgc tgt gaa gac aga gtg cat tgc tgt ccc cat ggg gcc tcc tgt      532
Ser Cys Cys Glu Asp Arg Val His Cys Cys Pro His Gly Ala Ser Cys
155                 160                 165                 170 gac ctg gtt cac aca cga tgc gtt tca ccc acg ggc acc cac acc cta      580
Asp Leu Val His Thr Arg Cys Val Ser Pro Thr Gly Thr His Thr Leu
                175                 180                 185 cta aag aag ttc cct gca caa aag acc aac agc gca gtg tct ttg cct      628
Leu Lys Lys Phe Pro Ala Gln Lys Thr Asn Ser Ala Val Ser Leu Pro
            190                 195                 200 ttt tct gtc gtg tgc cct gat gct aag acc cag tgt ccc gat gat tct      676
Phe Ser Val Val Cys Pro Asp Ala Lys Thr Gln Cys Pro Asp Asp Ser
        205                 210                 215 acc tgc tgt gag cta ccc act ggg aag tat ggc tgt tgt cca atg ccc      724
Thr Cys Cys Glu Leu Pro Thr Gly Lys Tyr Gly Cys Cys Pro Met Pro
    220                 225                 230
```

```
                                        -continued
aat gcc atc tgc tgt tcc gac cac ctg cac tgc tgc ccc cag gac act        772
Asn Ala Ile Cys Cys Ser Asp His Leu His Cys Cys Pro Gln Asp Thr
235             240                 245                 250 gta tgt gac ctg atc cag agt aag tgc cta tcc aag aac tac acc acg        820
Val Cys Asp Leu Ile Gln Ser Lys Cys Leu Ser Lys Asn Tyr Thr Thr
            255                 260                 265 gat ctc ctg acc aag ctg cct gga tac cca gtg aag gag gtg aag tgc        868
Asp Leu Leu Thr Lys Leu Pro Gly Tyr Pro Val Lys Glu Val Lys Cys
        270                 275                 280 gac atg gag gtg agc tgc cct gaa gga tat acc tgc tgc cgc ctc aac        916
Asp Met Glu Val Ser Cys Pro Glu Gly Tyr Thr Cys Cys Arg Leu Asn
    285                 290                 295 act ggg gcc tgg ggc tgc tgt cca ttt gcc aag gcc gtg tgt tgt gac        964
Thr Gly Ala Trp Gly Cys Cys Pro Phe Ala Lys Ala Val Cys Cys Asp
300                 305                 310 gat cac att cat tgc tgc ccg gca ggg ttt cag tgt cac aca gag aaa       1012
Asp His Ile His Cys Cys Pro Ala Gly Phe Gln Cys His Thr Glu Lys
315                 320                 325                 330 gga acc tgc gaa atg ggt atc ctc caa gta ggg tgg atg aag aag gtc       1060
Gly Thr Cys Glu Met Gly Ile Leu Gln Val Gly Trp Met Lys Lys Val
                335                 340                 345 ata gcc ccc ctc cgc ctg cca gac cca cag atc ttg aag agt gat aca       1108
Ile Ala Pro Leu Arg Leu Pro Asp Pro Gln Ile Leu Lys Ser Asp Thr
            350                 355                 360 cct tgt gat gac ttc act agg tgt cct aca aac aat acc tgc tgc aaa       1156
Pro Cys Asp Asp Phe Thr Arg Cys Pro Thr Asn Asn Thr Cys Cys Lys
        365                 370                 375 ctc aat tct ggg gac tgg ggc tgc tgt ccc atc cca gag gct gtc tgc       1204
Leu Asn Ser Gly Asp Trp Gly Cys Cys Pro Ile Pro Glu Ala Val Cys
    380                 385                 390 tgc tca gac aac cag cat tgc tgc cct cag ggc ttc aca tgt ctg gct       1252
Cys Ser Asp Asn Gln His Cys Cys Pro Gln Gly Phe Thr Cys Leu Ala
395                 400                 405                 410 cag ggg tac tgt cag aag gga gac aca atg gtg gct ggc ctg gag aag       1300
Gln Gly Tyr Cys Gln Lys Gly Asp Thr Met Val Ala Gly Leu Glu Lys
                415                 420                 425 ata cct gcc cgc cag aca acc ccg ctc caa att gga gat atc ggt tgt       1348
Ile Pro Ala Arg Gln Thr Thr Pro Leu Gln Ile Gly Asp Ile Gly Cys
            430                 435                 440 gac cag cat acc agc tgc cca gta ggg caa acc tgc tgc cca agc ctc       1396
Asp Gln His Thr Ser Cys Pro Val Gly Gln Thr Cys Cys Pro Ser Leu
        445                 450                 455 aag gga agt tgg gcc tgc tgc cag ctg ccc cat gct gtg tgc tgt gag       1444
Lys Gly Ser Trp Ala Cys Cys Gln Leu Pro His Ala Val Cys Cys Glu
    460                 465                 470 gac cgg cag cac tgt tgc ccg gcc ggg tac acc tgc aac gtg aag gcg       1492
Asp Arg Gln His Cys Cys Pro Ala Gly Tyr Thr Cys Asn Val Lys Ala
475                 480                 485                 490 agg acc tgt gag aag gat gtc gat ttt atc cag cct ccc gtg ctc ctg       1540
Arg Thr Cys Glu Lys Asp Val Asp Phe Ile Gln Pro Pro Val Leu Leu
                495                 500                 505 acc ctc ggc cct aag gtt ggg aat gtg gag tgt gga gaa ggg cat ttc       1588
Thr Leu Gly Pro Lys Val Gly Asn Val Glu Cys Gly Glu Gly His Phe
            510                 515                 520 tgc cat gat aac cag acc tgt tgt aaa gac agt gca gga gtc tgg gcc       1636
Cys His Asp Asn Gln Thr Cys Cys Lys Asp Ser Ala Gly Val Trp Ala
        525                 530                 535 tgc tgt ccc tac cta aag ggt gtc tgc tgt aga gat gga cgt cac tgt       1684
Cys Cys Pro Tyr Leu Lys Gly Val Cys Cys Arg Asp Gly Arg His Cys
    540                 545                 550
```

-continued

```
tgc ccc ggt ggc ttc cac tgt tca gcc agg gga acc aag tgt ttg cga    1732
Cys Pro Gly Gly Phe His Cys Ser Ala Arg Gly Thr Lys Cys Leu Arg
555                 560                 565                 570 aag aag att cct cgc tgg gac atg ttt ttg agg gat ccg gtc cca aga    1780
Lys Lys Ile Pro Arg Trp Asp Met Phe Leu Arg Asp Pro Val Pro Arg
            575                 580                 585 ccg cta ctg taaggaaggg ctacagactt aaggaactcc acagtcctgg            1829
Pro Leu Leu gaaccctgtt ccgagggtac ccactactca ggcctcccta gcgcctcctc ccctaacgtc  1889
tccccggcct actcatcctg agtcacccta tcaccatggg aggtggagcc tcaaactaaa  1949
accttctttt atggaaagaa ggctctggcc aaaagccccg tatcaaactg ccatttcttc  2009
cggtttctgt ggaccttgtg gccaggtgct cttcccgagc acaggtgtt ctgtgagctt   2069 gcttgtgtgt gtgtgcgcgt gtgcgtgtgt tgctccaata aagtttgtac gctttctgaa  2129
aaaaaaaa                                                           2137
```

<210> SEQ ID NO 2
<211> LENGTH: 589
<212> TYPE: PRT
<213> ORGANISM: Mouse epithelin/granulin

<400> SEQUENCE: 2

```
Met Trp Val Leu Met Ser Trp Leu Ala Phe Ala Ala Gly Leu Val Ala
  1               5                  10                  15

Gly Thr Gln Cys Pro Asp Gly Gln Phe Cys Pro Val Ala Cys Cys Leu
                 20                  25                  30

Asp Gln Gly Gly Ala Asn Tyr Ser Cys Cys Asn Pro Leu Leu Asp Thr
             35                  40                  45

Trp Pro Arg Ile Thr Ser His Leu Asp Gly Ser Cys Gln Thr His
         50                  55                  60

Gly His Cys Pro Ala Gly Tyr Ser Cys Leu Leu Thr Val Ser Gly Thr
 65                  70                  75                  80

Ser Ser Cys Cys Pro Phe Ser Lys Gly Val Ser Cys Gly Asp Gly Tyr
                 85                  90                  95

His Cys Cys Pro Gln Gly Phe His Cys Ser Ala Asp Gly Lys Ser Cys
                100                 105                 110

Phe Gln Met Ser Asp Asn Pro Leu Gly Ala Val Gln Cys Pro Gly Ser
            115                 120                 125

Gln Phe Glu Cys Pro Asp Ser Ala Thr Cys Cys Ile Met Val Asp Gly
        130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Ser Ala Val Ser Leu Pro Phe Ser Val Val Cys Pro
        195                 200                 205

Asp Ala Lys Thr Gln Cys Pro Asp Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255
```

-continued

```
Ser Lys Cys Leu Ser Lys Asn Tyr Thr Thr Asp Leu Leu Thr Lys Leu
        260                 265                 270

Pro Gly Tyr Pro Val Lys Glu Val Lys Cys Asp Met Glu Val Ser Cys
            275                 280                 285

Pro Glu Gly Tyr Thr Cys Arg Leu Asn Thr Gly Ala Trp Gly Cys
        290                 295                 300

Cys Pro Phe Ala Lys Ala Val Cys Cys Asp Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Gly Trp Met Lys Lys Val Ile Ala Pro Leu Arg Leu
        340                 345                 350

Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
                420                 425                 430

Thr Pro Leu Gln Ile Gly Asp Ile Gly Cys Asp Gln His Thr Ser Cys
        435                 440                 445

Pro Val Gly Gln Thr Cys Cys Pro Ser Leu Lys Gly Ser Trp Ala Cys
        450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
                485                 490                 495

Val Asp Phe Ile Gln Pro Pro Val Leu Leu Thr Leu Gly Pro Lys Val
                500                 505                 510

Gly Asn Val Glu Cys Gly Glu Gly His Phe Cys His Asp Asn Gln Thr
        515                 520                 525

Cys Cys Lys Asp Ser Ala Gly Val Trp Ala Cys Cys Pro Tyr Leu Lys
        530                 535                 540

Gly Val Cys Cys Arg Asp Gly Arg His Cys Cys Pro Gly Gly Phe His
545                 550                 555                 560

Cys Ser Ala Arg Gly Thr Lys Cys Leu Arg Lys Lys Ile Pro Arg Trp
                565                 570                 575

Asp Met Phe Leu Arg Asp Pro Val Pro Arg Pro Leu Leu
        580                 585
```

<210> SEQ ID NO 3
<211> LENGTH: 19
<212> TYPE: PRT
<213> ORGANISM: mouse granulin
<220> FEATURE:
<221> NAME/KEY: PEPTIDE
<222> LOCATION: (1)..(19)
<223> OTHER INFORMATION: Internal peptide of mouse GP88 used to raise
      the antisera against the GP88 used in the immunoaffinity step.

```
<400> SEQUENCE: 3

Lys Lys Val Ile Ala Pro Arg Arg Leu Pro Asp Pro Gln Ile Leu Lys
 1               5                   10                  15

Ser Asp Thr

<210> SEQ ID NO 4
<211> LENGTH: 12
<212> TYPE: PRT
<213> ORGANISM: mouse granulin
<220> FEATURE:
<221> NAME/KEY: PEPTIDE
<222> LOCATION: (1)..(12)
<223> OTHER INFORMATION: Internal peptide of mouse GP88 used to raise
      the antisera against the GP88 used in the immunoaffinity step.

<400> SEQUENCE: 4

Pro Asp Ala Lys Thr Gln Cys Pro Asp Asp Ser Thr
 1               5                   10

<210> SEQ ID NO 5
<211> LENGTH: 14
<212> TYPE: PRT
<213> ORGANISM: mouse granulin
<220> FEATURE:
<221> NAME/KEY: PEPTIDE
<222> LOCATION: (1)..(14)
<223> OTHER INFORMATION: Internal peptide of mouse GP88 used to raise
      the antisera against the GP88 used in the immunoaffinity step.

<400> SEQUENCE: 5

Ser Ala Arg Gly Thr Lys Cys Leu Arg Lys Lys Ile Pro Arg
 1               5                   10

<210> SEQ ID NO 6
<211> LENGTH: 19
<212> TYPE: PRT
<213> ORGANISM: Human granulin
<220> FEATURE:
<221> NAME/KEY: PEPTIDE
<222> LOCATION: (1)..(19)
<223> OTHER INFORMATION: Internal peptide of human GP88 used to develop
      neutralizing anti-human GP88 monoclonal antibody.

<400> SEQUENCE: 6

Glu Lys Ala Pro Ala His Leu Ser Leu Pro Asp Pro Gln Ala Leu Lys
 1               5                   10                  15

Arg Asp Val

<210> SEQ ID NO 7
<211> LENGTH: 14
<212> TYPE: PRT
<213> ORGANISM: Human granulin
<220> FEATURE:
<221> NAME/KEY: PEPTIDE
<222> LOCATION: (1)..(14)
<223> OTHER INFORMATION: Internal peptide of human GP88 used to develop
      neutralizing anti-human GP88 monoclonal antibody.

<400> SEQUENCE: 7

Ala Arg Arg Gly Thr Lys Cys Leu Arg Arg Glu Ala Pro Arg
 1               5                   10

<210> SEQ ID NO 8
<211> LENGTH: 24
<212> TYPE: DNA
<213> ORGANISM: mammalian
<220> FEATURE:
```

```
<221> NAME/KEY: primer
<222> LOCATION: (1)..(24)
<223> OTHER INFORMATION: Internal peptide of CMV promoter used as PCR
      primer.

<400> SEQUENCE: 8
cctacttggc agtacatcta cgta                                            24

<210> SEQ ID NO 9
<211> LENGTH: 27
<212> TYPE: DNA
<213> ORGANISM: mammalian
<220> FEATURE:
<221> NAME/KEY: primer
<222> LOCATION: (1)..(27)
<223> OTHER INFORMATION: GP88 cDNA start codon used as oligonucleotide
      PCR primer.

<400> SEQUENCE: 9
cgagaattca ggcagaccat gtgggtc                                         27

<210> SEQ ID NO 10
<211> LENGTH: 27
<212> TYPE: DNA
<213> ORGANISM: mammalian
<220> FEATURE:
<221> NAME/KEY: primer
<222> LOCATION: (1)..(27)
<223> OTHER INFORMATION: Antisense primer oligonucleotide primer

<400> SEQUENCE: 10
cgagaattca ggcagaccat gtgggtc                                         27

<210> SEQ ID NO 11
<211> LENGTH: 23
<212> TYPE: DNA
<213> ORGANISM: mammalian
<220> FEATURE:
<221> NAME/KEY: primer
<222> LOCATION: (1)..(23)
<223> OTHER INFORMATION: Antisense primer oligonucleotide primer

<400> SEQUENCE: 11
ctgacggttc actaaacgag ctc                                             23

<210> SEQ ID NO 12
<211> LENGTH: 25
<212> TYPE: DNA
<213> ORGANISM: mammalian
<220> FEATURE:
<221> NAME/KEY: primer
<222> LOCATION: (1)..(25)
<223> OTHER INFORMATION: primer

<400> SEQUENCE: 12
ggatccacgg agttgttacc tgatc                                           25

<210> SEQ ID NO 13
<211> LENGTH: 25
<212> TYPE: DNA
<213> ORGANISM: mammalian
<220> FEATURE:
<221> NAME/KEY: primer
<222> LOCATION: (1)..(25)
<223> OTHER INFORMATION: oligonucleotide PCR primer

<400> SEQUENCE: 13
gaattcgcag gcagaccatg tggac                                           25
```

```
<210> SEQ ID NO 14
<211> LENGTH: 21
<212> TYPE: DNA
<213> ORGANISM: mammalian
<220> FEATURE:
<221> NAME/KEY: primer
<222> LOCATION: (1)..(21)
<223> OTHER INFORMATION: Antisense oligonucleotide to human GP88

<400> SEQUENCE: 14
gggtccacat ggtctgcctg c                                              21

<210> SEQ ID NO 15
<211> LENGTH: 24
<212> TYPE: DNA
<213> ORGANISM: mammalian
<220> FEATURE:
<221> NAME/KEY: primer
<222> LOCATION: (1)..(24)
<223> OTHER INFORMATION: Antisense oligonucleotide to human GP88

<400> SEQUENCE: 15
gccaccagcc ctgctgttaa ggcc                                           24

<210> SEQ ID NO 16
<211> LENGTH: 2095
<212> TYPE: DNA
<213> ORGANISM: Human GP88 cDNA
<220> FEATURE:
<221> NAME/KEY: CDS
<222> LOCATION: (13)..(1791)
<223> OTHER INFORMATION: Nucleotide sequence of human granulin/epithelin
      precursor (human GP88).  Human Granulin Genebank
      M75161.

<400> SEQUENCE: 16
```

| | | | | | | | | | | | | | |
|---|---|---|---|---|---|---|---|---|---|---|---|---|---|
| cgcaggcaga cc atg tgg acc ctg gtg agc tgg gtg gcc tta aca gca ggg | | | | | | | | | | | | | 51 |
| | Met | Trp | Thr | Leu | Val | Ser | Trp | Val | Ala | Leu | Thr | Ala | Gly |
| | 1 | | | | 5 | | | | | 10 | | | |

```
ctg gtg gct gga acg cgg tgc cca gat ggt cag ttc tgc cct gtg gcc    99
Leu Val Ala Gly Thr Arg Cys Pro Asp Gly Gln Phe Cys Pro Val Ala
 15                  20                  25 tgc tgc ctg gac ccc gga gga gcc agc tac agc tgc tgc cgt ccc ctt   147
Cys Cys Leu Asp Pro Gly Gly Ala Ser Tyr Ser Cys Cys Arg Pro Leu
 30                  35                  40                  45 ctg gac aaa tgg ccc aca aca ctg agc agg cat ctg ggt ggc ccc tgc   195
Leu Asp Lys Trp Pro Thr Thr Leu Ser Arg His Leu Gly Gly Pro Cys
                 50                  55                  60 cag gtt gat gcc cac tgc tct gcc ggc cac tcc tgc atc ttt acc gtc   243
Gln Val Asp Ala His Cys Ser Ala Gly His Ser Cys Ile Phe Thr Val
             65                  70                  75 tca ggg act tcc agt tgc tgc ccc ttc cca gag gcc gtg gca tgc ggg   291
Ser Gly Thr Ser Ser Cys Cys Pro Phe Pro Glu Ala Val Ala Cys Gly
         80                  85                  90 gat ggc cat cac tgc tgc cca cgg ggc ttc cac tgc agt gca gac ggg   339
Asp Gly His His Cys Cys Pro Arg Gly Phe His Cys Ser Ala Asp Gly
     95                 100                 105 cga tcc tgc ttc caa aga tca ggt aac aac tcc gtg ggt gcc atc cag   387
Arg Ser Cys Phe Gln Arg Ser Gly Asn Asn Ser Val Gly Ala Ile Gln
110                 115                 120                 125 tgc cct gat agt cag ttc gaa tgc ccg gac ttc tcc acg tgc tgt gtt   435
Cys Pro Asp Ser Gln Phe Glu Cys Pro Asp Phe Ser Thr Cys Cys Val
                130                 135                 140
```

```
atg gtc gat ggc tcc tgg ggg tgc tgc ccc atg ccc cag gct tcc tgc       483
Met Val Asp Gly Ser Trp Gly Cys Cys Pro Met Pro Gln Ala Ser Cys
        145                 150                 155 tgt gaa gac agg gtg cac tgc tgt ccg cac ggt gcc ttc tgc gac ctg       531
Cys Glu Asp Arg Val His Cys Cys Pro His Gly Ala Phe Cys Asp Leu
        160                 165                 170 gtt cac acc cgc tgc atc aca ccc acg ggc acc cac ccc ctg gca aag       579
Val His Thr Arg Cys Ile Thr Pro Thr Gly Thr His Pro Leu Ala Lys
        175                 180                 185 aag ctc cct gcc cag agg act aac agg gca gtg gcc ttg tcc agc tcg       627
Lys Leu Pro Ala Gln Arg Thr Asn Arg Ala Val Ala Leu Ser Ser Ser
190                 195                 200                 205 gtc atg tgt ccg gac gca cgg tcc cgg tgc cct gat ggt tct acc tgc       675
Val Met Cys Pro Asp Ala Arg Ser Arg Cys Pro Asp Gly Ser Thr Cys
                210                 215                 220 tgt gag ctg ccc agt ggg aag tat ggc tgc tgc cca atg ccc aac gcc       723
Cys Glu Leu Pro Ser Gly Lys Tyr Gly Cys Cys Pro Met Pro Asn Ala
                225                 230                 235 acc tgc tgc tcc gat cac ctg cac tgc tgc ccc caa gac act gtg tgt       771
Thr Cys Cys Ser Asp His Leu His Cys Cys Pro Gln Asp Thr Val Cys
                240                 245                 250 gac ctg atc cag agt aag tgc ctc tcc aag gag aac gct acc acg gac       819
Asp Leu Ile Gln Ser Lys Cys Leu Ser Lys Glu Asn Ala Thr Thr Asp
        255                 260                 265 ctc ctc act aag ctg cct gcg cac aca gtg ggc gat gtg aaa tgt gac       867
Leu Leu Thr Lys Leu Pro Ala His Thr Val Gly Asp Val Lys Cys Asp
270                 275                 280                 285 atg gag gtg agc tgc cca gat ggc tat acc tgc tgc cgt cta cag tcg       915
Met Glu Val Ser Cys Pro Asp Gly Tyr Thr Cys Cys Arg Leu Gln Ser
                290                 295                 300 ggg gcc tgg ggc tgc tgc cct ttt acc cag gct gtg tgc tgt gag gac       963
Gly Ala Trp Gly Cys Cys Pro Phe Thr Gln Ala Val Cys Cys Glu Asp
                305                 310                 315 cac ata cac tgc tgt ccc gcg ggg ttt acg tgt gac acg cag aag ggt      1011
His Ile His Cys Cys Pro Ala Gly Phe Thr Cys Asp Thr Gln Lys Gly
                320                 325                 330 acc tgt gaa cag ggg ccc cac cag gtg ccc tgg atg gag aag gcc cca      1059
Thr Cys Glu Gln Gly Pro His Gln Val Pro Trp Met Glu Lys Ala Pro
335                 340                 345 gct cac ctc agc ctg cca gac cca caa gcc ttg aag aga gat gtc ccc      1107
Ala His Leu Ser Leu Pro Asp Pro Gln Ala Leu Lys Arg Asp Val Pro
350                 355                 360                 365 tgt gat aat gtc agc agc tgt ccc tcc tcc gat acc tgc tgc caa ctc      1155
Cys Asp Asn Val Ser Ser Cys Pro Ser Ser Asp Thr Cys Cys Gln Leu
                370                 375                 380 acg tct ggg gag tgg ggc tgc tgt cca atc cca gag gct gtc tgc tgc      1203
Thr Ser Gly Glu Trp Gly Cys Cys Pro Ile Pro Glu Ala Val Cys Cys
                385                 390                 395 tcg gac cac cag cac tgc tgc ccc cag cga tac acg tgt gta gct gag      1251
Ser Asp His Gln His Cys Cys Pro Gln Arg Tyr Thr Cys Val Ala Glu
        400                 405                 410 ggg cag tgt cag cga gga agc gag atc gtg gct gga ctg gag aag atg      1299
Gly Gln Cys Gln Arg Gly Ser Glu Ile Val Ala Gly Leu Glu Lys Met
        415                 420                 425 cct gcc cgc cgc ggt tcc tta tcc cac ccc aga gac atc ggc tgt gac      1347
Pro Ala Arg Arg Gly Ser Leu Ser His Pro Arg Asp Ile Gly Cys Asp
430                 435                 440                 445 cag cac acc agc tgc ccg gtg ggc gga acc tgc tgc ccg agc cag ggt      1395
Gln His Thr Ser Cys Pro Val Gly Gly Thr Cys Cys Pro Ser Gln Gly
                450                 455                 460
```

-continued

```
ggg agc tgg gcc tgc tgc cag ttg ccc cat gct gtg tgc tgc gag gat    1443
Gly Ser Trp Ala Cys Cys Gln Leu Pro His Ala Val Cys Cys Glu Asp
        465                 470                 475 cgc cag cac tgc tgc ccg gct ggc tac acc tgc aac gtg aag gct cga    1491
Arg Gln His Cys Cys Pro Ala Gly Tyr Thr Cys Asn Val Lys Ala Arg
480                 485                 490 tcc tgc gag aag gaa gtg gtc tct gcc cag cct gcc acc ttc ctg gcc    1539
Ser Cys Glu Lys Glu Val Val Ser Ala Gln Pro Ala Thr Phe Leu Ala
    495                 500                 505 cgt agc cct cac gtg ggt gtg aag gac gtg gag tgt ggg gaa gga cac    1587
Arg Ser Pro His Val Gly Val Lys Asp Val Glu Cys Gly Glu Gly His
510                 515                 520                 525 ttc tgc cat gat aac cag acc tgc tgc cga gac aac cga cag ggc tgg    1635
Phe Cys His Asp Asn Gln Thr Cys Cys Arg Asp Asn Arg Gln Gly Trp
                530                 535                 540 gcc tgc tgt ccc tac gcc cag ggc gtc tgt tgt gct gat cgg cgc cac    1683
Ala Cys Cys Pro Tyr Ala Gln Gly Val Cys Cys Ala Asp Arg Arg His
                545                 550                 555 tgc tgt cct gct ggc ttc cgc tgc gca cgc agg ggt acc aag tgt ttg    1731
Cys Cys Pro Ala Gly Phe Arg Cys Ala Arg Arg Gly Thr Lys Cys Leu
            560                 565                 570 cgc agg gag gcc ccg cgc tgg gac gcc cct ttg agg gac cca gcc ttg    1779
Arg Arg Glu Ala Pro Arg Trp Asp Ala Pro Leu Arg Asp Pro Ala Leu
575                 580                 585 aga cag ctg ctg tgagggacag tactgaagac tctgcagccc tcgggacccc        1831
Arg Gln Leu Leu
590 actcggaggg tgccctctgc tcaggcctcc ctagcacctc ccctaaccaa aattctccct  1891 ggacccccatt ctgagctccc catcaccatg ggaggtgggg cctcaatcta aggcccttcc 1951 ctgtcagaag ggggttgagg caaaagccca ttacaagctg ccatcccctc cccgtttcag  2011 tggaccctgt ggccaggtgc ttttccctat ccacaggggt gtttgtgtgt tgggtgtgct  2071 ttcaataaag tttgtcactt tctt                                        2095

<210> SEQ ID NO 17
<211> LENGTH: 593
<212> TYPE: PRT
<213> ORGANISM: Human GP88 cDNA

<400> SEQUENCE: 17

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125
```

-continued

```
Ser Gln Phe Glu Cys Pro Asp Phe Ser Thr Cys Cys Val Met Val Asp
    130                 135                 140
Gly Ser Trp Gly Cys Cys Pro Met Pro Gln Ala Ser Cys Cys Glu Asp
145                 150                 155                 160
Arg Val His Cys Cys Pro His Gly Ala Phe Cys Asp Leu Val His Thr
                165                 170                 175
Arg Cys Ile Thr Pro Thr Gly Thr His Pro Leu Ala Lys Lys Leu Pro
            180                 185                 190
Ala Gln Arg Thr Asn Arg Ala Val Ala Leu Ser Ser Val Met Cys
        195                 200                 205
Pro Asp Ala Arg Ser Arg Cys Pro Asp Gly Ser Thr Cys Cys Glu Leu
    210                 215                 220
Pro Ser Gly Lys Tyr Gly Cys Cys Pro Met Pro Asn Ala Thr Cys Cys
225                 230                 235                 240
Ser Asp His Leu His Cys Cys Pro Gln Asp Thr Val Cys Asp Leu Ile
                245                 250                 255
Gln Ser Lys Cys Leu Ser Lys Glu Asn Ala Thr Thr Asp Leu Leu Thr
            260                 265                 270
Lys Leu Pro Ala His Thr Val Gly Asp Val Lys Cys Asp Met Glu Val
        275                 280                 285
Ser Cys Pro Asp Gly Tyr Thr Cys Cys Arg Leu Gln Ser Gly Ala Trp
    290                 295                 300
Gly Cys Cys Pro Phe Thr Gln Ala Val Cys Cys Glu Asp His Ile His
305                 310                 315                 320
Cys Cys Pro Ala Gly Phe Thr Cys Asp Thr Gln Lys Gly Thr Cys Glu
                325                 330                 335
Gln Gly Pro His Gln Val Pro Trp Met Glu Lys Ala Pro Ala His Leu
            340                 345                 350
Ser Leu Pro Asp Pro Gln Ala Leu Lys Arg Asp Val Pro Cys Asp Asn
        355                 360                 365
Val Ser Ser Cys Pro Ser Ser Asp Thr Cys Cys Gln Leu Thr Ser Gly
    370                 375                 380
Glu Trp Gly Cys Cys Pro Ile Pro Glu Ala Val Cys Cys Ser Asp His
385                 390                 395                 400
Gln His Cys Cys Pro Gln Arg Tyr Thr Cys Val Ala Glu Gly Gln Cys
                405                 410                 415
Gln Arg Gly Ser Glu Ile Val Ala Gly Leu Glu Lys Met Pro Ala Arg
            420                 425                 430
Arg Gly Ser Leu Ser His Pro Arg Asp Ile Gly Cys Asp Gln His Thr
        435                 440                 445
Ser Cys Pro Val Gly Gly Thr Cys Cys Pro Ser Gln Gly Gly Ser Trp
    450                 455                 460
Ala Cys Cys Gln Leu Pro His Ala Val Cys Cys Glu Asp Arg Gln His
465                 470                 475                 480
Cys Cys Pro Ala Gly Tyr Thr Cys Asn Val Lys Ala Arg Ser Cys Glu
                485                 490                 495
Lys Glu Val Val Ser Ala Gln Pro Ala Thr Phe Leu Ala Arg Ser Pro
            500                 505                 510
His Val Gly Val Lys Asp Val Glu Cys Gly Glu Gly His Phe Cys His
        515                 520                 525
Asp Asn Gln Thr Cys Cys Arg Asp Asn Arg Gln Gly Trp Ala Cys Cys
    530                 535                 540
```

```
                                              -continued

Pro Tyr Ala Gln Gly Val Cys Cys Ala Asp Arg Arg His Cys Cys Pro
545                 550                 555                 560

Ala Gly Phe Arg Cys Ala Arg Arg Gly Thr Lys Cys Leu Arg Arg Glu
                565                 570                 575

Ala Pro Arg Trp Asp Ala Pro Leu Arg Asp Pro Ala Leu Arg Gln Leu
                580                 585                 590

Leu
```

88KDA TUMORIGENIC GROWTH FACTOR AND ANTAGONISTS

This application is a divisional of application, U.S. Ser. No. 08/991,862 filed Dec. 16, 1997, now U.S. Pat. No. 6,309,826, the entirety of which is incorporated herein by reference.

FIELD OF THE INVENTION

This invention relates to cell biology, physiology and medicine, and concerns an 88 kDa glycoprotein growth factor ("GP88") and compositions and methods which affect the expression and biological activity of GP88. These compositions and methods are useful for diagnosis and treatment of diseases including cancer.

REFERENCE

Several publications are referenced herein by Arabic numerals within parenthesis. Full citations for these references may be found at the end of the specification immediately preceding the claims.

The proliferation and differentiation of cells in multicellular organisms is subject to a highly regulated process (1). A distinguishing feature of cancer cells is the absence of control over this process; proliferation and differentiation become deregulated resulting in uncontrolled growth. Significant research efforts have been directed toward better understanding this difference between normal and tumor cells. One area of research focus is growth factors and, more specifically, autocrine growth stimulation.

Growth factors are polypeptides which carry messages to cells concerning growth, differentiation, migration and gene expression (2). Typically, growth factors are produced in one cell and act on another cell to stimulate proliferation However, certain malignant cells, in culture, demonstrate a greater or absolute reliance on an autocrine growth mechanism (3). Malignant cells which observe this autocrine behavior circumvent the regulation of growth factor production by other cells and are therefore unregulated in their growth.

Study of autocrine growth control advances understanding of cell growth mechanisms and leads to important advances in the diagnosis and treatment of cancer. Toward this end, a number of growth factors have been studied, including insulin-like growth factors ("IGF1" and "IGF2"), gastrin-releasing peptide ("GRP"), transforming growth factors alpha and beta ("TGF-α" and "TGF-β"), and epidermal growth factor ("EGF").

The present invention is directed to a recently discovered growth factor. This growth factor was first discovered in the culture medium of highly tumorigenic "PC cells," an insulin-independent variant isolated from the teratoma derived adipogenic cell line 1246. This growth factor is referred to herein as "GP88." GP88 has been purified and structurally charactexized (4). Amino acid sequencing of GP88 indicates that GP88 has amino acid sequence similarities with the mouse granulin/epithelin precursor.

Granulins/epithelins ("grn/epi") are 6 kDa polypeptides and belong to a novel family of double cysteine rich polypeptides (5, 6). U.S. Pat. No. 5,416,192 (Shoyab et al.) is directed to 6 kDa epithelins, particularly epithelin 1 and epithelin 2. According to Shoyab, both epithelins are encoded by a common 63.5 kDa precursor, which is processed into smaller forms as soon as it is synthesized, so that the only natural products found in biological samples are the 6 kDa forms. Shoyab et al. teaches that the epithelin precursor is biologically inactive.

Contrary to the teachings of Shoyab et al., the inventor's laboratory has demonstrated that the precursor is not always processed as soon as it is synthesized. Studies, conducted in part by this inventor, have demonstrated that the precursor (i.e., GP88) is in fact secreted as an 88 kDa glycoprotein with an N-linked carbohydrate moiety of 20 kDa (4). Analysis of the N-terminal sequence of GP88 indicates that GP88 starts at amino acid 17 of the grn/epi precursor, demonstrating that the first 17 amino acids from the protein sequence deduced from the precursor cDNA correspond to a signal peptide compatible with targeting for membrane localization or for secretion (4).

Also in contrast to the teachings of Shoyab et al., GP88 is biologically active and has growth promoting activity, particularly as an autocrine growth factor for the producer cells.

SUMMARY OF INVENTION

The inventor has now unexpectedly discovered that a glycoprotein (GP88), which is expressed in a tightly regulated fashion in normal cells, is overexpressed and unregulated in highly tumorigenic cells derived from the normal cells, that GP88 acts as a stringently required growth stimulator for the tumorigenic cells and that inhibition of GP88 expression or action in the tumorigenic cells results in an inhibition of the tumorigenic properties of the overproducing cells.

It is an object of this invention to provide GP88 antagonizing compositions capable of inhibiting the expression or activity of GP88.

A further object of the invention is to provide methods for treating diseases associated with a defect in GP88 quantity or activity such as but not limited to cancer in mice or humans.

Another object of the invention is to provide methods for determining the susceptibility of a subject to diseases associated with a defect in GP88 expression or action.

Yet another object of the invention is to provide methods for measuring susceptibility to GP88 antagonizing therapy.

Yet another object of the invention is to provide methods, reagents, and kits for the in vitro and in vivo detection of GP88 and tumorigenic activity in cells.

Additional objects and advantages of the invention will be set forth in part in the description that follows, and in part will be obvious from the description, or may be learned by the practice of the invention.

To achieve the objects and in accordance with the purpose of the invention, as embodied and properly described herein, the present invention provides compositions for diagnosis and treatment of diseases such as but not limited to cancer in which cells exhibit an altered expression of GP88 or altered response to GP88.

Use of the term "altered expression" herein means increased expression or overexpression of GP88 by a factor of at least two-fold, and at times by a factor of 10 or more, based on the level of mRNA or protein as compared to corresponding normal cells or surrounding peripheral cells. The term "altered expression" also means expression which became unregulated or constitutive without being necessarily elevated. Use of the terms increased or altered "response" to GP88 means a condition wherein increase in any of the biological functions (e.g., growth, differentiation, viral infectivity) conferred by GP88 results in the same or equivalent condition as altered expression of GP88.

Use of the term "GP88" herein means epithelin/granulin precursor in cell extracts and extracellular fluids, and is intended to include not only GP88 according to the amino acid sequences included in FIG. 8 or 9, which are of mouse and human origins, but also GP88 of other species. In addition, the term also includes functional derivatives thereof having additional components such as a carbohydrate moiety including a glycoprotein or other modified structures.

Also intended by the term GP88 is any polypeptide fragment having at least 10 amino-acids present in the above mentioned sequences. Sequences of this length are useful as antigens and for making immunogenic conjugates with carriers for the production of antibodies specific for various epitopes of the entire protein. Such polypeptides are useful in screening such antibodies and in the methods directed to detection of GP88 in biological fluids. It is well known in the art that peptides are useful in generation of antibodies to larger proteins (7). In one embodiment of this invention, it is shown that peptides from 12–19 amino-acids in length have been successfully used to develop antibodies that recognize the full length GP88.

The polypeptide of this invention may exist covalently or non-covalently bound to another molecule. For example, it may be fused to one or more other polypeptides via one or more peptide bonds such as glutathione transferase, polyhistidine, or myc tag.

The polypeptide is sufficiently large to comprise an antigenetically distinct determinant or epitope which can be used as an immunogen to reproduce or test antibodies against GP88 or a functional derivative thereof One embodiment includes the polypeptide substantially free of other mammalian peptides. GP88 of the present invention can be biochemically or immunochemically purified from cells, tissues or a biological fluid. Alternatively, the polypeptide can be produced by recombinant means in a prokaryotic or eukaryotic expression system and host cells.

"Substantially free of other mammalian polypeptides" reflects the fact that the polypeptide can be synthesized in a prokaryotic or a non-mammalian or mammalian eukaryotic organism, if desired. Alternatively, methods are well known for the synthesis of polypeptides of desired sequences by chemical synthesis on solid phase supports and their subsequent separation from the support. Alternatively, the protein can be purified from tissues or fluids of mammals where it naturally occurs so that it is at least 90% pure (on a weight basis) or even 99% pure, if desired, of other mammalian polypeptides, and is therefore substantially free from them. This can be achieved by subjecting the tissue extracts or fluids to standard protein purification such as on immunoabsorbants bearing antibodies reactive against the protein. One embodiment of the present invention describes purification methods for the purification of naturally occurring GP88 and of recombinant GP88 expressed in baculovirus infected insect cells. Alternatively, purification from such tissues or fluids can be achieved by a combination of standard methods such as but not limited to the ones described in reference (4).

As an alternative to a native purified or recombinant glycoprotein or polypeptide, "GP88" is intended to also include functional derivatives. By functional derivative is meant a "fragment," "variant," "analog," or "chemical derivative" of the protein or glycoprotein as defined below. A functional derivative retains at least a portion of the function of the full length GP88 which permits its utility in accordance with the present invention.

A "fragment" of GP88 refers to any subset of the molecule that is a shorter peptide. This corresponds for example but is not limited to regions such as K19T and S14R for mouse GP88, and E19V and A14R (equivalent to murine K19T and S14R, respectively) for human GP88.

A "variant" of GP88 refers to a molecule substantially similar to either the entire peptide or a fragment thereof. Variant peptides may be prepared by direct chemical synthesis of the variant peptide using methods known in the art. Alternatively, amino acid sequence variants of the peptide can be prepared by modifying the DNA which encodes the synthesized protein or peptide. Such variants include, for example, deletions, insertions, or substitutions of residues within the amino-acid sequence of GP88. Any combination of deletion, insertion, and substitution may also be made to arrive at the final construct, provided the final construct possesses the desired activity. The mutation that will be made in the DNA encoding the variant peptide must not alter the reading frame and preferably will not create complementary regions that could produce secondary mRNA structures. At the genetic level these variants are prepared by site directed mutagenesis (8) of nucleotides in the DNA encoding the peptide molecule thereby producing DNA encoding the variant, and thereafter expressing the DNA in recombinant cell culture. The variant typically exhibits the same qualitative biological activity as the nonvariant peptide.

An "analog" of GP88 protein refers to a non-natural molecule substantially similar to either the entire molecule or a fragment thereof.

A "chemical derivative" contains additional chemical moieties not normally a part of the peptide or protein. Covalent modifications of the peptide are also included within the scope of this invention. Such modifications may be introduced into the molecule by reacting targeted amino-acid residues of the peptide with an organic derivatizing agent that is capable of reacting with selected side chains or terminal amino-acid residues. Most commonly derivatized residues are cysteinyl, histidyl, lysinyl, arginyl, tyrosyl, glutaminyl, asparaginyl and amino terminal residues. Hydroxylation of proline and lysine, phosphorylation of hydroxyl groups of seryl and threonyl residues, methylation of the alpha-amino groups of lysine, histidine, and histidine side chains, acetylation of the N-terminal amine and amidation of the C-terminal carboxylic groups. Such derivatized moieties may improve the solubility, absorption, biological half life and the like. The moieties may also elimite or attenuate any undesirable side effect of the protein and the like. In addition, derivatization with bifunctional agents is useful for cross-lkig the peptide to water insoluble support matrices or to other macromolecular carriers. Commonly used cross-linking agents include glutaraldehyde, N-hydroxysuccinimide esters, homobifunctional imidoesters, 1,1-bis(-diazoloacetyl)-2-phenylethane, and bifunctional maleimides. Derivatizing agents such as methyl-3-[9p-azidophenyl)]dithiopropioimidate yield photoactivatable intermediates that are capable of forming crosslinks in the presence of light. Alternatively, reactive water-insoluble matrices such as cyanogen bromide activated carbohydrates and the reactive substrates described in U.S. Pat. Nos. 3,969,287 and 3,691,016 may be employed for protein immobilization.

Use of the term GP88 "antagonizing agents" herein means any composition that inhibits or blocks GP88 expression, production or secretion, or any composition that inhibits or blocks the biological activity of GP88. This can be achieved by any mode of action such as but not limited to the following:

(A) GP88 antagonizing agents include any reagent or molecule inhibiting GP88 expression or production including but not limited to:
  (1) antisense GP88 DNA or RNA molecules that inhibit GP88 expression by inhibiting GP88 translation;
  (2) reagents (hormones, growth factors, small molecules) that inhibit GP88 mRNA and/or protein expression at the transcriptional, translational or post-transaltional levels;
  (3) factors, reagents or hormones that inhibit GP88 secretion;
(B) GP88 antagonizing agents also include any reagent or molecule that will inhibit GP88 action or biological activity such as but not limited to:
  (1) neutralizing antibodies to GP88 that bind the protein and prevent it from exerting its biological activity;
  (2) antibodies to the GP88 receptor that prevent GP88 from binding to its receptor and from exerting its biological activity;
  (3) competitive inhibitors of GP88 binding to its receptors;
  (4) inhibitors of GP88 signaling pathways.

Specific examples presented herein provide a description of preferred embodiments, particularly the use of neutrazing antibodies to inhibit GP88 biological action and the growth of the highly tumorigenic PC cells; the use of antisense GP88 cDNA and antisense GP88 oligonucleotides to inhibit GP88 expression leading to inhibition of the tumorigenic properties of the PC cells; characterization of GP88 receptors on cell surfaces of several cell lines including the mammary epithelial cell line C57MG, the 1246 and PC cell lines and the mink lung epithelial cell line CCL64.

In one embodiment of the invention, the GP88 antagonizing agents are antisense oligonucleotides to GP88. The antisense oligonucleotides preferably inhibit GP88 expression by inhibiting translation of the GP88 protein.

Alternatively, such a composition may comprise reagents, factors or hormones that inhibit GP88 expression by regulating GP88 gene transcriptional activity. Such a composition may comprise reagents, factors or hormones that inhibit GP88 post-translational modification and its secretion. Such a composition may comprise reagents that act as GP88 antagonists that block GP88 activity by competing with GP88 for binding to GP88 cell surface receptors. Alternatively, such a composition may comprise factors or reagents that inhibit the signaling pathway transduced by GP88 once binding to its receptors on diseased cells.

Alternatively, the composition may comprise reagents that block GP88 action such as an antibody specific to GP88 that neutralizes its biological activity, or an antibody to the GP88 receptor that blocks its activity.

The antibodies of the invention (neutralizing and others) are preferably used as a treatment for cancer or other diseases in cells which exhibit an increased expression of GP88. By the term "neutralizing" it shall be understood that the antibody has the ability to inhibit or block the normal biological activity of GP88, including GP88's ability to stimulate cell proliferation or to induce tumor growth in experimental animals and in humans. An effective amount of anti-GP88 antibody is administered to an animal, including humans, by various routes. In an alternative embodiment, the anti-GP88 antibody is used as a diagnostic to detect cells which exhibit an altered (increased) expression of GP88 as occurring in diseases such as but not limited to cancers, and to identify diseased cells whose growth is dependent on GP88 and which will respond to GP88 antagonizing therapy.

In yet another embodiment, the anti-GP88 antibody is used to deliver compounds such as cytotoxic factors or antisense oligonucleotides to cells expressing or responsive to GP88.

The antisense oligonucleotides of the invention are also used as a treatment for cancer in cells which exhibit an increased expression of GP88. An effective amount of the antisense oligonucleotide is administered to an animal, including humans, by various routes.

The present invention also provides a method for determining the susceptibility to diseases associated with a defect in GP88 expression or action which comprises obtaining a sample of biological fluid or tissue and measuring the amount of GP88 in the fluid or tissue or measuring the susceptibility of the cells to respond to GP88. In the case of cancer, the amount of GP88 being proportional to the susceptibility to the cancer.

The present invention also provides a method for measuring the degree of severity of cancer which comprises obtaining a sample of biological fluid or tissue and measuring the amount of GP88 in the fluid or tissue sample, the amount of GP88 being proportional to the degree or severity of the cancer.

The present invention also provides a method for measuring susceptibility to GP88 antagonizing therapy which comprises obtaining a sample of the diseased tissue (biopsy), maintaining the cells derived from the sample in culture, treating the cells derived from the culture with anti-GP88 neutralizing antibody and determining if the neutralizing antibody inhibits the cell growth. Ability of the antibody to inhibit cell growth is indicative that the cells are dependent on GP88 to proliferate and is predictive that GP88 antagonizing therapy will be efficacious.

The present invention also provides a method for determining the susceptibility to cancer associated with an abnormality in GP88 receptor level or activity which comprises obtaining a sample of tissue and measuring the amount of GP88 receptor protein or mRNA in the tissue or measuring the tyrosine kinase activity of the receptor in the tissue (GP88 binding to its receptor induces tyrosine phosphorylation of cellular proteins including the receptor for G88).

The present invention also provides a method for targeting GP88 antagonizing reagents to the diseased site by conjugating them to an anti-GP88 antibody or an anti-GP88 receptor antibody.

The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 1A compares the level of expression of GP88 protein in the 1246, 1246-3A and PC cell lines. Cells were cultured in DME-F12 medium supplemented with 2% fetal bovine serum (FBS). GP88 expression levels were measured by immunoprecipitation and Western blot analysis with anti-K19T antibody.

FIG. 8 shows the nucleotide and deduced amino-acid sequence of mouse GP88. Peptide regions used as antigens to raise anti-GP88 (SEQ ID NOS: 1 & 2 respectively) antibodies K19T and S14R are underlined. The region cloned in the antisense orientation in the pCMV4 mammalian expression vector is indicated between brackets.

FIG. 9A shows the nucleotide sequence of human GP88 cDNA (SEQ ID NOS: 16 & 17 respectively). Indicated between brackets is the region cloned in the antisense orientation into the pcDNA3 mammalian expression system; and FIG. 9B shows the deduced amino-acid sequence of human GP88. The E19V region used as antigen to develop anti-human GP88 neutralizing antibody is underlined. It also indicates the region A14R equivalent to the mouse S14R region.

FIG. 10 shows the amino-acid sequence of mouse GP88 (SEQ ID NO: 2) arranged to show the 7 and one-half repeats defined as granulins g, f, B, A, C, D and e (right side). This representation shows that the region K19T and S14R used to raise GP88 antibodies for developing anti-GP88 neutralizing antibodies is found between two epithlin/granulin repeats in what is considered a variant region. Indicated on the right hand side is the granulin classification of the repeats according to Bateman et al (6). Granulin B and granulin A are also defined as epithelin 2 and epithelin 1 respectively according to Plowman et al., 1992 (5).

FIG. 11 shows a schematic representation of pCMV4 and a GP88 cDNA clone indicating the restriction sites used to clone GP88 antisense cDNA into the expression vector.

DESCRIPTION OF THE INVENTION

Reference will now be made in detail to the presently preferred embodiments of the invention, which, together with the following examples, serve to explain the principles of the invention.

Biological Activity of GP88

The invention relates to GP88 and antitumor and antiviral compositions useful for treating and diagnosing diseases linked to altered (increased) expression of GP88. Alternatively this invention is used for treating and diagnosing diseases linked to increased responsiveness to GP88. Using a murine model system consisting of three cell lines, the inventor has shown that cells which overexpress GP88 form tumors. The parent cell line, 1246, is a C3H mouse adipogenic cell line which proliferates and differentiates into adipocytes in a defined medium under stringent regulation by insulin (9, 10). The 1246 cells cannot form tumors in a syngeneic animal (C3H mouse) even when injected at a high cell density. An insulin independent cell line, 1246-3A, was isolated from 1246 cells maintained in insulin-free medium (11). The 1246-3A cells lost the ability to differentiate and form tumors when $10^6$ are injected subcutaneously in syngeneic mice. A highly tumorigenic cell line, PC, was developed from 1246-3A cells by an in vitro-in vivo shuttle technique. The PC cells formed tumors when $10^4$ cells were injected into syngeneic mice (12).

GP88 is overexpressed in the insulin-independent tumorigenic cell lines relative to the parent non-tumorigenic insulin-independent cell line. Moreover, the degree of overexpression of GP88 positively correlates with the degree of tumorigenicity of these cells, demonstrating for the fist time that GP88 is important in tumorigenesis (FIG. 1). With reference to FIG. 1, since GP88 is synthesized by cells but also secreted in culture medium, the level of GP88 was determined in cell lysates and in culture medium (CM). All cells were cultivated in DME/F12 nutrient medium supplemented with 2% fetal bovine serum. When cells reached confluency, culture medium (CM) was collected and cell lysates were prepared by incubation in buffer containing detergent followed by a 10,000×g centrifugation. Cell lysate and conditioned medium were normalized by cell number. Samples from cell lysate and conditioned medium were analyzed by Western blot analysis using an anti-GP88 antibody, as explained below.

Figure 2:
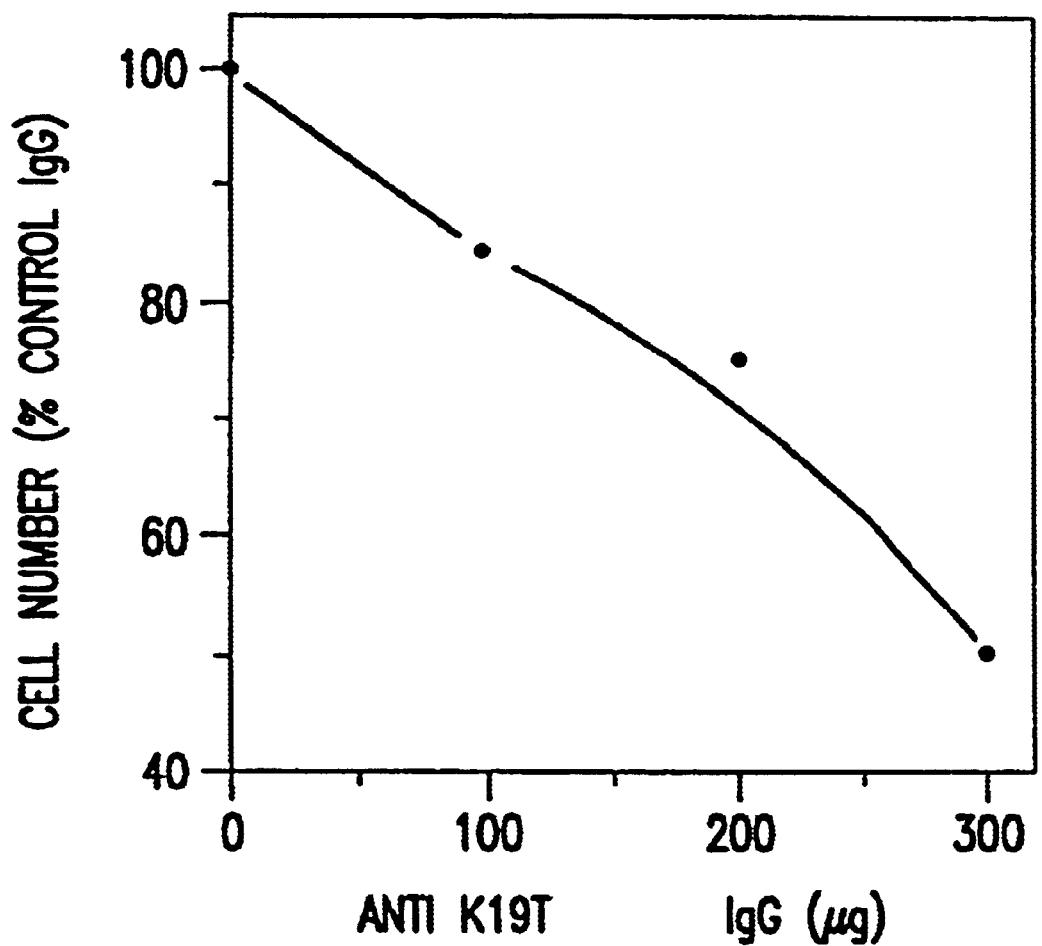
FIG. 2 illustrates the effect of treatment of the highly tumorigenic PC cells with increasing concentrations of anti-GP88 neutralizing antibody.

The development of a neutralizing antibody confirmed GP88's key role in tumorigenesis. When an anti-GP88 antibody directed to the K19T region of mouse GP88 was added to the culture medium, the growth of highly tumorigenic PC cells was inhibited in a dose dependent fashion (FIG. 2). With reference to FIG. 2, PC cells were cultivated in 96 well plates at a density $2 \times 10^4$ cell/well in DME/F12 medium supplemented with human fibronectin (2 µg/ml) and human transferrin (10 µg/ml). Increasing concentrations of anti-GP88 IgG fraction were added to the wells after the cells were attached. Control cells were treated with equivalent concentrations of non-immune IgG. Two days later, 0.25 mCi of $^3$H-thymidine was added per well for 6 hrs. Cells were then harvested to count $^3$H-thymidine incorporated into DNA as a measure for cell proliferation.

Figure 3:
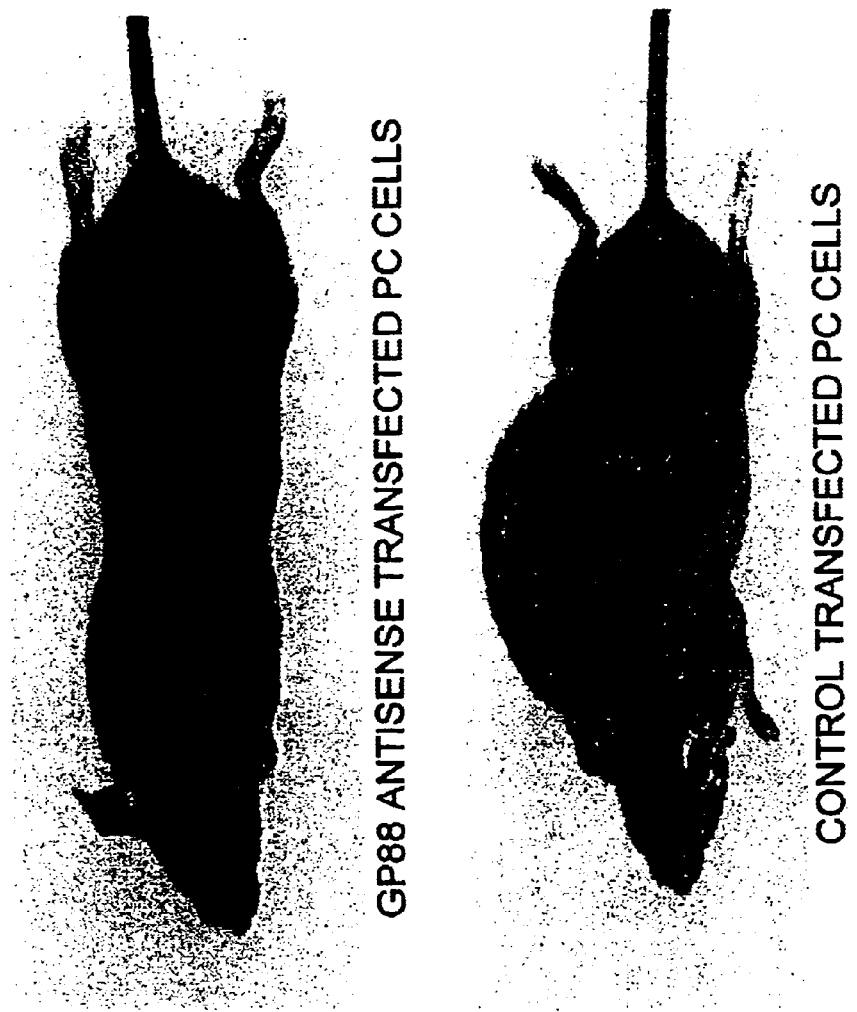
FIG. 3 shows C3H mice injected subcutaneously with $10^6$ antisense GP88 transfected PC cells (bottom) and with empty vector transfected control PC cells (top).

Moreover, when the expression of GP88 was specifically inhibited by antisense GP88 CDNA in PC cells, the production of GP88 was reduced and these PC cells could no longer form tumors in syngeneic C3H mouse. In addition, these PC cells regained responsiveness to insulin. With reference to FIG. 3 and Tables 1 and 2, C3H female mice were infected subcutaneously with $10^6$ antisense GP88 transfected PC cells (as explained below) or $10^6$ empty vector transfected PC cells. Mice were monitored daily for tumor appearance.

Photographs were taken 45 days after injection of the cells. The results show that mice injected with antisense GP88 PC cells do not develop tumors, in contrast to the mice injected with empty vector transfected PC cells used as control.

TABLE 1

COMPARISON OF TUMORIGENIC PROPERTIES OF GP88 ANTISENSE TRANSFECTED CELLS, CONTROL TRANSFECTED CELLS AND PC CELLS

| CELLS INJECTED | AVERAGE DAY OF TUMOR DETECTION | NUMBER OF MICE WITH TUMORS | AVERAGE TUMOR WEIGHT (g) |
| --- | --- | --- | --- |
| PC | 15 ± 3.0 | 5/5 | 9.0 ± 3.2 |
| P14 | 15 ± 3.7 | 5/5 | 7.8 ± 2.7 |
| ASGP88 | — | 0/5 | — |

PC: Control non-transfected cells
P-14: Empty vector control transfected PC cells
ASGP88: PC cells transfected with expression vector containing GP88 antisense cDNA
Tumors were excised and weighed at 45 days.
—indicates no tumor formation.

TABLE 2

COMPARISON OF PROPERTIES OF 1246, PC CELLS AND GP88 ANTISENSE CELLS

| 1246 cells | insulin independence PC cells | GP88 antisense transfection Antisense GP88 cells |
| --- | --- | --- |
| insulin responsive for growth and differentiation | insulin-independent for growth differentiation deficient | recovery of insulin responsiveness for growth (differentiation?) |
| | autocrine production of insulin-related factor | |
| cell surface insulin receptor expression high | cell surface insulin receptor expression very low | cell surface insulin receptor expression elevated |
| GP88 expression low | GP88 expression constitutively high | GP88 expression inhibited by antisense |
| GP88 expression inhibited by serum | No inhibition by serum | |
| GP88 expression regulated by insulin | GP88 expression constitutive | recovery of insulin regulation for endogenous GP88 expression |
| non-tumorigenic | highly tumorigenic | non-tumorigenic |

Figure 4:
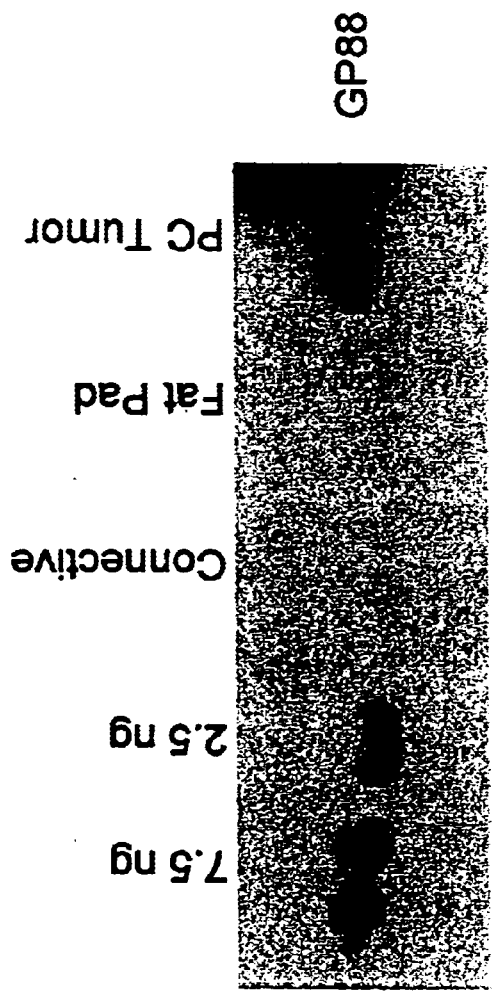
FIG. 4 shows in vivo GP88 expression levels in C3H mice tumor tissues and in surrounding normal tissues.

Comparison of the expression of GP88 indicates that in vivo GP88 levels in tumors is dramatically higher than in normal tissues (FIG. 4). C3H mice were injected with $10^6$ PC cells. Tumor bearing mice were euthanized. Tumors, fat pads and connective tissue were collected. Cell lysates were prepared by incubation in buffer containing detergent as described above for FIG. 1. Protein concentration of tissue extracts was determined, and equivalent amounts of proteins for each sample were analyzed by SDS-PAGE followed by Western blot analysis using anti-GP88 antibody to measure the content of GP88 in tissue extracts. The results showed that the level of GP88 in tumor extracts is at least 10-fold higher than in surrounding connective and fat tissues.

In normal cells (1246 cells, fibroblasts), the expression of GP88 is regulated, in particular by insulin, and inhibited by fetal bovine serum. In tumorigenic cells, a loss of regulation of normal growth leads to the increased expression of GP88 and the acquisition of GP88 dependence for growth. Therefore, inhibition of GP88 expression and/or action is an effective approach to suppression of tumorigenesis. Detection of an elevated GP88 expression in biopsies provides diagnostic analysis of tumors that are responsive to GP88 inhibition therapy.

Figure 5:
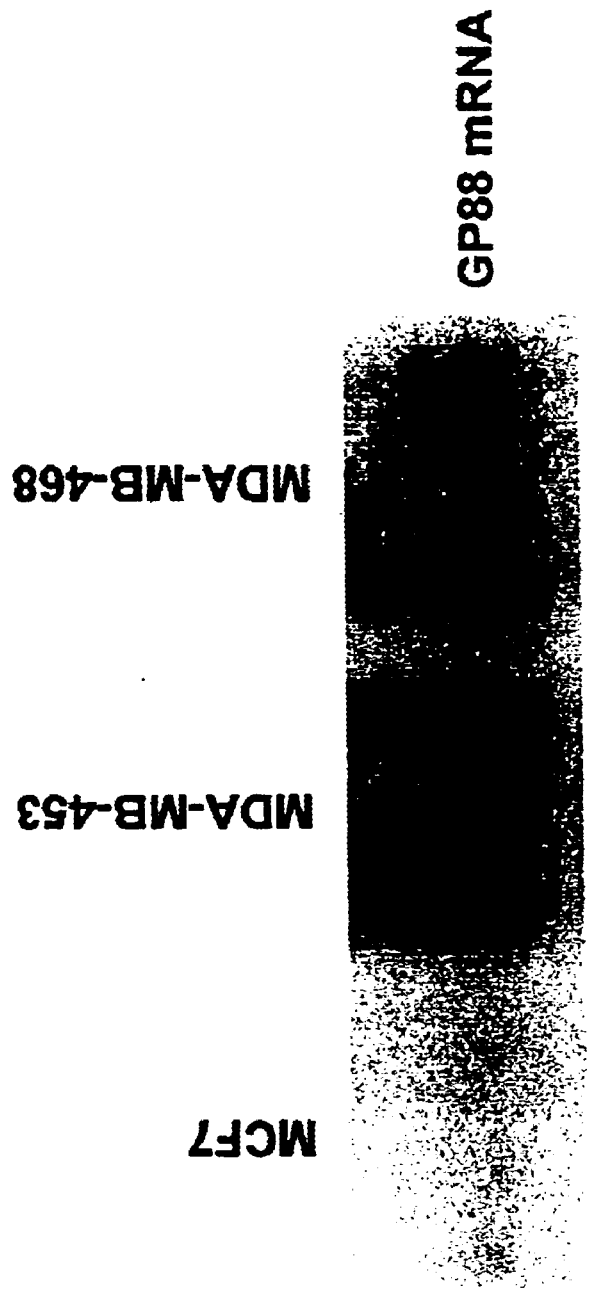
FIG. 5 shows GP88 mRNA expression levels in estrogen receptor positive and estrogen receptor negative human mammary carcinoma cell lines.
Figure 6A:
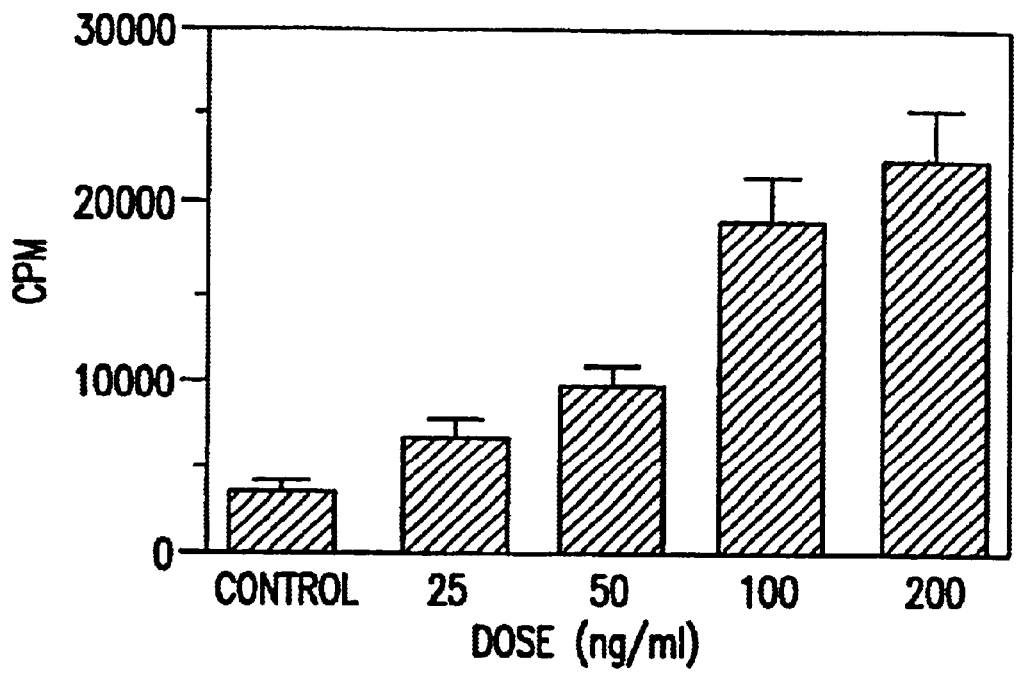
FIG. 6 shows the effect of increasing concentrations of GP88 on the growth of the mouse mammary epithelial cell line C57.
Figure 6B:
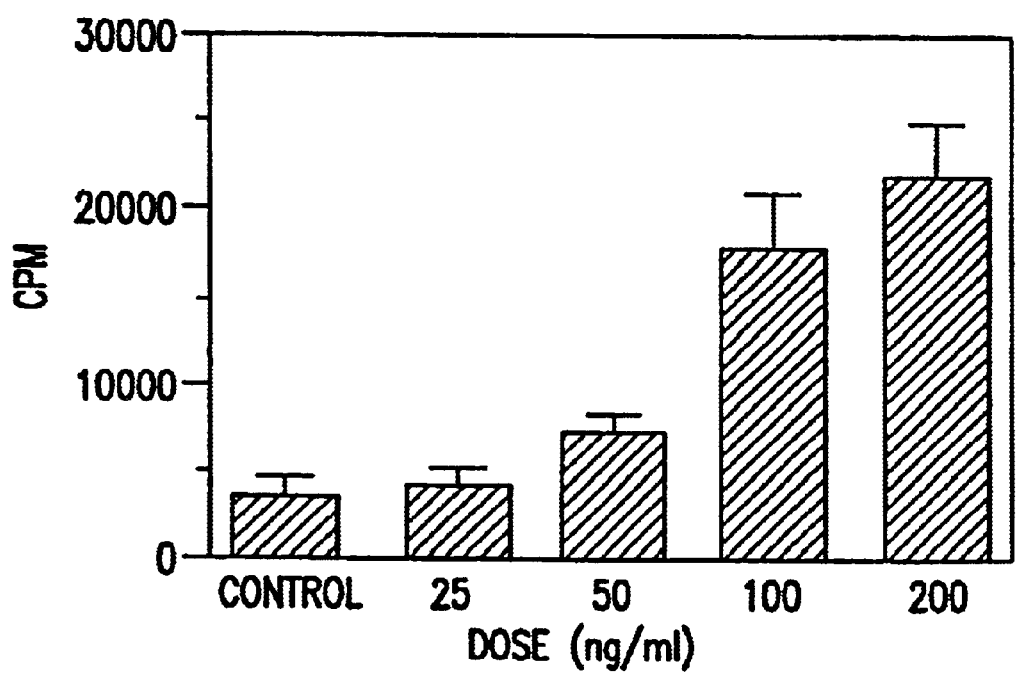

GP88 is also a tumor inducing factor in human cancers. As seen in the 1246-3A cell line, a loss of responsiveness to insulin (or to IGF-I) and a concurrent increase in malignancy has been well documented (13, 14) in several human cancers including but not limited to breast cancers. Specifically, breast carcinoma is accompanied by the acquisition of an insulin/IGF-I autocrine loop, which is also the starting point of the development of tumorigenic properties in the mouse model system discussed above. Furthermore, GP88 expression is elevated in human breast carcinomas. More specifically, with reference to FIG. 5, human GP88 was highly expressed in estrogen receptor positive and also in estrogen receptor negative insulin/IGF-I independent highly malignant cells. Also, GP88 is a potent growth factor for mammary epithelial cells (FIG. 6). The data in FIG. 5 was obtained by cultivating MCF7, MDA-MB-453 and MDA-MB-468 cells in DME/F12 medium supplemented with 10% fetal bovine serum (FBS). RNA was extracted from each cell line by the RNAzol method and poly-A$^+$ RNA prepared. GP88 mRNA expression was examined by Northern blot analysis with 3 µg of poly-A$^+$ RNA for each cell line using a $^{32}$P-labeled GP88 cDNA probe.

For Northern blot analysis of GP88 mRNA expression in rodent cells or tissues (mouse and rats), we used a mouse GP88 cDNA probe 311 bp in length starting at nucleotide 551 to 862 (corresponding to amino-acid sequence 160 to 270). RNA can be extracted by a variety of methods (Sambrook, Molecular Biology manual: 35) well known to people of ordinary skill in the art. The method of choice was to extract RNA using RNAzol (Cinnabiotech) or Trizol (Gibco-BRL) solutions which consists of a single step extraction by guanidinium isothiocyanate and phenol-chloroform.

For Northern blot analysis of GP88 mRNA expression in human cell lines, a 672 bp human GP88 cDNA probe was developed corresponding to nucleotide 1002 to 1674 (corresponding to amino-acid sequence 334–558) of human GP88. See example 8 for a detailed and specific description of the Northern blot analysis method used in the preferred embodiments.

With respect to FIG. 6, C57MG cells were cultivated in the presence of increasing concentrations of GP88 purified from PC cells conditioned medium (top panel), and recombinant GP88 expressed in insect cells (bottom panel), to demonstrate the growth stimulating effect of increasing concentrations of GP88 on the growth of the mouse mammary epithelial cell line C57MG.

A correlation between IGF-I autocrine production and increased malignancy has also been well established for glioblastomas, teratocarcinomas and breast carcinomas (2, 15, 16, 17). In these cancers, GP88 expression is also elevated in human tumors when compared to non-tumorigenic human fibroblasts and other human cell lines. GP88 promotes the growth of mammary carcinoma cells.

Anti-GP88 Antibodies

The invention provides compositions for treating and diagnosing diseases linked to increased expression of GP88. This also will apply to treatment and diagnosis of diseases linked to increased responsiveness to GP88. The compositions of this invention include anti-GP88 antibodies which neutralize the biological activity of GP88.

The present invention is also directed to an antibody specific for an epitope of GP88 and the use of such antibody to detect the presence or measure the quantity or concentration of GP88 molecule, a functional derivative thereof or a homologue from different animal species in a cell, a cell or tissue extract, culture medium or biological fluid. Moreover, antibody can be used to target cytotoxic molecules to a specific site.

For use as antigen for development of antibodies, the GP88 protein naturally produced or expressed in recombinant form or functional derivative thereof, preferably having at least 9 amino-acids, is obtained and used to immunize an animal for production of polyclonal or monoclonal antibody. An antibody is said to be capable of binding a molecule if it is capable of reacting with the molecule to thereby bind the molecule to the antibody. The specific reaction is meant to indicate that the antigen will react in a highly selective manner with its corresponding antibody and not with the multitude of other antibodies which may be evoked by other antigens.

The term antibody herein includes but is not limited to human and non-human polyclonal antibodies, human and non-human monoclonal antibodies (mAbs), chimeric antibodies, anti-idiotypic antibodies (anti-IdAb) and humanized antibodies. Polyclonal antibodies are heterogeneous populations of antibody molecules derived either from sera of animals immunized with an antigen or from chicken eggs. Monoclonal antibodies ("mAbs") are substantially homogeneous populations of antibodies to specific antigens. mAbs may be obtained by methods known to those skilled in the art (18, 19, 20 and U.S. Pat. No. 4,376,110). Such antibodies may be of any immunological class including IgG, IgM, IgE, IgA, IgD and any subclass thereof. The hybridoma producing human and non-human antibodies to GP88 may be cultivated in vitro or in vivo. For production of a large amount of mAbs, in vivo is the presently preferred method of production. Briefly, cells from the individual hybridomas are injected intraperitoneally into pristane primed Balb/c mice or Nude mice to produce ascites fluid containing high concentrations of the desired mAbs. mAbs may be purified from such ascites fluids or from culture supernatants using standard chromatography methods well known to those of skill in the art.

Human monoclonal Ab to human GP88 can be prepared by immunizing transgenic mice expressing human immunoglobulin genes. Hybridoma produced by using lymphocytes from these transgenic animals will produce human immunoglobulin instead of mouse immunoglobulin.

Since most monoclonal antibodies are derived from murine source and other non-human sources, their clinical efficiency may be limited due to the immunogenicity of rodent mAbs administered to humans, weak recruitment of effector function and rapid clearance from serum (25). To circumvent these problems, the antigen-binding properties of murine antibodies can be conferred to human antibodies through a process called humanization (25). A humanized antibody contains the amino-acid sequences for the 6 complementarity-determining regions (CDRs) of the parent murine mAb which are grafted onto a human antibody framework. The low content of non-human sequences in humanized antibodies (around 5%) has proven effective in both reducing the immunogenicity and prolonging the serum half life in humans. Methods such as the ones using monovalent phage display and combinatorial library strategy (26, 27) for humanization of monoclonal antibodies are now widely applied to the humanization of a variety of antibodies and are known to people skilled in the art. These humanized antibodies and human antibodies developed with transgenic animals as described above are of great therapeutic use for several diseases including but not limited to cancer.

Hybridoma supernatants and sera are screened for the presence of antibody specific for GP88 by any number of inmunoassays including dot blots and standard immunoassays (EIA or ELISA) which are well known in the art. Once a supernatant has been identified as having an antibody of interest, it may be further screened by Western blotting to identify the size of the antigen to which the antibody binds. One of ordinary skill in the art will know how to prepare and screen such hybridomas without undue experimentation in order to obtain a desired polyclonal or mAb.

Chimeric antibodies have different portions derived from different animal species. For example, a chimeric antibody might have a variable region from a murine mAb and a human immunoglobulin constant region. Chimeric antibodies and methods for their production are also known to those skilled in the art (21–24).

An anti-idiotypic ("anti-IdAb") is an antibody which recognizes unique determinants generally associated with the antigen-binding site of an antibody. An anti-IdAb can be prepared by immunizing an animal of the same species and genetic type (e.g., mouse strain) as the source of the mAb with the mAb to which an anti-IdAb is being prepared. The immunized animal will recognize and respond to the idiotypic determinants of the immunizing antibody by producing antibody to these idiotypic determinants (the anti-IdAb). The anti-IdAb may also be used as an immunogen to produce an immune response in yet another animal, producing a s called anti-anti-IdAb. The anti-anti-IdAb may be epitopically identical to the original mAb which induced the anti-IdAb. Thus by using antibodies to the idiotypic determinants of a mAb, it is possible to identify other clones expressing antibodies of identical specificity.

Accordingly, mAbs generated against GP88 may be used to induce human and non-human anti-IdAbs in suitable animals. Spleen cells from such immunized mice are used to produce hybridomas secreting human or non-human anti-Id mAbs. Further, the anti-Id mAbs can be coupled to a carrier such as Keyhole Limpet Hemocyanin (KLH) or bovine serum albumin (BSA) and used to immunize additional mice. Sera from these mice will contain human or non-human anti-anti-IdAb that have the binding properties of the original mAb specific for a GP88 polypeptide epitope. The anti-Id mAbs thus have their own idiotypic epitopes or idiotypes structurally similar to the epitope being evaluated.

The term antibody is also meant to include both intact molecules as well as fragments thereof such as, for example, Fab and F(ab')2, which are capable of binding to the antigen. Fab and F(ab')2 fragments lack the Fc fragment of intact antibody, clear more rapidly from the circulation and may have less non-specific tissue binding than an intact antibody (28). Such fragments are typically produced by proteolytic cleavage, using enzymes such as papain (to generate Fab fragments) and pepsin (to generate F(ab')2 fragments). It will be appreciated that Fab and F(ab')2 and other fragments of the antibodies useful in the present invention may be used for the detection or quantitation of GP88, and for treatment of pathological states related to GP88 expression, according to the methods disclosed herein for intact antibody molecules.

According to the present invention, antibodies that neutralize GP88 activity in vitro can be used to neutrize GP88 activity in vivo to treat diseases associated with increased GP88 expression or increased responsiveness to GP88, such as but not limited to cancer and viral infection. A subject, preferably a human subject, suffering from disease associated with increased GP88 expression is treated with an antibody to GP88. Such treatment may be performed in conjunction with other anti cancer or anti-viral therapy. A typical regimen comprises administration of an effective amount of the antibody specific for GP88 administered over a period of one or several weeks and including between about one and six months. The antibody of the present invention may be administered by any means that achieves its intended purpose. For example, administration may be by various routes including but not limited to subcutaneous, intravenous, intradermal, intramuscular, intraperitoneal and oral. Parenteral administration can be by bolus injection or by gradual perfusion over time. Preparations for parenteral administration include sterile aqueous or non-aqueous solutions, suspensions and emulsions, which may contain auxiliary agents or excipients known in the art. Pharmaceutical compositions such as tablets and capsules can also be prepared according to routine methods. It is understood that the dosage of will be dependent upon the age, sex and weight of the recipient, kind of concurrent treatment, if any, frequency of treatment and the nature of the effect desired. The ranges of effective doses provided below are not intended to limit the invention and merely represent preferred dose ranges. However the most preferred dosage will be tailored to the individual subject as is understood and determinable by one skilled in the art. The total dose required for each treatment may be administered by multiple doses or in a single dose. Effective amounts of antibody are from about 0.10 $\mu$g to about 100 mg/kg body weight and preferably from about 10 $\mu$g to about 50 mg/kg. Antibody may be administered alone or in conjunction with other therapeutics directed to the same disease.

According to the present invention and concerning the neutralizing antibody, GP88 neutralizing antibodies can be used in all therapeutic cases where it is necessary to inhibit GP88 biological activity, even though there may not necessarily be a change in GP88 expression, including cases where there is an overexpression of GP88 cell surface receptors and this in turn results in an increased biological activity, or where there is an alteration in GP88 signaling pathways or receptors leading to the fact that the signaling pathways are always "turned on." Neutralizing antibodies to growth factor and to growth factor receptors have been successfully used to inhibit the growth of cells whose proliferation is dependent on this growth factor. This has been the case for IGF-I receptor in human breast carcinoma cells (14) and bombesin for lung cancer (29). The antibody to GP88 can also be used to deliver compounds such as, but not limited to, cytotoxic reagents such as toxins, oncotoxins, mitotoxins and immunotoxins, or antisense oligonucleotides, in order to specifically target them to cells expressing or responsive to GP88 (30).

One region that allows antigen to develop a neutralizing antibody to GP88 is the 19 amino-acid region defined as K19T in the mouse GP88, and E19V in the human GP88 which is not located within the epithelin/granulin 6 kDa repeats but between these repeats, specifically between granulin A (epithelin 1) and granulin C (5) in what is considered a variant region (see FIG. 10). Without wishing to be bound by theory, it is believed that the region important for the biological activity of GP88 lies outside of the epithelin repeats.

The antibodies or fragments of antibodies useful in the present invention may also be used to quantitatively or qualitatively detect the presence of cells which express the GP88 protein. This can be accomplished by immunofluorescence techniques employing a fluorescently labeled antibody (see below) with fluorescent microscopic, flow cytometric, or fluorometric detection. The reaction of antibodies and polypeptides of the present invention may be detected by immunoassay methods well known in the art (20).

The antibodies of the present invention may be employed histologically as in light microscopy, immunofluorescence or immunoelectron microscopy, for in situ detection of the GP88 protein in tissues samples or biopsies. In situ detection may be accomplished by removing a histological specimen from a patient and applying the appropriately labeled antibody of the present invention. The antibody (or fragment) is preferably provided by applying or overlaying the labeled antibody (or fragment) to the biological sample. Through the use of such a procedure, it is possible to determine not only the presence of the. GP88 protein but also its distribution in the examined tissue. Using the present invention, those of ordinary skill in the art will readily perceive that any wide variety of histological methods (such as staining procedures) can be modified in order to achieve such in situ detection.

Assays for GP88 typically comprise incubating a biological sample such as a biological fluid, a tissue extract, freshly harvested or cultured cells or their culture medium in the presence of a detectably labeled antibody capable of identifying the GP88 protein and detecting the antibody by any of a number of techniques well known in the art.

The biological sample may be treated with a solid phase support or carrier such as nitrocellulose or other solid support capable of immobilizing cells or cell particles or soluble proteins. The support may then be washed followed by treatment with the detectably labeled anti-GP88 antibody.

This is followed by wash of the support to remove unbound antibody. The amount of bound label on said support may then be detected by conventional means. By solid phase support is intended any support capable of binding antigen or antibodies such as but not limited to glass, polystyrene polypropylene, nylon, modified cellulose, or polyacrylamide.

The binding activity of a given lot of antibody to the GP88 protein may be determined according to well known methods. Those skilled in the art will be able to determine operative and optimal assay conditions for each determination by employing routine experimentation.

Detection of the GP88 protein or functional derivative thereof and of a specific antibody for the protein may be accomplished by a variety of immunoassays well known in the art such as enzyme linked immunoassays (EIA) or radioimmunoassays (RIA). Such assays are well known in the art and one of skill will readily know how to carry out such assays using the anti-GP88 antibodies and GP88 protein of the present invention.

Such immunoassays are useful to detect and quantitate GP88 protein in serum or other biological fluid as well as in tissues, cells, cell extracts, or biopsies. In a preferred embodiment, the concentration of GP88 is measured in a tissue specimen as a means for diagnosing cancer or other disease associated with increased expression of GP88.

The presence of certain types of cancers and the degree of malignancy are said to be "proportional" to an increase in the level of the GP88 protein. The term "proportional" as used herein is not intended to be limited to a linear or constant relationship between the level of protein and the malignant properties of the cancer. The term "proportional" as used herein, is intended to indicate that an increased level of GP88 protein is related to appearance, recurrence or display of malignant properties of a cancer or other disease associated with increased expression of GP88 at ranges of concentration of the protein that can be readily determined by one skilled in the art.

Another embodiment of the invention relates to evaluating the efficacy of anti-cancer or anti-viral drug or agent by measuring the ability of the drug or agent to inhibit the expression or production of GP88. The antibodies of the present invention are useful in a method for evaluating anti-cancer or anti-viral drugs in that they can be employed to determine the amount of the GP88 protein in one of the above-mentioned inmunoassays. Alternatively, the amount of the GP88 protein produced is measured by bioassay (cell proliferation assay) as described herein. The bioassay and immunoassay can be used in combination for a more precise assessment.

An additional embodiment is directed to an assay for diagnosing cancers or other diseases associated with an increase in GP88 expression based on measuring in a tissue or biological fluid the amount of mRNA sequences present that encode GP88 or a functional derivative thereof, preferably using an RNA-DNA hybridization assay. The presence of certain cancers and the degree of malignancy is proportional to the amount of such mRNA present. For such assays the source of mRNA will be biopsies and surrounding tissues. The preferred technique for measuring the amount of mRNA is a hybridization assay using DNA of complementarity base sequence.

Another related embodiment is directed to an assay for diagnosing cancers or other diseases associated with an increase in GP88 responsiveness based on measuring on a tissue biopsy whether treatment with anti-GP88 neutralizing antibody will inhibit its growth or other biological activity.

Another related embodiment is a method for measuring the efficacy of anti-cancer or anti-viral drug or agent which comprises the steps of measuring the agent's effect on inhibiting the expression of mRNA for GP88. Similarly such method can be used to identify or evaluate the efficacy of GP88 antagonizing agents by measuring the ability of said agent to inhibit the production of GP88 mRNA.

Nucleic acid detection assays, especially hybridization assays, can be based on any characteristic of the nucleic acid molecule such as its size, sequence, or susceptibility to digestion by restriction endonucleases. The sensitivity of such assays can be increased by altering the manner in which detection is reported or signaled to the observer. A wide variety of labels have been extensively developed and used by those of ordinary skill in the art, including enzymatic, radioisotopic, fluorescent, chemical labels and modified bases.

One method for overcoming the sensitivity limitation of a nucleic acid for detection is to selectively amplify the nucleic acid prior to performing the assay. This method has been referred as the "polymerase chain reaction" or PCR (31 and U.S. Pat. Nos. 4,683,202 and 4,582,788). The PCR reaction provides a method for selectively increasing the concentration of a particular nucleic acid sequence even when that sequence has not been previously purified and is present only in a single copy in a particular sample.

GP88 Antisense Components

This invention also provides GP88 antisense components. The constitutive expression of antisense RNA in cells has been shown to inhibit the expression of more than 20 genes and the list continues to grow (32–34). Possible mechanisms for antisense effects are the blockage of translation or prevention of splicing, both of which have been observed in vitro. Interference with splicing allows the use of intron sequences (30) which should be less conserved and therefore result in greater specificity, inhibiting expression of a gene product of one species but not its homologue in another species.

The term antisense component corresponds to an RNA sequence as well as a DNA sequence coding therefor, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. The action of the antisense RNA results in specific inhibition of gene expression in the cells (32–35).

According to the present invention, transfection of tumorigenic cells with DNA antisense to the GP88 cDNA inhibits endogenous GP88 expression and inhibits tumorigenicity of the antisense cDNA transfected cells. This antisense DNA must have sufficient complementarity, about 18–30 nucleotides in length, to the GP88 gene so that the antisense RNA can hybridize to the GP88 gene (or mRNA) and inhibit GP88 gene expression regardless of whether the action is at the level of splicing, transcription, or translation. The degree of inhibition is readily discernible to one skilled in the art without undue experimentation given the teachings herein and preferably is sufficient to inhibit the growth of cells whose proliferation is dependent on the expression of GP88. One of ordinary skill in the art will recognize that the antisense RNA approach is but a number of known mechanisms which can be employed to block specific gene expression.

The antisense components of the present invention may be hybridizable to any of several portions of the target GP88 cDNA, including the coding sequence, 3' or 5' untranslated regions, or other intronic sequences, or to GP88 mRNA. As is readily discernible by one of ordinary skill in the art, the minimal amount of homology required by the present invention is that sufficient to result in hybridization to the GP88 DNA or mRNA and in inhibition of transcription of the DNA, or translation or function of the mRNA, preferably without affecting the function of other mRNA molecules and the expression of other unrelated genes.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. Stable transfection of various antisense expression vectors containing GP88 CDNA fragments in the antisense orientation have been performed. One can also deliver antisense components to cells using a retroviral vector. Delivery can also be achieved by liposomes.

For purpose of antisense technology for in vivo therapy, the currently preferred method is to use antisense oligonucleotides (32, 36), instead of performing stable tansfection of an antisense cDNA fragment constructed into an expression vector. Antisense oligonucleotides having a size of 15–30 bases in length and with sequences hybridizable to any of several portions of the target GP88 cDNA, including the coding sequence, 3' or 5' untranslated regions, or other intronic sequences, or to GP88 mRNA, are preferred. Sequences for the antisense oligonucleotides to GP88 are preferably selected as being the ones that have the most potent antisense effects (37, 38). Factors that govern a target site for the antisense oligonucleotide sequence are related to the length of the oligonucleotide, binding affinity, and accessibility of the target sequence. Sequences may be screened in vitro for potency of their antisense activity by measuring inhibition of GP88 protein translation and GP88 related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred GP88 antisense oligonucleotides are those oligonucleotides which are stable, have a high resilience to nucleases (enzymes that could potentially degrade oligonucleotides), possess suitable pharmacokinetics to allow them to traffic to disease tissue at non-toxic doses, and have the ability to cross through plasma membranes.

Phosphorothioate antisense oligonucleotides may be used (39). Modifications of the phosphodiester linkage as well as of the heterocycle or the sugar may provide an increase in efficiency. With respect to modification of the phosphodiester linkage, phophorothioate may be used. An N3'-P5' phosphoramidate linkage has been described as stabilizing oligonucleotides to nucleases and increasing the binding to RNA (40). Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo. Cell culture and in vivo tumor experiments using these types of oligonucleotides targeted to c-raf-1 resulted in enhanced potency. As general references for antisense oligonucleotides, see (32–34)

The delivery route will be the one that provides the best antisense effect as measured according to the criteria described above. In vitro cell culture assays and in vivo tumor growth assays using antisense oligonucleotides have shown that delivery mediated by cationic liposomes, by retroviral vectors and direct delivery are efficient. (36, 41–43) Another possible delivery mode is targeting using antibody to cell surface markers for the tumor cells. Antibody to GP88 or to its receptor may serve this purpose.

Recombinant GP88

The present invention is also directed to DNA expression systems for expressing a recombinant GP88 polypeptide or a functional derivative thereof substantially free of other mammalian DNA sequences. Such DNA may be double or single stranded. The DNA sequence should preferably have about 20 or more nucleotides to allow hybridization to another polynucleotide. In order to achieve higher specificity of hybridization, characterized by the absence of hybridization to sequences other than those encoding the GP88 protein or a homologue or functional derivative thereof, a length of at least 50 nucleotides is preferred.

The present invention is also directed to the above DNA molecules, expressible vehicles or vectors as well as hosts transfected or transformed with the vehicles and capable of expressing the polypeptide. Such hosts may be prokaryotic, preferably bacteria, or eukaryotic, preferably yeast or mammalian cells. A preferred vector system includes baculovirus expressed in insect cells. The DNA can be incorporated into host organisms by transformation, transduction, transfection, infection or related processes known in the art. In addition to DNA and mRNA sequences encoding the GP88 polypeptide, the invention also provides methods for expression of the nucleic acid sequence. Further, the genetic sequences and oligonucleotides allow identification and cloning of additional polypeptides having sequence homology to the polypeptide GP88 described here.

An expression vector is a vector which (due to the presence of appropriate transcriptional and/or translational control sequences) is capable of expressing a DNA (or cDNA) molecule which has been cloned into the vector and thereby produces a polypeptide or protein. Expression of the cloned sequence occurs when the expression vector is introduced into an appropriate host cell. If a prokaryotic expression vector is employed, then the appropriate host cell would be any prokaryotic cell capable of expressing the cloned sequence. Similarly, if an eukaryotic expression system is employed, then the appropriate host cell would be any eukaryotic cell capable of expressing the cloned sequence. Baculovirus vector, for example, can be used to clone GP88 cDNA and subsequently express the cDNA in insect cells.

A DNA sequence encoding GP88 polypeptide or its functional derivatives may be recombined with vector DNA in accordance with conventional techniques including blunt-ended or staggered ended termini for ligation, restriction enzyme digestion to provide appropriate termini, filling in cohesive ends as appropriate, alkaline phosphatase treatment to avoid undesirable joining, and ligation with proper enzyme ligases. Techniques for such manipulations are discussed in (35).

A nucleic acid molecule is capable of expressing a polypeptide if it contains nucleotide sequences which contain transcriptional and translational regulatory information and such sequences are operably linked to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism but shall in general include a promoter region, which in prokaryotes contains both the promoter (which directs the initiation of RNA transcription) as well as the DNA sequences which when transcribed into RNA will signal the initiation of protein synthesis. Such regions will normally include those 5' non-coding sequences involved with the initiation of transcription, translation such as the TATA box, capping sequence, CAAT sequence and the like.

If desired, the 3' non-coding region to the gene sequence encoding the protein may be obtained by described methods (screening appropriate cDNA library or PCR amplification). This region may be retained for the presence of transcriptional termination regulatory sequences such as termination and polyadenylation. Thus, by retaining the 3' region naturally contiguous to the DNA sequence coding for the protein, the transcriptional termination signals may be provided. Where the transcription termination signals are not provided or satisfactorily functional in the expression host cells, then a 3' region from another gene may be substituted.

Two DNA sequences such as a promoter region sequence and GP88 encoding sequence are said to be operably linked if the nature of the linkage between the sequences does not (1) result in the introduction of a frame-shift mutation or (2) interfere with the ability of the promoter sequence to direct transcription of the polypeptide gene sequence.

The promoter sequences may be prokaryotic, eukaryotic or viral. Suitable promoters are inducible, repressible or constitutive. Examples of suitable prokaryotic promoters are reviewed by (44–46).

Eukaryotic promoters include but are not limited to the promoter for the mouse methallothionein I gene (47), the TK promoter of Herpes Virus (48), the gene gal4 promoter (49), the SV40 early promoter (50), the mouse mammary tumor virus (MMTV) promoter, and the cytomegalovirus (CMV) promoter (51). Strong promoters are preferred. Examples of such promoters are those which recognize the T3, SP6 and T7 polymerases, the PL promoter of bacteriophage lambda, the recA promoter, the promoter of the mouse methallothionein I gene, the SV40 promoter and the CMV promoter.

It is to be understood that application of the teachings of the present invention to a specific problem or environment will be within the capability of one having ordinary skill in the art in light of the teachings contained herein. The present invention is more fully illustrated by the following non-limiting examples.

EXAMPLE 1

Isolation of PC Cell Line

The role of autocrine growth factor production in the loss of differentiation ability and acquisition of tumorigenic properties in mammalian cells has been studied using a murine model system developed by the inventor. It consists of the mouse C3H adipogenic cell line 1246 (9), a series of cell lines which are differentiation-deficient and have increasing tumorigenic properties. 1246 cells proliferate and differentiate in a serum-free defined medium (9). In defined medium, 1246 cells stringently require insulin for proliferation and for differentiation (10). Insulin-like growth factor I (IGF-I) can replace insulin for proliferation but not for differentiation. From 1246 cells maintained in the absence of insulin-dependent cell lines were isolated (11).

1246-3A was particularly studied. 1246-3A cells had lost the ability to differentiate and had become tumorigenic in vivo (11). 1246-3A cells formed tumors when $10^6$ cells were injected into syngeneic C3H mice within 6 weeks, whereas 1246 cells were non-tumorigenic. By an in vitro-in vivo shuttle technique, highly tumorigenic insulin-independent cell lines were subsequently isolated and analyzed (12).

The shuttle technique consisted of subcutaneously injecting 1246-3A cells ($10^6$ cells/mouse) into syngeneic C3H mice. The tumor resulting from the injection of the cells was then minced and plated in primary culture into defined medium deprived of insulin (DME/F12 nutrient medium 1:1 mixture supplemented with fibronectin, transferrin and FGF). Cells that had started to grow were subcultured when they reached confluency to be: (1) either frozen in the presence of 10% Fetal Bovine serum and 10% Dimethylsulfoxide (DMSO) for long term conservation; (2) injected subcutaneously into C3H mice at different cell densities ($10^6$, $10^5$, $10^4$ cells/mouse). Rate of appearance of tumor and size of tumor was monitored. Tumors that appeared were again put back in culture in the insulin-free medium. Cells growing in these conditions were reinjected back into the animal.

By this in vitro-in vivo shuttle technique insulin-independent cells with increasing tumorigenic properties were obtained. In particular, the highly tumorigenic cell line named PC was isolated (12). PC cells can form tumors even when $10^4$ cells are injected subcutaneously into syngeneic C3H mice.

The PC cell line has at least the following characteristics:

(1) These cells represent an excellent model system for tumorigenicity studies: these cells can proliferate in a simple defined medium DME-F12 nutrient mixture supplemented with 2 $\mu$g/ml fibronectin and 10 $\mu$g/ml transferrin, and they can be injected into syngeneic hosts and do not require the use of nude mice which are expensive and necessitate special handling.

(2) When the PC cells reach confluency, the cells can be maintained in a complete serum-free and factor-free medium. Their growth is maintained solely by the nutrient medium and the factors that the cells secrete in their conditioned medium, thus conditioned medium is a good source for characterization and purification of factors required for proliferation of tumor cells.

EXAMPLE 2

GP88 is an Autocrine Growth Factor for the Highly Tumorigenic PC Cells

It was shown that PC cell conditioned medium contained growth promoting activity that was purified by chromatographic techniques (4). The purified factor called GP88 precursor was sequenced and shown to be similar to the epithelin/granulin precursor.

Experiments were then carried out to examine whether the production of GP88 by PC cells stimulated their growth in an autocrine fashion. For this purpose, PC cells were cultivated in the presence of GP88 antibody that can neutralize GP88 activity. DNA synthesis of PC cells was measured in the presence of increasing amounts of either the non-immune IgG or the anti-K19T IgG.

As shown in FIG. 2, the addition of anti-GP88 IgG inhibited PC cell growth in a dose-dependent manner, directly demonstrating that GP88 production by the PC cells is required for their growth. Non-immune IgG had no effect. Here, PC cells were plated in 96-well plates at a density of $2\times10^4$ cells/well in DME/F12 medium supplemented with 2 µg/ml fibronectin and 10 µg/ml transferrin (2F medium). After 6 hours when the cells were attached, anti-GP88 IgG fraction was added. 36 hours later, $^3$H-thymidine (0.25 µCi/ml) was added for an additional 8 hours. Cells were collected by trypsinization on glass filters by a cell harvester and the radioactivity corresponding to $^3$H-thymidine incorporated into DNA counted by liquid scintillation counter. Values (FIG. 2) are expressed as % of control corresponding to thymidine incorporation in PC cells treated with equivalent amounts of nonimmune IgG.

Similar results were obtained using anti K19T and anti E19V monoclonal antibodies. Anti K19T monoclonal antibody inhibited the growth of PC cells and of rat leukemia cells in a dose dependent fashion. Moreover, anti E 19V monoclonal antibody inhibited the growth of the human breast carcinoma cell line MCF7, with an $ED_{50}$ of 100 µg/ml.

EXAMPLE 3

Expression of GP88 in the 1246, 1246-3A and PC Cell Lines

Since GP88 protein was purified from PC cell conditioned medium, experiments were carried out to compare the expression of GP88 mRNA and protein in the three cell lines.

Comparative tumorigenicity studies of 1246, 1246-3A and PC cell lines in C3H mice showed that PC cells are highly tumorigenic when compared to 1246-3A cells since they can develop tumors when $10^4$ cells/mouse are injected into C3H mice. 1246-3A cells make tumors when injected a $10^6$ cells/mouse, whereas in syngeneic hosts, 1236 cells are non-tumorigenic (12).

The following methods were used for the studies of comparing the level of GP88 in the model system consisting of the three cell lines 1246, 1246-3A and PC.

Cell Culture 1246 stock cells were maintained in DME/F12 nutrient medium (1:1 mixture of Dulbecco's modified Eagle medium and Ham's nutrient F12) supplemented with 10% fetal bovine serum (FBS). 1246-3A and PC stock cells were maintained in defined media For PC stock cells, it consisted of DME-F12 medium supplemented with 2 µg/ml of human plasma fibronectin and 10 µg/ml of human plasma transferrin (2F medium). For 1246-3A cells, the defined medium called 3F medium consisted of DME-F12 medium supplemented with 2 µg/ml of human plasma fibronectin and 10 µg/ml of human plasma transferrin and 1 ng/ml of basic fibroblast growth factor (bFGF). For comparative studies the three cell lines were plated in DME-F12 medium supplemented with 2% FBS.

RNA Isolation and Northern Blot Analysis

For Northern blot analysis of GP88 mRNA expression in rodent cells or tissues (mouse and rats), we used a mouse GP88 cDNA probe 311 bp in length starting at nucleotide 551 to 862 (corresponding to amino-acid sequence 160 to 270). The probe was $^{32}$P-labeled by random-priming reaction.

Total cellular RNA was isolated by RNAzol solution (Cinnabiotech) or Trizol solution (Life Technologies) based on a modification of the single step guanidinium isothiocyanante/phenol chloroform method (52).

Fifteen or twenty micrograms of total RNA per sample were subjected to electrophoresis on a denaturing 1.2% agarose gel containing 0.22 M formaldehyde in 1×MOPS (10×MOPS: 0.2 M MOPS, 50 mM NaOAc 10 mM EDTA). RNA was blotted on nitrocellulose membrane (MSI Inc., Westboro, Mass.) by overnight capillary transfer in 10×SSC (20×SSC=3M NaCl, 0.3M Na Citrate pH 7.0). The filters were baked at 80° C. under vacuum for 2 hrs and then prehybridized at 42° C. for 4 hrs in hybridization solution consisting of 50% formamide, 5×SSPE (1×SSPE=0.16 M sodium chloride, 50 mM sodium phosphate pH 7.4, 1 mM EDTA), 1% SDS, 5×Denhardt's solution (1×Denhardt's solution=0.02% each of polyvinylpirrolidone, Ficoll and bovine serum albumin), 1 µg/ml poly-A and 100 µg/ml denatured salmon sperm DNA at 42° C. Hybridization was performed overnight at 42° C. in the same solution with $10^6$cpm/ml of random-primed $^{32}$P-labeled GP88 cDNA probe. Filters were washed twice for 25 min at 42° C. in 2×SSC and 1% SDS, followed by two 15 min. washes at 56° C. in 0.2×SSC and 1% SDS. Dried filters were exposed to Kodak XAR-5 film (Kodak, Rochester, N.Y.) at −70° C. with an intensifying screen (Dupont, Boston, Mass.). Results were quantitated by densitometric scanning. Ribosomal protein $L_{32}$ mRNA was detected as internal standard for normalizig RNA loading.

Preparation of Cell Lysate, Immunoprecipitation and Western Blot Analysis

Cells in 10 cm culture dishes were washed once with PBS buffer and lysed on ice for 10 min. with 1 ml PBS buffer containing 1% Triton X-100. Cell lysate was sonicated for 10 seconds on ice, centrifuged at 10,000×g for 10 min., then the supernatant was collected and stored at −70° C. until use.

Amounts of cell lysate and culture medium to be analyzed were normalized by cell number of $18\times10^5$ and $3\times10^5$ respectively. The protease inhibitors: 200 µM PMSF, 1 µM leupeptin, 0.5 µM aprotinin, and 1 µM EDTA were added per sample. Each sample was incubated at 4° C. for 4 hours with 5 µg of affinity purified anti-K19T IgG conjugated to agarose with shaking. Precipitates were collected by centrifugation, washed three times with PBS buffer, resuspended in 20 µl SDS sample buffer containing 5% β-mercaptoethanol, boiled for 5 min., and then separated by SDS-PAGE on 10% polyacrylamide gels according to the method of Laemmli (56). Proteins were electro transferred to immobilon membranes and GP88 detected using anti K19T antibody conjugated to horseradish peroxidase and detected by enhanced chemiluminescence (ECL).

Figure 1B:
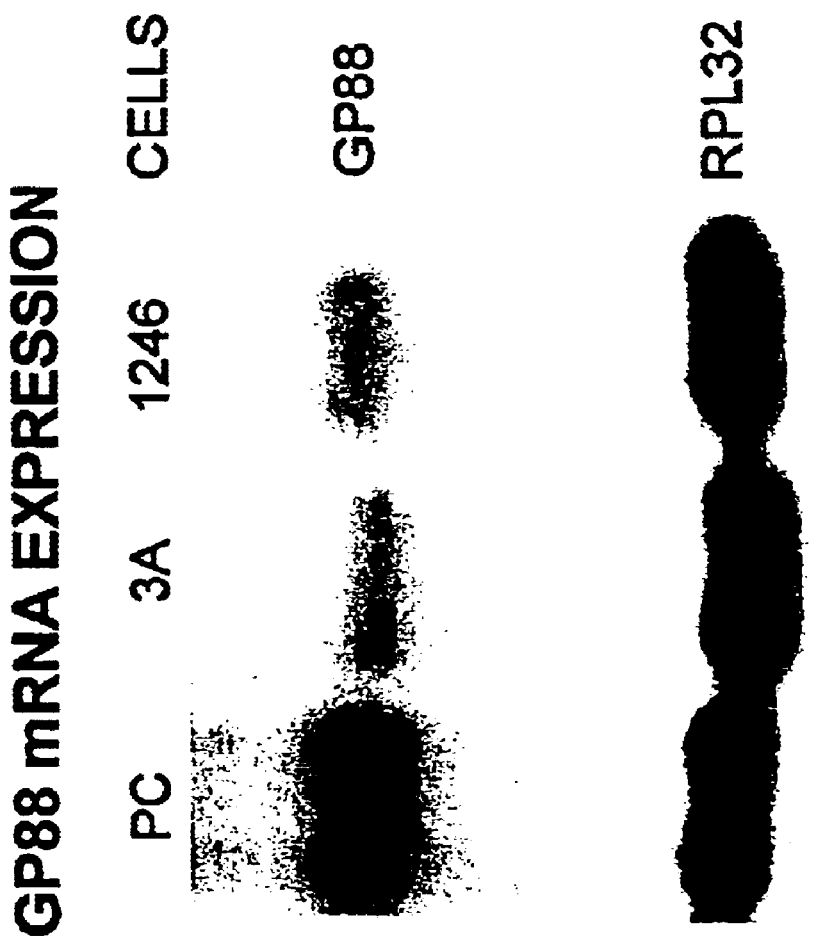
FIG. 1B compares the level of GP88 mRNA expression in the 1246, 1246-3A and PC cell lines. mRNA for RPL32 is used as an internal control for equal amounts of RNA loading.

When expression of GP88 mRNA was investigated in the three cell lines cultivated in DME/F12 medium supplemented with 2% fetal bovine serum (FBS) our laboratory as a probe the results show that the highest level of mRNA expression for GP88 is found in the highly tumorigenic PC cells (FIG. 1B).

The levels of GP88 protein expression were examined by Western blot analyses using anti-K19 antibody both in cell lysates and in culture medium of 1246, 1246-3A and PC cells as described above. As shown in FIG. 1A, the level of GP88 was undetectable in the culture medium of 1246 cells, 3T3, and 124-3A cells and increased dramatically in the culture medium of the highly tumorigenic PC cells. The same results were obtained for GP88 expression in cell lysates.

Figure 1C:
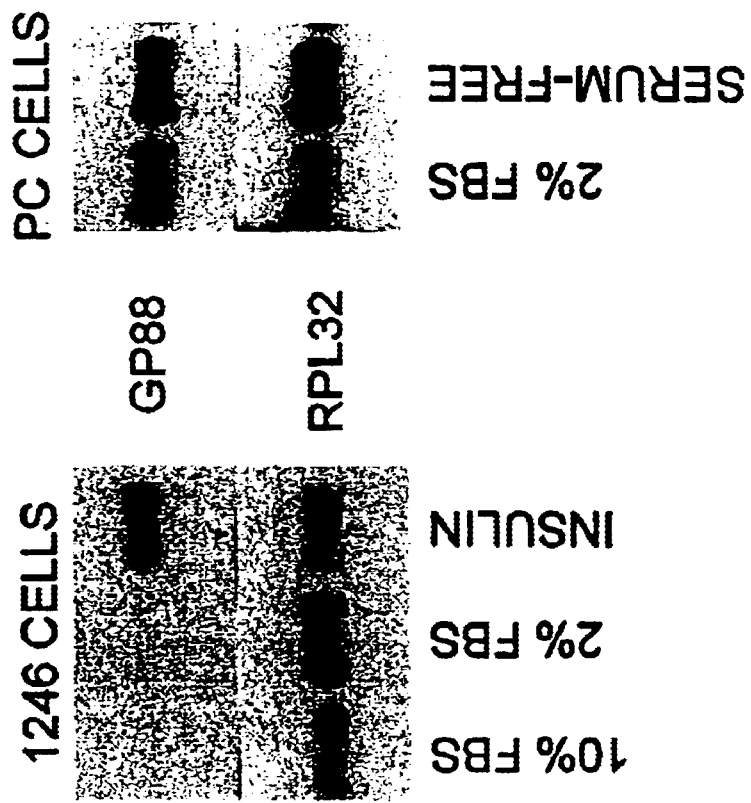
FIG. 1C compares the expression of GP88 mRNA in 1246 cells (left panel) and in PC cells (right panel) in serum-free and serum containing medium. The results show that GP88 expression in 1246 cells is inhibited by the addition of fetal bovine serum whereas such inhibition is not observed in the highly tumorigenic PC cells.

GP88 expression was examined in 1246 cells in different culture conditions such as defined medium and serum containing medium. It was shown that the level of expression of GP88 mRNA (measured by Northern blot analysis) and protein (measured by Western blot analysis) in 1246 and in 1246-3A cells is inhibited when the cells are treated with 2% fetal bovine serum indicating the presence of circulating inhibitors of GP88 expression in fetal bovine serum (FIG. 1C). This inhibition of GP88 expression was also observed when the activity of GP88 promoter linked to a luciferase reporter gene was measured indicating that these inhibitors are effective in inhibiting the transcriptional activity of the GP88 gene. Such inhibitors can be useful to develop GP88 antagonizing agents which will be useful as anti-tumor or antiviral therapy. We have also showed that GP88 mRNA expression is stimulated by EGF in the 1246 cells and by insulin in the human mammary carcinoma cells MDA MB-453.

EXAMPLE 4

GP88 Expression and Biological Activity in Mammary Epithelial Cells (a) Expression of GP88 in Breast Carcinoma Cells.

Experiments were carried out to examine the level of GP88 expression in breast carcinoma and to examine if GP88 is a growth factor for mammary epithelial cells. The rationale in support of this possibility is: GP88 is a potent growth stimulator for mammary epithehal cells (see next paragraph); receptors for GP88 (our studies) and processed form epithelin 1 (54) have been characterized on mammary epithelial cells; breast carcinoma cell lines with different degrees of hormonal dependency are available for study; and lastly there are a growing number of reports emphasizing the importance of the insulin/IGF pathway in the growth control of mammary cells indicating that an escape from this regulation is occurring in malignant breast carcinomas (14, 15). Since PC cells which display an over expression of GP88 are insulin/IGF independent, this would support the rationale of GP88 deregulation in human breast carcinoma.

We have investigated the level of expression of GP88 mRNA in three well studied human breast carcinoma cell lines, MCF-7, which is estrogen receptor positive (ER+), and two cell lines, MDA-MB-453 and 468, being estrogen receptor negative (ER−). MDA-MB468 has also been characterized as having a defective insulin and insuin-like growth factor signaling (53). FIG. 5 shows that GP88 mRNA is expressed in the three cell lines but that the level of expression is higher in the ER-cell lines, MDA-MB-453 and 468, than in the ER+MCF7 cells, indicating that in human breast carcinoma, increased malignancy may be accompanied by increased GP88 expression.

(b) Biological Activity of GP88 in Mammary Epithelial Cells

We investigated the effect of GP88 on the proliferation of a variety of cell lines including fibroblasts and mammary epithelial cells. We have found that GP88 had a profound growth promoting effect on the mouse mammary epithelial cell line C57MG. As shown in FIG. 6, a 5-fold increase in DNA synthesis was observed at a concentration of 150 ng/ml (2 nM) either with GP88 purified from PC cells or with recombinant GP88 expressed in insect cells.

The ability of GP88 purified from PC cells (upper panel) and recombinant GP88, rGP88 (lower panel), to stimulate DNA synthesis in C57MG cells was measured by incorporation of $^3$H-thymidine in serum-starved quiescent cells. Interestingly, in contrast to the growth promoting effect of GP88 on breast epithelial cells, the 6 kDa epithelin 2 (epi 2) has been reported as a growth inhibitor, at least for MDA-MB-468 cells when given at concentrations up to 100 nM (54). These data suggest that the precursor, i.e., GP88, and the processed form, i.e., epi 2, have opposite effects on mammary epithelial cell growth.

EXAMPLE 5

Cloning of GP88 cDNA

GP88 protein purified from PC cell conditioned medium was sequenced after digestion with cyanogen bromide and trypsin. Sequences of N-terminal regions and 6 peptides were obtained (4). Sense and antisense redundant oligonucleotide primers complementary to the obtained amino acid sequences were synthesized and used in the polymerase chain reaction using the touch down PCR method with first strand cDNA of PC cells as template. From the touch down PCR using a primer pair SCV157 and ANG300, a 444 bp amplified product was obtained. This cDNA was then used to screen a lambda-ZAP cDNA library prepared from PC cells in our laboratory. One million unamplified plaques were screened by plaque hybridization with $^{32}$P-labeled PCR generated cDNA fragment. Positive clones were isolated by an additional 3 rounds of plaque purification. Full length GP88 cDNA clone was obtained and sequenced. Full length cDNA was 2137 nucleotides in length with the first ATG located at 23 bp from the 5' end, an open reading frame (ORF) 1770 nucleotides long, and a 3'untranslated region having a polyA tail at position 2127. The sequence was identical to the published mouse granulin (5) except for one nucleotide (T instead of G) at position 1071 of GP88 cDNA (position 1056 of mouse granulin), which resulted in the change of amino acid from arginine to leucine, and a nucleotide substitution at position 1483 with no change in amino acid (FIG. 8). This study demonstrated that GP88 is similar to epithelin/granulin precursor and provided a cDNA to pursue our study of GP88 expression.

EXAMPLE 6

Expression of Mouse GP88 cDNA in Baculovirus

For recombinant GP88 production, the method of choice was to express GP88 in the baculovirus system. A full length GP88 cDNA (obtained by screening PC cell cDNA library) including the signal peptide was ligated into the baculovirus transfer vector pVL1392 (in Vitrogen, San Diego, Calif.). Plasmid pVL1392-GP88 was used to co-transfect Sf9 insect cells with baculovirus DNA. Recombinant viruses encoding GP88 were isolated and plaque purified. For infection and production of recombinant GP88, Sf9 cells were seeded in Grace's medium containing 10% fetal bovine serum (FBS) in T75 cm$^2$ flasks. After infection with recombinant baculovirus-GP88, insect cells were maintained in Grace's medium for 48 hours at 27° C. Conditioned medium was collected by centrifugation and recombinant GP88 (rGP88) was purified by a 2 step purification protocol consisting of heparin-sepharose and immunoaffinity chromatography as described in Example 6. SDS-PAGE analysis of rGP88 indicated that rGP88 migrates faster than PC cell derived GP88 corresponding to an apparent MW of 76 kDa. N-terminal sequencing analysis of rGP88 indicated that it was identical to GP88 purified from PC-CM. The difference of molecular weight between GP88 and rGP88 is due to a difference in glycosylation status of GP88 in insect cells. As shown in FIG. 6, biological activity of rGP88 was identical to that of GP88 purified from PC cells, indicating that the different glycosylation status of GP88 in insect cells and mammalian cells did not affect the biological potency of the protein.

The rGP88 produced from insect cells can be used for biological, and binding studies and to develop monoclonal antibodies to the intact GP88

EXAMPLE 7

Purification of GP8S and Recombinant GP88 by Affinity Chromatography

The conditioned medium (2000 ml) from PC cells was diluted with the same volume of $H_2O$ and loaded on a 2.5 ml heparin-sepharose CL-6B column equilibrated in 10 mM sodium phosphate buffer pH 7.4 containing 75 mM NaCl (Pharmacia, Uppsala, Sweden). The column was washed with at least 10 bed volumes of the same equilibration buffer followed by a wash with 10 mM sodium phosphate buffer containing 0.15 M NaCl. The fraction containing GP88 was eluted with 5 bed volumes of 0.4 M NaCl, 10 mM Tris-HCl, pH 7.5. The eluate was stored at −20° C. for further purification. A synthetic peptide K19T SEQ ID NO: 3 (sequence: KKVIAPRRLPDPQILKSDT) was used to raise the antisera against the GP88 used in the immunoaffinity step. The K19T peptide was linked to CNBr-activated Sepharose 4B according to the method provided by the manufacturer (Pharmacia, Uppsala, Sweden). The specific anti-K19 antibody was purified using the K19T peptide affinity column by elution at acidic pH. Specifically, anti-K19T IgG was applied to a K19T peptide-Sepharose 4B column equilibrated with 10 mM sodium phosphate buffer pH 6.5 (Buffer A) at a flow rate of 0.8 ml/hr, and circulated at 4° C. overnight. After washing the column with 7 ml of Buffer A, the conjugate was eluted with 1 ml of HCl, pH 2.9, then 1 ml of HCl, pH 2.5 at a flow rate of about 0.1 ml/min in a tube containing 0 1 ml of 1M sodium phosphate buffer pH 7.0 to neutralize the pH. The concentration of affinity-purified IgG was determined by the absorbance at 280 nm.

The purified Ab-K19T (1 mg) was then conjugated to 1 ml of agarose beads (Sulfolink coupling gel, Pierce, Rockford, Ill.) using protocols provided by the manufacturer. The final coupled column contained 600 µg anti-K19T/ml gel. The Ab-K19T agarose was packed in a column and washed extensively with PBS. The eluate from heparin sepharose CL-6B column was diluted with 3 volumes $H_2O$ and loaded on the Ab-K19T column. After washing the column with buffer consisting of 750 mM NaCl in 10 mM NaPO4 pH 7.5, the fraction containing GP88 was eluted by elution buffer (150 mM NaCl, pH 2.5 (HCl)). To neutralize, 1/10 volume (v/v) 1 M sodium phosphate pH 6.5 buffer was added to the eluate and the protein concentration was determined by amino acid analysis or micro BCA kit (Bio-Rad, Richmond, Calif.). In general 50 µg of GP88 was purified on a 350 µl column.

This method is also adequate for the purification of recombinant GP88 such as constructed in a baculovirus expression vector and expressed in insect cells. This method is also adequate to purify human GP88 using for the immunoaffinity step human GP88 antibody conjugated to adequate support (sepharose or agarose).

EXAMPLE 8

Development of Neutralizing Antibody for GP88

Peptides corresponding to various regions of mouse and human GP88 were synthesized and conjugated to keyhole limpet Hemocyanin (KLH) by the "glutaraldehyde method." Peptide KLH conjugate was injected into chinchilla rabbits to raise anti-GP88 antibody. Two peptides, K19T and S14R, listed below, were found to generate neutralizing antibodies. Equivalent regions such as E19V of the human GP88 amino acid sequences were used to develop neutralizing anti-human GP88 monoclonal antibodies. Peptides were as follows:

P12T (SEQ ID NO:4) from $P_{208}$ to $T_{219}$ PDAKTQCPDDST
K19T (SEQ ID NO:3) from $K_{344}$ to $T_{362}$ KKVIAPRRLPDPQILKSDT
S14R (SEQ ID NO:5) from $S_{562}$ to $R_{575}$ SARGTKCLRKKIPR
E19V (SEQ ID NO:6) (human GP88) EKAPAHLSLPDPQALKRDV
A14R (SEQ ID NO:7) (human GP88) ARRGTKCLRREAPR Properties of anti-sera are the following:

(1) Anti-K19T, anti-S14R and anti-E19V antibody recognize an 88 kDa GP88 in conditioned medium of cells in culture, in cell lysates and in tissue extracts.

Tissue distribution of GP88 protein expression indicates that it is widely expressed and that most tissues express the unprocessed precursor, i.e., GP88, rather than processed 6 kDa forms, i.e., epi 1 and 2. GP88 is found in senrum (mouse serum contains about 150 ng 88 kDa GP88/ml), and expressed in adipose tissue, in brain (molecular weight varies between 45 and 88 kDa), in testes, in ovary, in liver and in kidney.

(2) Anti-K19T antibody is a neutralizing antibody. Anti-K19T antibody neutralizes the biological effect of GP88 secreted by PC cells which is required for their proliferation. (FIG. 2). Addition of anti-K19T IgG into culture medium of PC cells results in a dose dependent inhibition of PC cell growth. Non-immune IgG had no effect. Inhibition of cell proliferation of cells expressing GP88 has also been obtained using monoclonal antibody K19T for PC cells, rat leukemia cell lines and using monoclonal antibody E19V for neutralizing human GP88 in human breast carcinomas. This demonstrates that the E19V region of human GP88 (and K19T region of mouse GP88) is a region of great biological importance and that any antibody raised against this region will result in obtaining a neutralizing antibody that can be used for therapy of diseases due to increased GP88 expression or increased responsiveness to GP88. The same is true for the S14R region of mouse GP88 and A14R region of human GP88.

(3) Anti E19V monoclonal antibody is a neutrazing antibody. We have shown that at a dose of 100 µg/ml, E19V antibody inhibits the growth of the human breast carcinoma cell line MCF7 by 50% using $^3H$-thymidine incorporation assay as described above for PC cells.

EXAMPLE 9

Growth and Tumorigenic Properties of Cells Transfected With Expression Vector Containing GP88 cDNA in Antisense Orientation The examples above demonstrate that GP88 is overexpressed by the highly tumorigenic PC cell line. Since the cultivation of PC cells in the presence of neutralizing anti-GP88 antibody had resulted in growth inhibition, it indicated that GP88 is required for the growth of PC cells. In order to test whether GP88 overexpression is responsible for the high tumorigenic properties of PC cells in vivo, we examined the growth properties and the tumorigenic ability of PC cells transfected with a cytomegalovirus promoter controlled expression vector containing GP88 CDNA in antisense orientation in order to obtain high levels of antisense RNA transcription. As control, we used PC cells transfected with empty vector.

Figure 7:
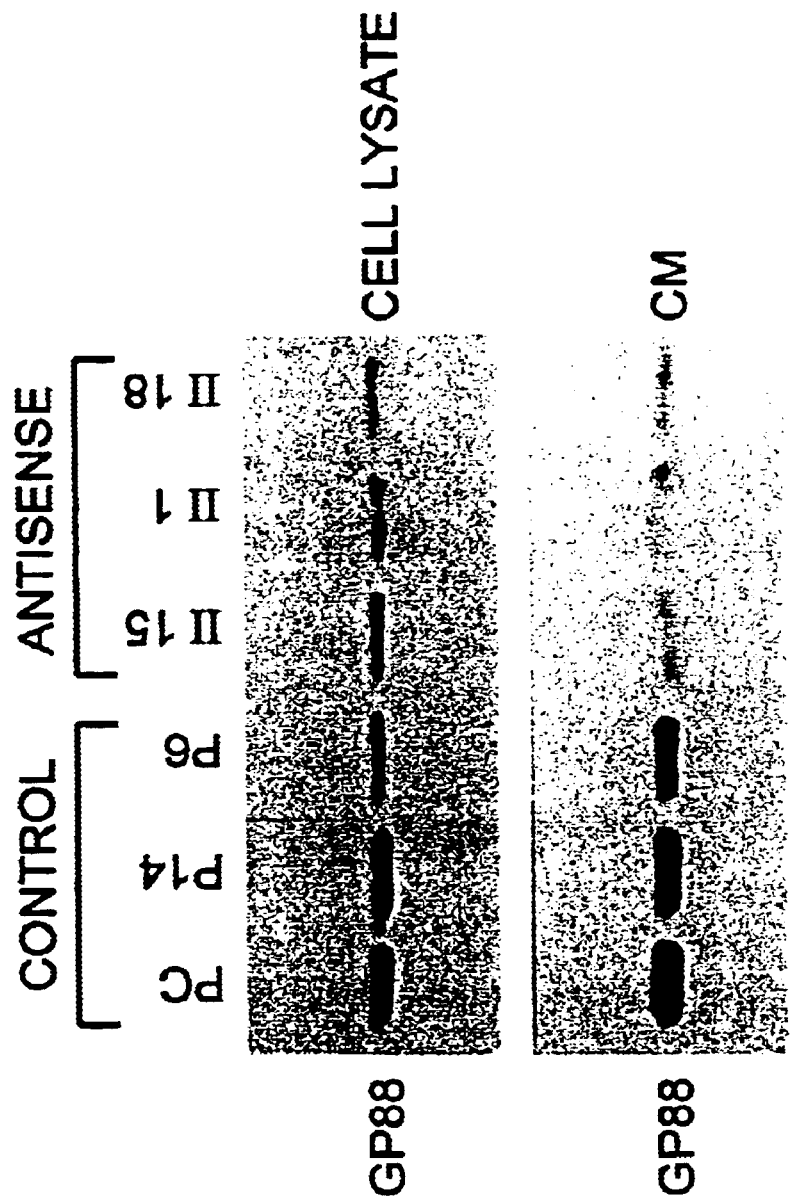
FIG. 7 shows the growth properties and tumorigenic ability of PC cells transfected with a cytomegalovirus promoter controlled expression vector containing GP88 in antisense orientation and PC cells transfected with an empty vector.

A 228 bp fragment of GP88 cDNA was cloned in the antisense orientation in pCMV4 expression vector (Andersson, S., et al, 1989) (51) containing CMV promoter and hGH transcription termination and polyadenylation signals (pCMV4-GP88AS). PC cells were co-transfected with the 20 μg of antisense pCMV4-GP88AS and 2 μg of pRSVneo expression vector containing the neomycin resistant gene by the calcium phosphate method. Control cells were co-transfected with empty pCMV4 vector and pRSV-neo as described above. Transfected cells were selected in the presence of neomycin. Neomycin resistant colonies were cloned and cells were assayed first by detecting the presence of pCMV4-GP88AS by PCR. Twenty-four positive neomycin resistant clones containing the antisense pCMV4-GP88AS were isolated. Nine have been isolated and screened for expression of the antisense transcript. Three clones were further characterized. Western blot analysis of cell lysates and conditioned medium using anti-GP88 antiserum (i.e., anti-K19T antibody) was performed in order to determine the level of GP88 expression in transfected antisense cells and control cells (FIG. 7). Culture medium and cell lysates were prepared by immunoprecipitation with anti-K19T antibody. Protein samples corresponding to $3 \times 10^6$ cells/lane were analyzed by Western blotting with anti-GP88 antibody. The results indicate that GP88 levels are significantly lower in antisense, than in control, transfected cells particularly for AS1 and AS18 clones.

Stable Transfection of Antisense GP8) cDNA Into PC Cells

PC cells were transfected with a 228 bp antisense cDNA fragment of GP88 including start codon region obtained by digesting with Sma I and Xba I GP88 cDNA clone and cloning the obtained cDNA fragment in the antisense orientation into Xba I and Sma I site of the mammalian expression vector pCMV4 as shown in FIG. 11. The stable transfection of PC cells was performed by the Calcium Phosphate method (55) in DME medium (Dulbecco's Modified eagle Medium) containing 3.7 g/L sodium bicarbonate supplemented with 10% FBS. 2–4 hours prior to transfection, a calcium phosphate precipitate was made with 20 μg of plasmid pCMV4 constructed with antisense GP88 cDNA, 2 μg of plasmid carrying neomycin resistance selectable marker (pRSVNEO), and 20 μg of pSK as carrier DNA. After 25 minutes, the precipitate was added dropwise to the cells. After 7 hours, the medium was aspirated and the cells were shocked with 10% DMSO in PBS for 2–3 min., washed twice and fed with complete medium (DME supplemented with 10% FBS). One day after transfection, the cells were split 1:3 and selected for resistance to Geneticin (G-418 Sulphate, Gibco-BRL) at 400 μg/ml. Media was changed 2 days later to remove dead cells and every 3–4 days thereafter. 10–14 days after the 1:3 split, colonies were picked with a cloning ring and transferred into 48 well plate, then passaged into 24 well plate, 12 well plate, and 60 mm dish subsequently. The transfectants were analyzed or frozen. Co-transfection of the empty pCMV4 vector and pRSVNEO was used for raising the empty vector control transfectants.

After being selected by their ability to grow in the presence of Geneticin, the transfected clones were analyzed by two assays as described below:

The presence of the antisense cDNA construct is tested by PCR analysis of genomic DNA of transfected clones using as primers an oligonucleotide located in the CMV promoter (SEQ ID NO: 8) (5'-CCTACTTGGCAGTACATCTACGTA-3') and the other corresponding to the start codon of GP88 cDNA (SEQ ID NO: 9) (5'-CGGAGAATTCAGGCAGACCATGTGGGTC-3'). These primers would amplify a 551 bp DNA fragment from genomic DNA of transfected cells containing the antisense DNA construct described above.

Then, the level of GP88 protein in antisense transfected clones was measured by Western blotting analysis of cell lysates and conditioned media collected from the transfected clones using anti-K19T antibody to measure the efficacy by which the antisense GP88 inhibited the endogenous GP88 protein expression. Antisense clones that showed the highest degree of inhibition of GP88 expression were selected for analysis of their growth properties in vivo as described below. Analysis of GP88 expression in empty vector control transfected clones was done similarly.

The methods used in these various assays will now be described in detail.

PCR Selection of Transfectants

The presence of the antisense construct in the transfected cells was determined by PCR analysis of their genomic DNA using as sense primer SP64 (SEQ ID NO: 8) (5'-CCTACTTGGCAGTACATCTACGTA-3') corresponding to CMV promoter region and antisense primer SP7 (SEQ ID NO: 10) (SEQ ID NO: 10) (5'-CGAGAATTCAGGCAGACCATGTGGGTC-3') corresponding to start codon region of GP88. The sense primer SP647 and antisense primer AP912 (SEQ ID NO: 11) (5'-CTGACGGTTCACTAAACGAGCTC-3') both located in the CMV4 promoter were used to test whether CMV promoter was inserted into the genomic DNA of control transfectants which had been transfected with empty pCMV4 vector.

For extracting genomic DNA for the PCR analysis, the transfectants were lysed by buffer A (100 mM KCl, 10 mM Tris-HCl [pH 8.3], 0.45% Tween 20 and 0.45% NP40) and proteinase K 120 μg/nl, incubated in 60° C. 1 hr, followed by boiling for 15 min. 50–100 ng DNA of each clone was used as template for PCR reaction. Non-transfected PC were used as negative control. Constructed plasmid DNA was used as positive control.

The PCR reaction was performed in 20 μl reaction mixture containing 10 mM Tris-HCl pH 9.0, 50 mM KCl, 1.5 mM MgCl2, 0.1% Triton X-100, 0.2 mM dNTPs, 0.5 units Taq DNA polymerase, 3.2 pMol of each primer, and 50–100 ng of template DNA. The reaction tubes were heated to 95° C. for 3 minutes, and then subjected to 40 cycles of 94° C. for 1 minute, 55° C. for 2 minutes, and 72° C. for 3 minutes with a 10 minutes 72° C. extension in a programmable thermal controller. Products were analyzed on a 1% agarose gel stained with ethidium bromide. The expected size of the amplified fragment corresponding to the presence of the antisense construct with the primers chosen was 551 bp.

Measurement of GP88 Protein Expression in Antisense and Control Transfected Clones The function of transfecting antisense GP88 DNA in the cells is to inhibit endogenous GP88 expression. Therefore, the transfected clones of cells which had been selected by the assays described above (i.e., neomicin resistance and presence of antisense DNA in genomic DNA) were examined to determine the degree of inhibition of endogenous GP88 expression. This was examined by measuring the level of GP88 in cell lysates and in conditioned medium from antisense transfected clones and empty vector transfected control clones by immunoprecipitation and Western blot analysis using anti-K19T antibody by the methods previously described. The transfected clones that displayed the highest degree of inhibition of GP88 expression were further analyzed to examine their growth properties in vitro and in vivo.

Cell Growth Assay

Cells were plated at a density of $3\times10^4$ cells/well (12 well plates, Corning) in 2 ml of DME/F-12 medium (1:1 mixture) supplemented with 2% FBS or 2 µg/ml human fibronectin and 10 µg/ml human transferrin. Five days later, cells were washed with PBS, and cell number per well was determined by counting cells from duplicate wells using Coulter Counter after trypsinization.

The results showed that the antisense GP88 transfected PC clones showed a slower growth when cultivated either in serum containing medium and in defined medium (2F medium) than the empty vector control PC cells cultured under equivalent conditions. These results are in agreement with the fact that GP88 is required by the PC cells to proliferate. Since its expression is inhibited by the antisense, the growth of the antisense transfected cells is inhibited as a result.

Tumorigenicity Assay

Six weeks old female C3H mice were used for tumorigenicity assays. Sense/antisense or control transfectants were injected subcutaneously into syngeneic C3H mice at the density of $10^6$ cells per animal. The appearance and size of tumors were examined. The mice were killed 45–50 days after injection. Tumors were excised, their weight determined and the tumors were quick frozen and kept at −70° C.

In vivo tumorigenicity studies were are carried out by injecting $5\times10^6$ antisense and control cells (transfected with empty vector and nontransfected PC cells) subcutaneously in syngeneic C3H female mice. Mice were observed every day for appearance of tumors by scoring the time of tumor appearance and the size of tumor. After 50 days, mice were killed and blood was collected by heart puncture. Tumors were excised, weighed and either fixed for pathological examination or quick frozen in liquid nitrogen. Other organs of the mice were also collected and examined.

Tumorigenicity for antisense clones and control clones was examined and compared to the wild type PC cells. Table 1 above, shows the results obtained with one of them. FIG. 3 shows the picture of tumor bearing mouse detected with $10^6$ control transfected cells and of mouse injected with antisense clone. Empty vector control transfected clones maintained similar tumorigenic properties as the parent PC cells, whereas no tumor formation was observed in the mice injected with antisense clones. Even after 90 days, these mice still did not present tumors. This experiment was repeated twice. Moreover, additional clones (2 antisense and 2 control) were also examined. The same results were obtained with other antisense clones.

Antisense cDNA for Human GP88

The approach for stable transfection of antisense GP88 cDNA in PC cells described above has also been applied to inhibiting GP88 expression in human breast carcinoma cell lines.

In this case, the human antisense cDNA construct consisted of a 405 bp cDNA fragment inserted in the antisense orientation in the commercially available pcDNA3 mammalian expression vector (In Vitrogen, San Diego, Calif.) which contains pCMV4 cytomagelovirus CMV promoter and neomycin resistant gene so that double transfection of pCMV4 and pRSVneo is not required like the ones described above for PC cells.

To generate the antisense cDNA fragment the following pairs of primers with appropriate restriction enzymes sites were synthesized and used in the PCR reaction:

A-hGP88: SEQ ID NO: 12) 5'-A10GGATCCACGGAGTTGTTACCTGATC-3' (position nt: 362–344)

H-hGP88: SEQ ID NO: 13) 5'-A10GAATTCGCAGGCAGACCATGTGGAC-3' (position nt: −12 to +8)

The amplified cDNA fragment with EcoRI and BamHI restriction sites was inserted in the antisense orientation in the EcoRI and BamHI sites of the pcDNA3 mammalian expression vector. This expression vector construct called pCAS was transfected in the human mammary carcinoma cell line MCF7 and MDA-MB-468 DME-F12 medium supplemented with fetal bovine serum by the calcium phosphate method (55). Selection of transfected cells was done by cultivating the cells in the presence of 800 µg/ml of Geneticin to select cells that are neomicin resistant. Neomicin resistant clones were picked with cloning rings and passaged in medium supplemented with 10% fetal bovine serum (FBS) and with geneticin (800 µg/ml). Transfected clones selected for their resistance to geneticin were further examined by methods similar to the ones described above for PC cells transfected with mouse GP88 antisense cDNA. The presence of the antisense cDNA construct in genomic DNA was checked by PCR analysis using as primers for the PCR reaction T7 primer in the pCDNA3 expression vector and H-hGP88 primer described above. PCR reaction amplified a 420 bp DNA fragment in cells that expressed the transfected human GP88 antisense DNA fragment.

Expression of endogenous GP88 was determined by Western blot analysis of cell lysates and conditioned medium of transfected clones using anti E19V antiserum to select antisense clones with maximum inhibition of GP88 expression. Selected antisense clones were further analyzed to examine their growth properties in vitro and in vivo. Transfection of empty pCDNA3 vector in MCF7 and MDA-MB-468 cells was performed as control for these experiments.

An alternative method to transfection of antisense cDNA is to use antisense oligonucleotides. It is known in the art that sequences around the translation initiation site (ATG encoding the first methionine) provide good sequences for efficient antisense activity. Secondly, sequences with an adequate GC content and that start with either a G or a C have increased efficiency and stability in forming a hybrid with corresponding sense sequence (32, 37, 38). Based on this rationale, it is anticipated that the following two sequences will be efficacious as antisense oligonucleotides to human GP88. The first one is a 22-mer named HGPAS 1 starting 11 nucleotides upstream of the first ATG (methionine codon): HGPAS1 SEQ ID NO: 14) (22): 5'-GGGTCCACATGGTCTGCCTGC-3'. The second oligomer is a 24 mer named HGPAS2 (24) located 21 nucleotides 3' (downstream) of the first ATG: HGPAS2 SEQ ID NO: 15) (24):5'-GCCACCAGCCCTGCTGTTAAGGCC-3'. Other oligonucleotide antisense sequences can be explored by those of ordinary skill given the teachings herein. To judge the efficacy of a sequence to inhibit GP88 expression, oligonucleotides will be added to breast carcinoma cells in culture or any other human cell types under study in increasing doses. Cells will be collected at various time points (12 hours to several days) to measure the level of expression of GP88 protein by Western blot analysis or EIA using an antihuman GP88 antibody, using techniques known to those of ordinary skill in the art. Control cells will be treated with a nonsense or a sense oligomer.

EXAMPLE 10

Inhibition of Tumor Growth in Humans

The present example provides the following:

1) Comparison of the expression of GP88 mRNA and protein in non tumorigenic mammary epithelial cells MCF10A and in malignant MCF7 and in MDA-MB-468 cells.

2) Growth of malignant MCF7 and MDA-MB-468 cells in the presence of neutralizing anti-human GP88 antibody (anti-human E19V monoclonal antibody) leads to inhibition of proliferation of cells.

3) Proliferation in vitro and tumorigenicity in vivo of human breast carcinoma cells are inhibited by inhibiting GP88 expression by antisense GP88 DNA.

Comparison of GP88 Expression in Non Tumorigenic Human Mammary Epithelial Cells and in Tumorigenic Breast Carcinoma Cell Lines We investigated the expression of GP88 mRNA and protein in three human breast cell lines: The MCF10A cell line, which is a non tumorigenic human mammary epithelial cell line, and in two human breast carcinoma cell lines, MCF7 which is estrogen receptor positive and MDA-MB-468 which is estrogen receptor negative.

Expression of GP88 mRNA expression was done by Northern blot analysis of total RNA extracted from these cell lines using a radiolabeled human GP88 cDNA probe. Expression of GP88 protein was measured by Western blot analysis of immunoprecipitated GP88 using either rabbit anti-human GP88 polyclonal antibody or the anti-human E19V monoclonal antibody. This latter antibody was developed by immunizing mice with human peptide E19V conjugated to protein as described in Example 8.

Anti-human GP88 antibodies that we have now at our disposal are: polyclonal antihuman GP88 antibody developed in rabbits using as antigen a 37 kDa fragment of human GP88 expressed as a histidine tagged protein in bacteria, and the anti-human GP88 antibody (polyclonal and monoclonal) developed by using as antigen E19V peptide conjugated to keyhole limpet hemocyanin. Development of these antibodies (polyclonal and monoclonal) are described above. All of these antibodies can be used for immunoprecipitation and Western blot analysis of human GP88 in human tissues and cells.

Figure 14:
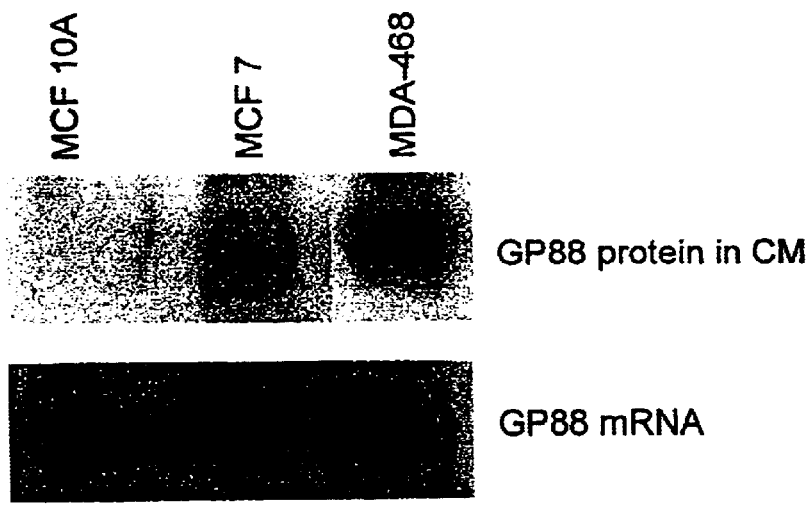
FIG. 14 shows GP88 expression levels in non-tumorigenic MCF 10A and in malignant (MCF 7, MDA-468) human mammary epithelial cells.

The Northern blot analysis shows that the expression of GP88 mRNA in the non tumorigenic MCF10A cells is very low and increases at least 5–10 times in the human breast carcinoma cell lines MCF7 and MDA-MB-468 (FIG. 14).

The results of the Western blot analysis of the three cell lines show that GP88 protein expression is undetectable in culture medium (CM) collected from the non-tumorigenic MCF10A cells, whereas it increased 10–20 times in media conditioned by the MCF7 cells and by the MDA-MB-468 cells. In addition to being secreted in the culture medium of the breast carcinoma cells, GP88 protein is also expressed at high levels in cell lysates of the maligant cells, whereas it is undetected in the non tumorigenic MCF10A cells.

These data confirm that human breast carcinoma cells overexpress GP88 when compared to non tumorigenic human mammary cells.

Inhibition of Growth of Malignant MCF7 and MDA-MB-468 Cells in the Presence of Neutralizing Anti-human GP88 Antibody (Anti-human E19V Monoclonal Antibody)

Experiments were carried out in which human breast carcinoma MCF7 cells were incubated with different doses of anti-human GP88 monoclonal antibody (anti-E19V peptide IgG fraction). Proliferation was measured by [$^3$H] thymidine incorporation into DNA. Control cells consisted of cells incubated with the same amount of unrelated mouse IgG. Results show that incubation of MCF7 cells with 25 μg/ml of anti-GP88 monoclonal antibody leads to a 50% inhibition of thymidine incorporation, whereas 100 μg/ml resulted in an 80% inhibition of proliferation. Similar results were found as indicated above for MDA-MB-468 cells. These data again confirm that (i) anti-human E19V antibody neutralizes human GP88, and (ii) malignant human cells which secrete high levels of GP88 in culture medium and which require GP88 to proliferate can be effectively inhibited by treatment with anti-human GP88 neutralizing antibody, thus demonstrating that inhibition of GP88 action on tumor cells is an effective therapy for inhibiting tumor growth of cells overexpressing GP88.

Figure 15:
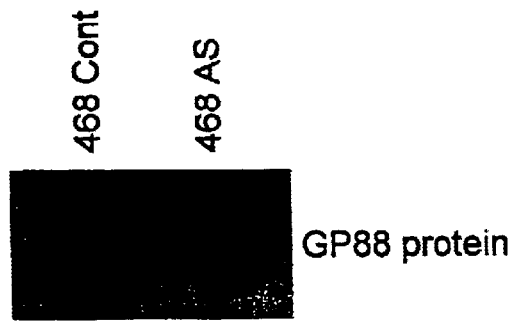
FIG. 15 shows that GP88 expression is inhibited by antisense GP88 cDNA transfection in human breast carcinoma MDA468 cells.

Proliferation in vitro and Tumorigenicity in vivo of Human Breast Carcinoma Cells are Inhibited by Inhibiting GP88 Expression by Antisense GP88 DNA Human breast carcinoma MDA-MB-468 cells were stably transfected with antisense human GP88 cDNA construct (405 bp fragment inserted into pCDNA3 expression vector). This construct is described in Example 9. Stable antisense clones were isolated and characterized. In particular, antisense clones were selected based on the fact that expression of GP88 was effectively inhibited. This was determined by measuring GP88 expression in antisense cells and empty vector control cells by Western blot analysis of cell extracts and conditioned medium using antiGP88 antibody. Several clones were obtained and characterized. Similar results were obtained with all antisense clones isolated. Data presented here concern one antisense clone called 468AS. As shown in FIG. 15, transfection of antisense GP88 cDNA in MDA-MB-468 cells (468AS) resulted in inhibition of GP88 protein expression when compared to empty vector control MDA-MB-468 cells (468 Cont).

Measurement of the proliferation rate of antisense GP88 and empty vector control cells indicated that antisense cells had an 80% inhibition of cell proliferation when compared to the empty vector transfected cells. Our data with all the clones analyzed also showed that the extent of growth inhibition was directly correlated to the degree of inhibition of expression of GP88 in the antisense clones.

Antisense human breast 468AS cells which displayed the highest inhibition of GP88 expression, and empty vector control (468 Cont) cells were injected subcutaneously into female nude mice in the breast area at a density of $2 \times 10^3$ cells/mouse using 4 mice per cell line. Tumor appearance was monitored by visually inspecting the mice. After 4 weeks, the mice were sacrificed, tumors were excised and weighed (see Table 3 below).

TABLE 3

Effect of inhibition of GP88 expression by antisense GP88cDNA transfection on tumor growth of human breast cancer cells MDA-MB-468 in nude mice

| Cells | Mice bearing tumors | Weight of tumors (g) |
|---|---|---|
| 468 Cont empty vector | 4/4 | 0.2 ± 0.06 |
| 468AS antisense GP88 | 3/4 | 0.05 ± 0/025** |

(**p ≧ 0.01 significant)

The results show that inhibition of GP88 expression resulted in a 75% inhibition of tumor growth for human breast carcinoma cells.

This experiment demonstrated that inhibition of GP88 expression in human breast carcinoma cell lines leads to inhibition of tumorigenicity.

EXAMPLE 11

Diagnostic Test for Tumorigenicity

In teratoma and in breast cancer, an increase in tumorigenic properties is associated with an increase in GP88 expression or an increase in GP88 responsiveness.

Moreover, FIG. 4 shows that the level of expression of GP88 in tumor tissue is increased when compared to the surrounding tissues. Accordingly, increase of GP88 level can be used as a diagnostic approach to detecting tumor. In human tumor biopsies, a change (increase) in GP88 expression when compared to the level of GP88 in normal corresponding tissues is indicative of the state of tumorigenicity or malignancy of the tissue biopsy analyzed. Increase in expression of GP88 can be measured at the mRNA level or at the protein level. GP88 mRNA expression can be measured either by Northern blot analysis, RNAse protection assay or RT-PCR.

GP88 protein expression is quantitated by ELISA, EIA or RIA using an anti-GP88 antibody.

The ability to measure GP88 expression in tissue extracts in comparison to corresponding tissues from normal subject can be used to predict the degree of tumorigenicity of a particular cancer or to determine whether this particular cancer will be responsive to anti-GP88 therapy.

For diagnosis of diseases associated with increase in GP88 responsiveness, tissue biopsies to be analyzed will be treated with anti-GP88 neutralizing antibodies or anti-GP88 receptor antibodies to see if such treatment inhibits growth of the cells. Alternatively, the ability of GP88 antisense oligonucleotides to inhibit growth indicates that expression of GP88 is required for growth in vivo.

EXAMPLE 12

Characteristics of GP88 Cell Surface Receptors

Binding of iodinated GP88 to a variety of cell lines CCL64, 1246, PC and the mammary epithelial C57MG was determined in order to examine the biochemical characteristics of GP88 cell surface receptors using the methods described below. For these studies we used affinity purified recombinant GP88 (rGP88) from the culture medium of baculovirus infected SF9 insect cells as ligand. Methods to prepare rGP88 have previously been described.

a) Iodination of GP88.

Recombinant GP88 (rGP88) was iodinated by the chloramine T method at 4° C. Other known methods can also be applied. Briefly, 1 µg of GP88 was incubated for 2 min with $^{125}$I Na (100 µCi) that had been preincubated for 90 seconds with 2 µg chloramine T. The reaction was quenched with the addition of 100 µl saturated tyrosine, 10 µl of a 1% solution of bovine serum albumin (BSA) and 2 µg of sodium metabisulfite. After addition of 100 µl PBS, the iodinated protein was separated from free Na$^{125}$I by gel filtration on a Sephadex-G50 column that had been preincubated with PBS containing 1% bovine serum albumin and then extensively washed with PBS to reduce non-specific binding. The labeled proteins were eluted with PBS and fractions monitored for radioactivity. Amount of incorporated radioactivity was estimated by TCA precipitation. Specific activity of 125I-GP88 was typically 30–50 µCi/µg. This method and other methods for iodination of proteins are well known to people skilled in the art can also be used to iodinate PC derived GP88 rather than rGP88 or any derivatives thereof.

b) $^{125}$I-GP88 Binding.

The example provided here describes binding assay with the mink lung epithelial cell line CCL64 but has also been applied to several cell lines including the 1246, PC cell lines and the mammary epithelial cell line C57MG. The binding assays were performed on cell suspension. CCL64 cells were cultivated as monolayer in DME medium supplemented with 10% fetal bovine serum (FBS) until they reached confluency. At that time, cells were washed with PBS and detached by incubation with a solution of 0.25 mg/ml of trypsin and 1 mM EDTA. The cells were harvested by centrifugation, washed with culture medium and counted with a hemocytometer. For binding assays, 10$^6$ cells were resuspended in 500 µl of binding buffer consisting of DME medium supplemented with 1% bovine serum albumin in 1.5 ml ependorf tubes and incubated for 2 hours at 25° C. with 10$^5$ cpm of $^{125}$I-rGP88 and increasing concentrations of cold rGP88 from 1 to 100 ng/ml. Binding was stopped by centrifuging the cells followed by 3 successive washings at 4° C. with cold binding buffer followed by centrifugation. Cell pellets were counted with a gamma counter. Scatchard analysis of binding data was carried out by computer Ligand program. Values correspond to the average of three separate experiments with duplicate determinations per experimental point.

Scatchard analysis of binding of $^{125}$I-GP88 to CCL64 cells was curvilinear corresponding to the presence of two classes of cell surface receptors: a high affinity class with a Kd of $4.3 \pm 1.5 \times 10^{-11}$ M, 560±170 sites/cell and a low affinity class of receptors with a Kd of $3.9 \pm 1.9 \times 10^{-9}$ M, 17,000±5900 sites/cell.

c) Cross-linking Studies of $^{125}$I-GP88 to CCL64 and Other Cell Lines.

Cross-linking of $^{125}$I-GP88 to cell surface receptors was carried out using disuccinimidyl suberate (DSS). For cross-linking studies, 5×10$^5$ cells were suspended in 250 µl of binding buffer in eppendorf tubes. $^{125}$I-GP88 was added in 50 µl of binding buffer (DME medium with 1% BSA) with or without 100 fold excess unlabeled GP88 ligand. Binding was performed as described in the previous paragraph. At the end of the incubation period, the cells were washed one time with 0.2% BSA-DME and one time with PBS before cross-linking was carried out. Dissucinimidye suberate (DSS) was dissolved in DMSO at a 100 mM just prior to use. The cells were resuspended in 200 µl PBS containing 1 mM disuccinimidyl suberate (DSS,) at room temperature for 15 min. After cross-linking, the cells were centrifuged, washed and extracted with 25 µl extraction buffer (PBS containing 1% Triton X-100, 0.1% SDS, 0.5 mM phenylmethylsulfonyl fluoride (PMSF at 4° C. Samples were centrifuged for 5 min at 13,000×g and 25 μl of supernatant from each sample was mixed with 4 μl of 20% SDS and 15 μl 3×Laemmli's sample buffer (56) containing b-mercaptoethanol and boiled for 5 min. Electrophoresis of samples was carried out on 7% SDS polyacrylamide slab gel according to Laemmli (56) using a minigel apparatus (Bio-Rad, Richmond, Calif.). The dried gels were exposed to X-ray films for autoradiography at −70° C.

Figure 12:
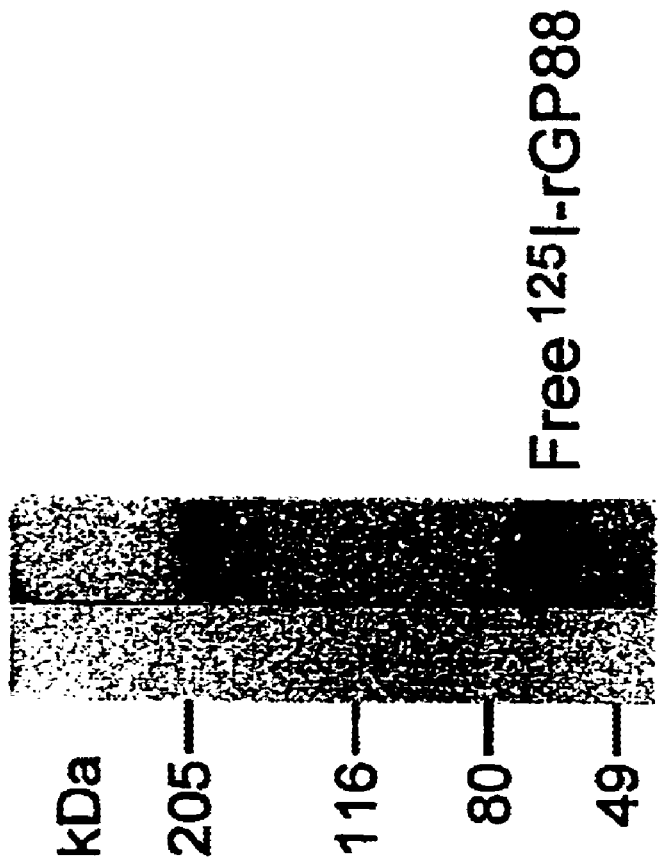
FIG. 12 shows the cross-linking of $^{125}$I-rGP88 to GP88 cell surface receptors on CCL-G64 cells. The cross-linking reaction was carried out with disuccinimidyl suberate (DSS). Reaction products were analyzed by SDS-PAGE on a 7% polyacrylamide gel.

As shown in FIG. 12, autoradiographic analysis revealed the presence of one major cross-linked band with a molecular weight of 190–195 kDa. This would correspond to a molecular weight for the unbound receptor of about 110 kDa for the major band. The intensity of the major cross-linked band was decreased in the lanes where binding was carried out in the presence of excess cold GP88. Cross-linked band could not be detected if experiment and gel electrophoresis was performed in the absence of DSS. Additional experiments using samples treated or not with β-mercaptoethanol prior to performing the electrophoresis indicated that the cell surface receptors for epithelin/granulin precursor are monomeric.

Figure 13:
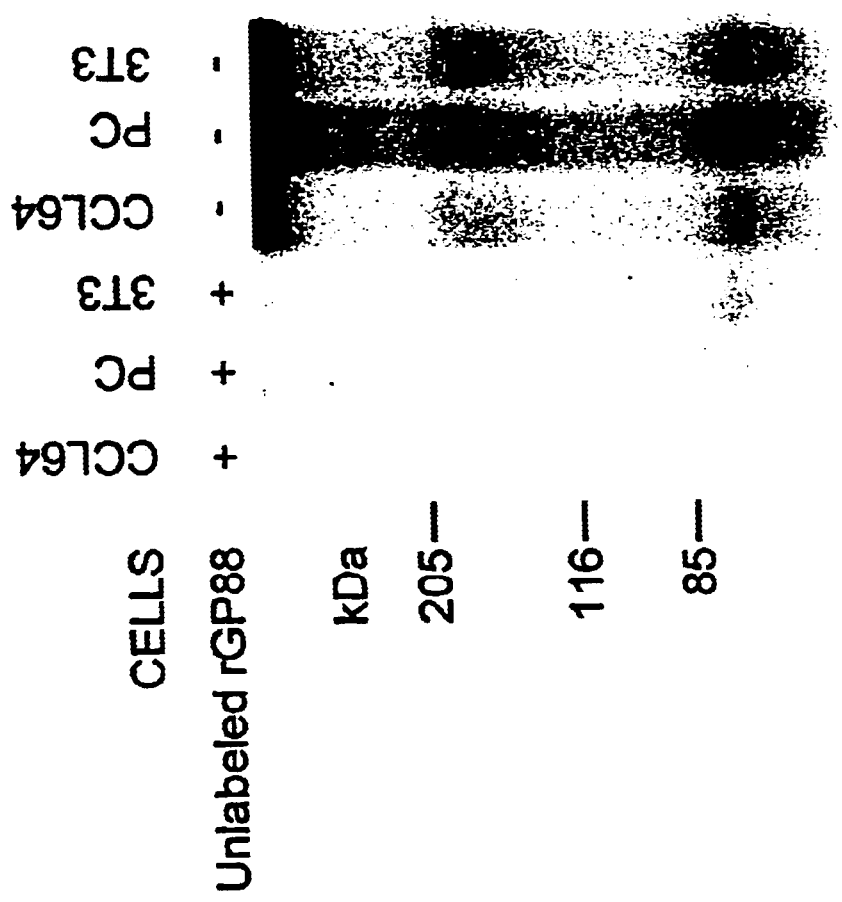
FIG. 13 shows the cross-linking of $^{125}$I-rGP88 to GP88 cell surface receptors on 3T3 fibroblasts, PC cells and C57MG mammary epithelial cells. The results show that these various cell lines display GP88 cell surface receptors of similar molecular weight as the ones on CCL64 cells (FIG. 12).

Cross-linking of $^{125}$I-GP88 to cell surface receptors were also carried out with 3T3, PC cells and the mammary epithelial cells C57MG by the same method. The results of these experiments indicated similar cross-linking pattern for GP88 in all cell lines tested suggesting the presence of cell surface binding sites with similar size in fibroblastic and epithelial cells (FIG. 13)

GP8S Mediated Signal Transduction in Mammary Epithelial Cell Line C57MG

Experiments to determine the characteristics of the signal transduction pathway activated by GP88 after binding to its cell surface receptors were carried out with GP88 in the mammary epithelial cell line C57MG. We have shown that anti-K19 T antibody can immunoprecipitate the complex formed by GP88 and its cell surface receptors on various cell types and in the mammary epithelial cells C57MG in particular. This feature has allowed us to further characterize biochemical properties of GP88 receptor and the signal transduction it mediates leading to growth stimulation. We have shown that GP88 receptors belong to the tyrosine kinase family of receptors. Upon binding of GP88 to its cell surface, GP88 receptor is activated by phosphorylation on tyrosine residues resulting in phosphorylation of several signaling molecules including IRS-1, SHC, Grb2 and leading to activation of MAP kinase ERK-2.

Having now fully described this invention, it will be appreciated by those skilled in the art that the same can be performed within a wide range of equivalent parameters concentrations and conditions without departing from the spirit and scope of the invention and without undue experimentation.

REFERENCES

1) Alberts, B., Bray, D., Lewis, J., Raff, M., Roberts, K, Watson, J. D., 1983 Molecular Biology of the Cell. Garland Publishing Inc. NY.
2) Cross, M and Dexter, T (1991) Growth Factors in development, transformation and tumorigenesis. Cell, 64, 271–280.
3) Sporn, M. B. and Todaro, G. J. (1980) Autocrine secretion and malignant transformation. New. Engl. J. Med. 303, 878–880.
4) Zhou, J., Gao, G., Crabb, J. W. and Serrero, G. (1993) Purification of an autocrine growth factor homologous with mouse epithelin precursor from a highly tumorigenic cell line. J. Biol. Chem. 268, 10863–10869.
5) Plowman, G. D., Green, J. M. Neubauer, M. G., Buckley, S. D., McDonald, V. L., Todaro, G. J., Shoyab, M. (1992). The epithelin precursor encodes two proteins with opposing activities on epithelial cell growth. J. Biol. Chem. 267, 13073–13078.
6) Bateman, A., Belcourt, D., Bennett, H., Lazure, C. and Solomon, S. (1990) Granulins, a novel class of peptide from leucocytes. Biochem. Biophys. Res. Commun. 173, 1161–1168.
7) Nestor, J J Jr. Newman, S R, DeLustro, B., Todaro, G J, Schreiber, A B, 1985, A synthetic fragment of rat transforming growth factor alpha with receptor binding and antigenic properties. Biochem. Biophys. Res. Commun. 129, 226–232.
8) Adelman, J P, Hayflick, J S, Vasser, M, Seeburg, P H (1983) In vitro deletional mutagenesis for bacterial production of the 20,000 dalton form of human pituitary growth hormone. DNA, 2, 183–193.
9) Serrero, G. and J. C. Khoo (1982) An in vitro model to study adipose differentiation in serum-free medium. Anal. Biochem. 120:351–359.
10) Serrero, G. (1984). Study of a teratoma-derived adipogenic cell line 1246 and isolation of an insulin independent variant in serum-free medium. In: Hormonally Defined Media, a Tool in Cell Biology, (G. Fisher and R. J. Wieser, eds.), Springer-Verlag, New York Berlin, Heidelberg, Tokyo, pp. 310–313.
11) Serrero, G. (1985) Tumorigenicity associated with loss of response to insulin and of differentiation ability in the adipogenic cell line 1246. In Vitro Cell. Devel. Biol. 21:537–540.
12) Serrero, G., Zhou, J., Mills, D. and lepak, N. (1991) Decreased transforming growth factor β response and binding in insulin-independent, teratoma-derived cell lines with increased tumorigenic properties. J. Cell Physiol. 149 503–511.
13) Arteaga, C. L. (1992) Interference with the IGF system as a strategy to inhibit breast cancer growth. Breast Cancer Res. Treat 22, 101–106.
14) Arteaga, C. L., and Osborne, C. k. (1989) Growth inhibition of human breast cancer cells in vitro with an antibody against the type 1 somatomedin receptor. Cancer Res. 49, 6237–6241.
15) Schofield, P N, Granerus, M, Tally, M, Engstrom, W (1994) The biological effects of a high molecular weight form of IGF-II in a pluripotential human teratocarcinoma cell line. Anticancer Res. 14, 533–538.
16) Trojan, J, Johnson, T R, Rudin, S D, Blossey, B K, Kelley, K M, Shevelev, A, Abdul-Karim, F W, Anthony, D D, Tykocinsid, M L, Ilan, J et al (1994) Gene therapy of murine teratocarcinoma: separate functions for insulin-like growth factors I and II in immunogenicity and differentiation. Proc. Natl. Acad. Sci. USA 91, 6088–6092.
17) Trojan, J, Johnson, T R, Rudin, S D, Ilan, J, Tykocinski, M L, Ilan, J (1993) Treatment of rat glioblastomas by immunogenic C6 cells expressing antisense insulin-like growth factor I RNA. Science, 259, 94–97.
18) Kohler, G and Milstein, C. 1975: Continuous culture of fused cells secreting antibody of predefined specificity. Nature 256, 495–497.
19) de St. Groth, F. and Scheidegger, D. (1980) Production of monoclonal antibodies. Strategy and tactics. J. Immunol. Methods. 35 1–21.
20) Harlow, E. and Lane D. (1988) Antibodies. A laboratory manual. Cold Spring Harbor Laboratory. Cold Spring Harbor, N.Y.

21) Cadilly, S., Riggs, A D., Pande, H., Shively, J. E., Holmes, W. E., Rey. M. Perry, L. J., Wetzel, R., Heyneker, H. L. (1984) Generation of antibody activity from immunoglobulin polypeptide chains produced in Escherichia Coli. Proc. Natl. Acad. Sci. USA. 81, 3273–3277.

22) Morrison S L, Johnson, M J., Herzenberg, L A, Oi, V T (1984) Chimeric human antibody molecules: mouse antigen-binding domains with human constant region domains. Proc. Natl. Acad. Sci USA. 81, 6851–6855.

23) Liu, A Y, Robinson, R R, Hellstrom, K E., Murray, E D Jr., Chang, C P, Hellstrom, T. (1987) Chimeric mouse-human IgG antibody that can mediate lysis of cancer cells. Proc. Natl. Acad. Sci. USA 84, 3439–443.

24) Better, M, Chang, C P, Robinson, R R Horwitz, A H. 1988. Escherichia Coli secretion of an active antibody fragment. Science, 240, 1041–1043.

25) Riechmann, L., Clark, M., Waldmann, H. and Winter, G. (1988) Reshaping human antibodies for therapy. Nature, 332, 323–327.

26) Baca, M., Presta, L. G., O'Connor, S. J., Wells, J. A. (1997) Antibody humanization using monovalent phage display. J. Biol. Chem. 272, 10678–10684.

27) Rosok, M. J., Yelton, D. E., Harris, L. J., Bajorath, J., Hellstrom, K-E., Hellstrom, I., Cruz, G. A, Kristensson, K, Lin, H., Huse, W. D., and Glaser, S. M. (1966) A combinatorial library strategy for the rapid humanization of anticarcinoma BR96 Fab. J. Biol. Chem. 271, 22611–22618.

28) Wahl, R. L., Parker, C. W., Philpott, G. W., J. Nucl. Med. 1983, 24, 316–325 Improved radioimaging and tumor locations with monoclonal F(ab')2.

29) Mulshine, J. L., Avis, I., Treston, A. M., Mobley, C., Kaspryzyk, P., Carrasquillo, J. A., Larson, S. M., Nakanishi, Y., Merchant, B., Minna, J. D., et al (1988) Clinical use of a monoclonal antibody to bombesin-like peptide in patients with lung cancer. Ann. NY Acad. Sci. 547, 360–372.

30) Munroe, S. H., 1988, EMBO. J. 7:2523–2532 Antisense RNA inhibits splicing of prem-RNA in vitro.

31) Mullis, K B, Faloona, F A (1987) Specific synthesis of DNA in vitro via polymerase catalyzed chain reaction. Met. Enzymol. 155, 335–350.

32) Mercola, D., and Cohen, J. S. (1995) Antisense approaches to cancer gene therapy. Cancer Gene Therapy 2 47–59.

33) Wagner, R. W. (1994) Nature, 372, 333–335 Gene Inhibition using antisense aligodeoxy-nucleotides.

34) Wagner, R. W. (1995) The state of the art in antisense research. Nature Medicine 1, 111–1118.

35) Sambrook et al. Molecular Cloning. A Laboratory Manual. Cold Spring Harbour, N.Y. (1989)

36) Brysch, W. and Schlingensiepen, K H. (1994) Design and application of antisense oligonucleotides in cell culture, in vivo and as therapeutic agents. Cell Mol. Neurobiol. 14, 557–568.

37) Helene, C (1991) Rational design of sequence-specific oncogene inhibitors based on antisense and antigene nucleotides. Eur. J. Cancer 27, 1466–1471.

38) Giles, R. V., Spiller, D. G., Green, J. A., Clark, R. E. and Tidd, D. M. (1995) Optimization of antisense oligodeoxynucleotide structure for targeting bcr-abl mRNA. Blood 86, 744–754.

39) Thaler, D. S., Liu, S. and Tombline, G. (1996) Extending the chemistry that supports genetic information transfer in vivo: phophorothioate DNA, phosphorothioate RNA, 2-O-methyl RNA and methylphosphonate DNA Proc. Natl. Acad. Sci. USA. 93, 1352–1356.

40) Gryaznov, S., Skorski, T., Cucco, C., Nieborovska-Skorska, M., Chiu, C. Y., Lloyd, D., Chen, J. K, Koziolkiewicz, M. and Calbretta, B. (1996) Oligonucleotide N3'->P5' phosphoramidates as antisense agents. Nucleic Acid Res. 24, 1508–1514.

41) Lappalainen, K, Urtti, A., Soderling, E., Jaaskelainen, I., Syrjanen, K and Syrjanen, S. (1994) Cationic liposomes improve the stability and intracellular delivery of antisense oligonucleotides into CaSki cells. Biochim. Biophys. Acta 1196, 201–208.

42) Ensoli, B. et al. (1994) Block of AIDS-Kaposi's sarcoma K S cell growth, angiogenesis and lesion formation in nude mice by antisense oligonucleotide targeting basic fibroblast growth factor. A novel strategy for the therapy of K S. J. Clin. Inves. 94, 1736–1746.

43) Peng, B., Methta, N H., Fernandes, H., Chou, C C. and Raveche, E. (1995) Growth inhibition of malignant CD5+B (b-1) cells by antisense IL-10 oligonucleotide. Leukemia Res. 19 159–167.

44) Glick, B. R. (1987) J. Ind. Microbiol, 1:277–282.

45) Cenatiempo, Y., (1986) Biochimie, 68:595–516 Prokaryotic gene expression in vitro: transcription-translation coupled systems.

46) Gottesman, S (1984) Ann. Rev. Genet. 18:415–442 Bacterial regulation: global regulatory networks.

47) Hamer, D. H. and Walling, M., 1982, J Mol Appli. Gen. 1:273–288 Regulation in vivo of a closed mammalian gene: cadmium induces the trancription of a mouse metallothionein gene in SV40 vectors. 48) McKnight, S., 1982, Cell, 31: 355–365 Functional relationships between transcriptional control signals of the thymidine kinase gene of herpes siplex virus.

49) Johnston, S. A. and Hopper, J. E. 1982 Proc. Natl. Acad. Sci. USA, 79, 6971–6975 Isolation of the yeast regulatory gene, GAL4 and analysis of its dosage effects on the galactose/melibiose regulon.

50) Benoist, C., and Chambon, P., 1981 Nature, 290:304–310 In vivo sequence requirements of the SV40 early promoter region.

51) Andersson, S., Davis, D. L., Dahlback, H., Jornvalif, H. and Russell, D. W. 91989) Cloning, Structure and Expression of the Microchondrial cytochrome P450 sterl 26 hydroxylase a bile acid biosynthetic enzyme, J. Biol. Chem. 264, 8222–8229.

52) Chomczinski, P, Sacchi, N (1987) Single-step method of RNA isolation by acid guanidinium thiocyanate-phenol-chloroform extraction. Anal. Biochem. 162, 156–159.

53) Sepp-lorenzino, L., Rosen, N., Lebwohl, D. E. (1994) Inslin and insulin-like growth factor signaling are defective in the MDA-MB-468 human breast cancer cell line. Cell Growth Diff. 5, 1077–1083.

54) Culouscou, J-M., Carlton, G. W., and Shoyab, M. (1993) Biochemical analysis of the epithelin receptor. J. Biol. Chem. 268, 10458–10462.

55) Ausubel, F. M., Brent, R. E., Moore, D. D., Smith, J. A., Seidman, J. G., and Struhl, K. (1987). Current Protocols in Molecular Biology, Greene Publishing and Wiley Interscience, New York.

56) Laemmli. UK (1970) Cleavage of structural proteins during assembly of the head of bacteriophage T4. Nature, 227, 680–685.

57) Siegall, C. B. 1994 Targeted Toxins as Anticancer Agents, Cancer, 74 1006–1012.

What is claimed as new and desired to be protected by Letters Patent is:

1. A method for diagnosing tumorigenicity comprising: measuring the expression or level of the full-length protein encoded by SEQ ID NO: 16 in a tissue specimen or biological fluid; measuring the expression or level of said protein in corresponding normal or peripheral tissue; and diagnosing tumorigenicity by determining whether the measured expression or level of said protein in said tissue specimen or biological fluid is higher than in corresponding normal or peripheral tissue by an amount sufficient to indicate tumorigenicity.

2. The method according to claim 1 wherein said protein level is measured with an anti-GP88 antibody.

3. The method according to claim 2 wherein said anti-GP88 antibody is humanized.

4. The method according to claim 2 wherein said anti-GP88 antibody is produced in an animal immunized with a composition comprising SEQ ID NO: 3.

5. The method according to claim 2 wherein said anti-GP88 antibody is produced in an animal immunized with a composition comprising SEQ ID NO: 4.

6. The method according to claim 2 wherein said anti-GP88 antibody is produced in an animal immunized with a composition comprising SEQ ID NO: 5.

7. The method according to claim 2 wherein said anti-GP88 antibody is produced in an animal immunized with a composition comprising SEQ ID NO: 6.

8. The method according to claim 2 wherein said anti-GP88 antibody is produced in an animal immunized with a composition comprising SEQ ID NO: 7.

9. The method according to claim 2 wherein said anti-GP88 antibody is produced in an animal immunized with a composition comprising SEQ ID NO: 6.

10. The method according to claim 1 wherein said protein expression or level is measured by immunoassay.

11. The method according to claim 10 wherein said immunoassay is an enzyme-linked immunoassay.

12. The method according to claim 10 wherein said immunoassay is a radioimmunoassay.

13. The method according to claim 1 wherein said tissue specimen is human tissue or human biological fluid.

14. The method according to claim 1 wherein said normal or peripheral tissue is human tissue or human biological fluid.

15. The method according to claim 13 wherein said tissue is selected from the group consisting of adipose, brain, testes, kidney, and liver tissue.

16. The method according to claim 14 wherein said normal or peripheral tissue is selected from the group consisting of adipose, brain, testes, kidney, and liver tissue.

17. The method according to claim 13 wherein said tissue is breast tissue.

18. The method according to claim 13 wherein said tissue is ovarian tissue.

19. The method according to claim 14 wherein said normal or peripheral tissue is breast tissue.

20. The method according to claim 14 wherein said normal or peripheral tissue is ovarian tissue.

21. The method according to claim 1 wherein said normal or peripheral tissue is breast tissue from an individual patient.

22. The method according to claim 21 wherein said tissue is breast tissue from said patient.

23. The method according to claim 1 wherein said normal or peripheral tissue is ovarian tissue from an individual patient.

24. The method according to claim 23 herein said tissue specimen is ovarian tissue from said patient.

25. A method for diagnosing tumorigenicity in human breast tissue or biological fluid comprising measuring the expression or level of the full-length protein encode by SEQ ID NO: 16 in human tumorigenic breast tissue or biological fluid with an anti-GP88 antibody; measuring the expression or level of said protein in corresponding normal breast tissue or biological fluid; and diagnosing tumorigenicity by determining whether the measured expression or level of said protein in said tumorigenic breast tissue or biological fluid is higher than the expression or level in corresponding normal human breast tissue or biological fluid by an amount sufficient to indicate tumorigenicity.

26. A method for diagnosing tumorigenicity in human ovarian tissue or biological fluid comprising measuring the expression or level of the full-length protein encoded by SEQ ID NO: 16 in human tumorigenic ovarian tissue or biological fluid with an anti-GP88 antibody; measuring the expression or level of said protein in corresponding normal ovarian tissue or biological fluid; and diagnosing tumorigenicity by determining whether the measured expression or level of said protein in said tumorigenic ovarian tissue or biological fluid is higher than the expression or level in corresponding normal human ovarian tissue or biolgical fluid by an amount sufficient to indicate tumorigenicity.

27. The method according to claim 25 wherein said anti-GP88 antibody is produced in an animal immunized with a composition comprising SEQ ID NO: 6.

28. The method according to claim 25 wherein said anti-GP88 antibody is produced in an animal immunized with a composition comprising SEQ ID NO: 7.

29. The method according to claim 26 wherein said anti-GP88 antibody is produced in an animal immunized with a composition comprising SEQ ID NO: 6.

30. The method according to claim 26 wherein said anti-GP88 antibody is produced in an animal immunized with a composition comprising SEQ ID NO: 7.

31. The method according to claim 2 wherein said anti-GP88 antibody is produced in an animal immunized with a composition comprising SEQ ID NO: 16.

32. The method according to claim 10 wherein said immunoassay is an immunofluorescence assay.

33. The method according to claim 10 wherein said immunoassay is an chemiluminescence assay.

34. The method according to claim 25 wherein said anti-GP88 antibody is produced in an animal immunized with a composition comprising the protein encoded by SEQ ID NO: 16.

35. The method according to claim 26 wherein said anti-GP88 antibody is produced in an animal immunized with a composition comprising the protein encoded by SEQ ID NO: 16.

* * * * *

UNITED STATES PATENT AND TRADEMARK OFFICE
CERTIFICATE OF CORRECTION

PATENT NO. : 6,720,159 B1
APPLICATION NO. : 09/456886
DATED : April 13, 2004
INVENTOR(S) : Ginette Serrero It is certified that error appears in the above-identified patent and that said Letters Patent is hereby corrected as shown below:

Column 1, line 57, "characterixized" should read --characterised--;

Column 2, lines 35-36, "mice or humans" should read --a mammal--;

Column 4, line 46, "elimite" should read --eliminate--;

Column 5, line 25, "neutrazing" should read --neutralizing--;

Column 12, line 65, "a s called" should read --a so-called--;

Column 13:

Line 31, "neutrize" should read --neutralize--;

Line 54, "dosage of will" should read --dosage will--;

Column 14, line 53, "the. GP88" should read --the GP88--;

Column 17, line 22, "tansfection" should read --transfection--;

Column 22, line 53, "(FBS) our" should read --(FBS) by our--;

Column 23:

Line 13, "showed" should read --shown--;

Line 26, "epithehal" should read --epithelial--;

Line 28, "form" should read --from--;

Line 42, "MDA-MB468" should read --MDA-MB-468--;

Line 43, "insuin" should read --insulin--;

Column 25:

Line 6, "GP8S" should read --GP88--;

Line 33, "0 1" should read --0.1--;

UNITED STATES PATENT AND TRADEMARK OFFICE
CERTIFICATE OF CORRECTION

| | | |
|---|---|---|
| PATENT NO. | : 6,720,159 B1 | |
| APPLICATION NO. | : 09/456886 | |
| DATED | : April 13, 2004 | |
| INVENTOR(S) | : Ginette Serrero | |

It is certified that error appears in the above-identified patent and that said Letters Patent is hereby corrected as shown below:

Column 28, line 1, "(5'-CGGAC...) should read --(5'-CGAC...)--;

Column 30:

Line 7, "SEQ ID NO: 12)" should read --(SEQ ID NO: 12)--;

Line 10, "SEQ ID NO: 13)" should read --(SEQ ID NO: 13)--;

Line 56, "SEQ ID NO: 14)" should read --(SEQ ID NO: 14)--;

Line 59, "SEQ ID NO: 15)" should read --(SEQ ID NO: 15)--;

Column 32, line 36, "(405 bp" should read --(400 bp--;

Column 33, line 11, "$\geqq$" should read --$\geq$--;

Column 34, line 67, "(PMSF" should read --(PMSF)--;

Column 35, line 30, "GP8S" should read --GP88--;

Column 37, line 65, "phophorothioate" should read --phosphorothioate--;

Column 38:

Line 31, "48)" begins a new reference, should start back at the left of the column Line 44, "91989)" should read --(1989)--;

Line 51, "Sepp-lorenzino" should read --Sepp-Lorenzino--;

Line 52, "Inslin" should read --Insulin--;

UNITED STATES PATENT AND TRADEMARK OFFICE
CERTIFICATE OF CORRECTION

| | |
|---|---|
| PATENT NO. | : 6,720,159 B1 |
| APPLICATION NO. | : 09/456886 |
| DATED | : April 13, 2004 |
| INVENTOR(S) | : Ginette Serrero |

It is certified that error appears in the above-identified patent and that said Letters Patent is hereby corrected as shown below:

In the Claims of the following errors are corrected:

Column 60:

Claim 24, line 26, "herein" should read --wherein--; and

Claim 25, line 29, "encode" should read --encoded--.

Signed and Sealed this

Eighteenth Day of July, 2006

JON W. DUDAS
*Director of the United States Patent and Trademark Office*